United States Patent [19]
Yanofsky

[11] Patent Number: 5,811,536
[45] Date of Patent: Sep. 22, 1998

[54] CAULIFLOWER FLORAL MERISTEM IDENTITY GENES AND METHODS OF USING SAME

[75] Inventor: Martin F. Yanofsky, San Diego, Calif.

[73] Assignee: The Regents of the University of California, Oakland, Calif.

[21] Appl. No.: 592,214

[22] Filed: Jan. 26, 1996

[51] Int. Cl.$^6$ .......................... C12N 15/29; C12N 15/82; C12N 5/04

[52] U.S. Cl. .................. 536/23.6; 435/172.3; 435/320.1; 435/419

[58] Field of Search ................ 536/23.6; 435/320.1, 435/172.3, 252.3, 419

[56] References Cited

PUBLICATIONS

Anthony et al., Cloning and Sequence Analysis of a *flo/lfy* Homologue Isolated From Cauliflower (*Brassica oleracea*L. var. *botrytis*), *Plant. Molec. Biol.* 22:1163–1166 (1993).
Anthony et al., The cDNA Sequence of a Cauliflower *Apetala–1/squamosa* Homolog, *Plant Physiol.* 108:441–442 (1995).
Hulbert and Bennetzen, "Recombination at the Rp1 Locus of Maize," *Molec. Gen. Genet.* 226:377–382 (1991).
Scott et al., "Molecular and Cellular Aspects of Plant Reproduction," Cambridge, Great Britain: Cambridge University Press, pp. 18–29 (1994).
Sommer et al., "Deficiens, a Homeotic Gene Involved in the Control of Flower Morphogenesis in *Antirrhinum Majus*: the Protein Shows Homology to Transcription Factors," *The Embo. J.* 9:605–613 (1990).
Alvarez et al., "*Terminal flower*: A Gene Affecting Inflorescence Development in *Arabidopsis thaliana*," *Plant J.* 2:(1):103–116 (1992).
Bowman et al., "Control of Flower Development in *Arabidopsis thaliana* by APETALA1 and Interacting Genes," *Dev.* 119:721–743 (1993).
Chung et al., "Early Flowering and Reduced Apical Dominance Result From Ectopic Expression of a Rice MADS Box Gene," *Plant Mol. Bio.* 26:657–665 (1994).
Kempin et al., "Molecular Basis of the *cauliflower* Phenotype in Arabidopsis," *Science* 267:522–525 (1995).
King, "Molecular Genetics and Breeding of Vegetable Brassicas," *Euphytica* 50:97–112 (1990).
Mandel and Yanofsky, "A Gene Triggering Flower Formation in Arabidopsis," *Nature* 377:522–524 (1995).
Mandel et al., "Molecular Characterization of the Arabidopsis Floral Homeotic Gene APETALA1," *Nature* 360:273–277 (1992).
Purugganan et al., "Molecular Evolution of Flower Development: Diversification of the Plant MADS–Box Regulatory Gene Family," *Genetics* 140:345–356 (1995).
Weigel, "The Genetics of Flower Development: From Floral Induction to Ovule Morphogenesis," *Annu. Rev. Genetics* 29:19–39 (1995).
Yanofsky, "Floral Meristems to Floral Organs: Genes Controlling Early Events in Arabidopsis Flower Development," *Annu. Rev. Plant Physiol. Plant Mol. Biol.* 46:167–188 (1995).
Neuman et al. 1994. Plant Physiol. 106:1241–1255.
Adams et al. 1991. J. Bacteriol. 173(12): 3846–3854.

*Primary Examiner*—David T. Fox
*Attorney, Agent, or Firm*—Campbell & Flores LLP

[57] ABSTRACT

The present invention provides a nucleic acid molecule encoding a CAULIFLOWER (CAL) gene product such as a nucleic acid molecule encoding *Arabidopsis thaliana* CAL and a nucleic acid molecule encoding *Brassica oleracea* CAL (BoCAL). The invention also provides a nucleic acid molecule encoding a truncated CAL gene product such as a nucleic acid molecule encoding *Brassica oleracea* var. *botrytis* CAL (BobCAL). The invention also provides a nucleic acid containing the *Arabidopsis thaliana* CAL gene, a nucleic acid molecule containing the *Brassica oleracea* CAL gene and a nucleic acid molecule containing the *Brassica oleracea* var. *botrytis* CAL gene. The invention further provides a kit for converting shoot meristem to floral meristem and a kit for promoting early flowering in an angiosperm. The invention provides a CAL polypeptide and an antibody that specifically binds CAL polypeptide. In addition, the invention provides the truncated BobCAL polypeptide and an antibody that specifically binds truncated BobCAL polypeptide. The invention further provides a method of identifying a Brassica having a modified CAL allele by detecting a polymorphism associated with a CAL locus, where the CAL locus comprises a modified CAL allele that does not encode an active CAL gene product.

19 Claims, 44 Drawing Sheets

```
                                                                    -81
          *          *          *          *          *            *
GAATTCCTCG AGCTACGTCA GGGCCCTGAC GTAGCTCGAA GTCTGAGCTC TTCTTTATAT

-21
          *          *          *          *          *            *
CTCTCTTGTA GTTTCTTATT GGGGGTCTTT GTTTTGTTTG GTTCTTTTAG AGTAAGAAGT

*          *          *              *              *
TTCTTAAAAA AGGATCAAAA ATG GGA AGG GGT AGG GTT CAA TTG AAG AGG ATA
                       M   G   R   G   R   V   Q   L   K   R   I>      11

40
          *          *          *          *          *
GAG AAC AAG ATC AAT AGA CAA GTG ACA TTC TCG AAA AGA AGA GCT GGT
 E   N   K   I   N   R   Q   V   T   F   S   K   R   R   A   G>        27

100
          *          *          *          *
CTT TTG AAG AAA GCT CAT GAG ATC TCT GTT CTC TGT GAT GCT GAA GTT
 L   L   K   K   A   H   E   I   S   V   L   C   D   A   E   V>        43

160
     *         *          *          *              *
GCT CTT GTT GTC TTC TCC CAT AAG GGA AAA CTC TTC GAA TAC TCC ACT
 A   L   V   V   F   S   H   K   G   K   L   F   E   Y   S   T>        59

220
     *         *          *          *              *
GAT TCT TGT ATG GAG AAG ATA CTT GAA CGC TAT GAG AGG TAC TCT TAC
 D   S   C   M   E   K   I   L   E   R   Y   E   R   Y   S   Y>        75

*         *          *          *              *
GCC GAA AGA CAG CTT ATT GCA CCT GAG TCC GAC GTC AAT ACA AAC TGG
 A   E   R   Q   L   I   A   P   E   S   D   V   N   T   N   W>        91

280
          *          *          *          *          *
TCG ATG GAG TAT AAC AGG CTT AAG GCT AAG ATT GAG CTT TTG GAG AGA
 S   M   E   Y   N   R   L   K   A   K   I   E   L   L   E   R>       107

340
     *              *          *          *
AAC CAG AGG CAT TAT CTT GGG GAA GAC TTG CAA GCA ATG AGC CCT AAA
 N   Q   R   H   Y   L   G   E   D   L   Q   A   M   S   P   K>       123

400
     *         *          *          *              *
GAG CTT CAG AAT CTG GAG CAG CAG CTT GAC ACT GCT CTT AAG CAC ATC
 E   L   Q   N   L   E   Q   Q   L   D   T   A   L   K   H   I>       139

460
     *         *          *          *          *
CGC ACT AGA AAA AAC CAA CTT ATG TAC GAG TCC ATC AAT GAG CTC CAA
 R   T   R   K   N   Q   L   M   Y   E   S   I   N   E   L   Q>       155

*         *          *          *              *
AAA AAG GAG AAG GCC ATA CAG GAG CAA AAC AGC ATG CTT TCT AAA CAG
 K   K   E   K   A   I   Q   E   Q   N   S   M   L   S   K   Q>       171
```

FIG. IA

```
              520
               *                    *                  *                   *                  *
    ATC AAG GAG AGG GAA AAA ATT CTT AGG GCT CAA CAG GAG CAG TGG GAT
     I   K   E   R   E   K   I   L   R   A   Q   Q   E   Q   W   D>          187

580
         *               *                  *                  *
    CAG CAG AAC CAA GGC CAC AAT ATG CCT CCC CCT CTG CCA CCG CAG CAG
     Q   Q   N   Q   G   H   N   M   P   P   P   L   P   P   Q   Q>          203

640
         *                 *                *                  *
    CAC CAA ATC CAG CAT CCT TAC ATG CTC TCT CAT CAG CCA TCT CCT TTT
     H   Q   I   Q   H   P   Y   M   L   S   H   Q   P   S   P   F>          219

700
         *               *                  *                *
    CTC AAC ATG GGT GGT CTG TAT CAA GAA GAT GAT CCT ATG GCA ATG AGG
     L   N   M   G   G   L   Y   Q   E   D   D   P   M   A   M   R>          235

*                *                 *                 *                  *
    AAT GAT CTC GAA CTG ACT CTT GAA CCC GTT TAC AAC TGC AAC CTT GGC
     N   D   L   E   L   T   L   E   P   V   Y   N   C   N   L   G>          251

760
               *                  *                  *                  *                  *
    TGC TTC GCC GCA TGA AGC ATT TCC ATA TAT ATA TTT GTA ATC GTC AAC
     C   F   A   A   *   S   I   S   I   Y   I   F   V   I   V   N>          267

820
         *                *                  *                *
    AAT AAA AAC AGT TTG CCA CAT ACA TAT AAA TAG TGG CTA GGC TCT TTT
     N   K   N   S   L   P   H   T   Y   K   *   W   L   G   S   F>          283

880
         *                *                  *                *                  *
    CAT CCA ATT AAT ATA TTT TGG CAA ATG TTC GAT GTT CTT ATA TCA TCA
     H   P   I   N   I   F   W   Q   M   F   D   V   L   I   S   S>          299

940
         *                 *                  *                *                  *                   *
    TAT ATA AAT TAG C AGGCTCCTTT CTTCTTTTGT AATTTGATAA GTTTATTTGC
     Y   I   N   *   X>                                                       302

1000
         *                 *                  *                  *                 *                  *
    TTCAATATGG AGCAAAATTG TAATATATTT GAAGGTCAGA GAGAATGAAC GTGAACTTAA

1060
         *                 *                  *                  *                 *                  *
    TAGAAAAAAA AAAAAAAAAA AAAAAAAAAA AAAAAAAAAA AAACCCGACG TAGCTCGAGG

AATTC
```

FIG. IB

```
                                              *                   *
TCTTAGAGGA AATAGTTCCT TTAAAAGGGA TAAAA ATG GGA AGG GGT AGG GTT CAG
                                       M   G   R   G   R   V   Q    7

25
    *                *              *                 *
TTG AAG AGG ATA GAA AAC AAG ATC AAT AGA CAA GTG ACA TTC TCG AAA
 L   K   R   I   E   N   K   I   N   R   Q   V   T   F   S   K   23

85
    *             *                *                 *                 *
AGA AGA GCT GGT CTT ATG AAG AAA GCT CAT GAG ATC TCT GTT CTG TGT
 R   R   A   G   L   M   K   K   A   H   E   I   S   V   L   C   39

*                *                 145
                                           *                 *                *
GAT GCT GAA GTT GCG CTT GTT GTC TTC TCC CAT AAG GGG AAA CTC TTT
 D   A   E   V   A   L   V   V   F   S   H   K   G   K   L   F   55

*                *                *                 205
                                                            *
GAA TAC TCC ACT GAT TCT TGT ATG GAG AAG ATA CTT GAA CGC TAT GAG
 E   Y   S   T   D   S   C   M   E   K   I   L   E   R   Y   E   71

*               *                 *                *                *
AGA TAC TCT TAC GCC GAG AGA CAG CTT ATA GCA CCT GAG TCC GAC TCC
 R   Y   S   Y   A   E   R   Q   L   I   A   P   E   S   D   S   87

265
*               *                *                 *                *
AAT ACG AAC TGG TCG ATG GAG TAT AAT AGG CTT AAG GCT AAG ATT GAG
 N   T   N   W   S   M   E   Y   N   R   L   K   A   K   I   E  103

325
    *       *                 *                *                *
CTT TTG GAG AGA AAC CAG AGG CAC TAT CTT GGG GAA GAC TTG CAA GCA
 L   L   E   R   N   Q   R   H   Y   L   G   E   D   L   Q   A  119

*                *                385
                                           *                 *                *
ATG AGC CCT AAG GAA CTC CAG AAT CTA GAG CAA CAG CTT GAT ACT GCT
 M   S   P   K   E   L   Q   N   L   E   Q   Q   L   D   T   A  135

445
    *                *                 *              *                *
CTT AAG CAC ATC CGC TCT AGA AAA AAC CAA CTT AGT TAC GAC TCC ATC
 L   K   H   I   R   S   R   K   N   Q   L   S   Y   D   S   I  151

*               *                *                *                *
AAT GAG CTC CAA AGA AAG GAG AAA GCC ATA CAG GAA CAA AAC AGC ATG
 N   E   L   Q   R   K   E   K   A   I   Q   E   Q   N   S   M  167

505
*               *                *                 *                *
CTT TCC AAG CAG ATT AAG GAG AGG GAA AAC GTT CTT AGG GCG CAA CAA
 L   S   K   Q   I   K   E   R   E   N   V   L   R   A   Q   Q  183
```

FIG. 2A

```
                              565                    *                *                *
       *                       *
GAG CAA TGG GAC GAG CAG AAC CAT GGC CAT AAT ATG CCT CCG CCT CCA
 E   Q   W   D   E   Q   N   H   G   H   N   M   P   P   P   P     199

*             *          625              *                *
                                      *
CCC CCG CAG CAG CAT CAA ATC CAG CAT CCT TAC ATG CTC TCT CAT CAG
 P   P   Q   Q   H   Q   I   Q   H   P   Y   M   L   S   H   Q     215

*             *             *         685
                                                    *
CCA TCT CCT TTT CTC AAC ATG GGG GGG CTG TAT CAA GAA GAA GAT CAA
 P   S   P   F   L   N   M   G   G   L   Y   Q   E   E   D   Q     231

*           *             *             *             *
ATG GCA ATG AGG AGG AAC GAT CTC GAT CTG TCT CTT GAA CCC GGT TAT
 M   A   M   R   R   N   D   L   D   L   S   L   E   P   G   Y     247

745          *
  *
AAC TGC AAT CTC GGC TGC
 N   C   N   L   G   C                                             253
```

FIG. 2B

```
ATG GGA AGG GGT AGG GTT CAG TTG AAG AGG ATA GAA AAC AAG ATC AAT
 M   G   R   G   R   V   Q   L   K   R   I   E   N   K   I   N     16

60
AGA CAA GTG ACA TTC TCG AAA AGA AGA GCT GGT CTT ATG AAG AAA GCT
 R   Q   V   T   F   S   K   R   R   A   G   L   M   K   K   A     32

120
CAT GAG ATC TCT GTT CTG TGT GAT GCT GAA GTT GCG CTT GTT GTC TTC
 H   E   I   S   V   L   C   D   A   E   V   A   L   V   V   F     48

180
TCC CAT AAG GGG AAA CTC TTT GAA TAC CCC ACT GAT TCT TGT ATG GAG
 S   H   K   G   K   L   F   E   Y   P   T   D   S   C   M   E     64

240
GAG ATA CTT GAA CGC TAT GAG AGA TAC TCT TAC GCC GAG AGA CAG CTT
 E   I   L   E   R   Y   E   R   Y   S   Y   A   E   R   Q   L     80

ATA GCA CCT GAG TCC GAC TCC AAT ACG AAC TGG TCG ATG GAG TAT AAT
 I   A   P   E   S   D   S   N   T   N   W   S   M   E   Y   N     96

300
AGG CTT AAG GCT AAG ATT GAG CTT TTG GAG AGA AAC CAG AGG CAC TAT
 R   L   K   A   K   I   E   L   L   E   R   N   Q   R   H   Y    112

360
CTT GGG GAA GAC TTG CAA GCA ATG AGC CCT AAG GAA CTC CAG AAT CTA
 L   G   E   D   L   Q   A   M   S   P   K   E   L   Q   N   L    128

420
GAG CAA CAG CTT GAT ACT GCT CTT AAG CAC ATC CGC TCT AGA AAA AAC
 E   Q   Q   L   D   T   A   L   K   H   I   R   S   R   K   N    144

480
CAA CTT ATG TAC GAC TCC ATC AAT GAG CTC CAA AGA AAG GAG AAA GCC
 Q   L   M   Y   D   S   I   N   E   L   Q   R   K   E   K   A    160

ATA CAG GAA CAA AAC AGC ATG CTT TCC AAG CAG ATT AAG GAG AGG GAA
 I   Q   E   Q   N   S   M   L   S   K   Q   I   K   E   R   E    176

540
AAC GTT CTT AGG GCG CAA CAA GAG CAA TGG GAC GAG CAG AAC CAT GGC
 N   V   L   R   A   Q   Q   E   Q   W   D   E   Q   N   H   G    192
```

FIG. 3A

```
                                    600
       *                *             *                    *                *
CAT AAT ATG CCT CCG CCT CCA CCC CCG CAG CAG CAT CAA ATC CAG CAT
 H   N   M   P   P   P   P   P   P   Q   Q   H   Q   I   Q   H      208
                                              660
       *                *             *         *                    *
CCT TAC ATG CTC TCT CAT CAG CCA TCT CCT TTT CTC AAC ATG GGA GGG
 P   Y   M   L   S   H   Q   P   S   P   F   L   N   M   G   G      224
                                                                720
       *                *                *             *             *
CTG TAT CAA GAA GAA GAT CAA ATG GCA ATG AGG AGG AAC GAT CTC GAT
 L   Y   Q   E   E   D   Q   M   A   M   R   R   N   D   L   D      240
       *                *             *             *
CTG TCT CTT GAA CCC GTT TAC AAC TGC AAC CTT GGC CGT CGC TGC TGA
 L   S   L   E   P   V   Y   N   C   N   L   G   R   R   C   *      255
```

FIG. 3B

```
CGGTTGCGCGCCGCAATCGATCGACGGAAGAGAAAGAGCAGCTAGCTAGCAGATCGGAGACGGAGCACGGCAACAAGGCG
    GCACGAGTCCTCCTCCTCTGCATCCCCACCCCACCTTCTCCTTAAAGCTACCTGCCTACCCGG    60

ATG GGG CGC GGC AAG GTA CAG CTG AAG CGG ATA AAC AAG CGG CAG GTG ACC          120
 M   G   R   G   K   V   Q   L   K   R   I   N   K   R   Q   V   T            40

TTC TCC AAG CGC CGG AAC GGC CTG CTC CTC CAC GAG ATC TCC GTC CTC TGC GAT       180
 F   S   K   R   R   N   G   L   L   L   H   E   I   S   V   L   C   D         60

GCC GAG GTC GCC ATC GTC GTC GTC TTC TCC AAG GCG AAG GGC TAC TAT GCC ACC GAC   240
 A   E   V   A   I   V   V   V   F   S   K   A   K   G   Y   Y   A   T   D     80

TCC CGC ATG GAC AAA ATT CTT GAA CGC TAT CGA TAT GAG CTC TCC GAG GCT CTT       300
 S   R   M   D   K   I   L   E   R   Y   R   Y   E   L   S   E   A   L       100

ATT TCA GCT GAA TCT GAA AGT GAG GGA AAT TGG TGC CAC CTG ATG TAC TCC AGG AAG GCC   360
 I   S   A   E   S   E   G   N   W   C   H   L   M   Y   S   R   K   A     120

AAA ATT GAG ACC ATA CAA CAA CAA CTA GAG CAT GAG CAG GAT CTA AAG CAC ATC AGA   420
 K   I   E   T   I   Q   Q   Q   L   E   H   E   Q   D   L   K   H   I   R   140

AAT CCC AAG GAG AGC CAC CTC AAG CAC ATG GCC CTG CAG CTG GAT TCT ATT CTT GCG GAG AAG GCC   480
 N   P   K   E   S   H   L   K   H   M   A   L   Q   L   D   S   I   L   A   E   K   A   160

TCA AGG AAG AGC CAG GAG AAC CAC CAA CAA CAA CAA GAG AAA GCT CTT CAG CAG CAG GAC GAC AAG AAG   540
 S   R   K   S   Q   E   N   H   Q   Q   Q   Q   E   K   A   L   Q   Q   Q   D   D   K   K   180

CTG CAG GAG GAG CAG CAG CAG CAG CAA CAA GTG GTG CAG CTT GCA TGG GAA CAG ATG ATG CAG AGG TCA   600
 L   Q   E   E   Q   Q   Q   Q   Q   Q   V   V   Q   L   A   W   E   Q   M   M   Q   R   S   200

AGC CGG CAG ACA TCA TCA TCG TCA TCA TCC TCG TCC TCC CAG GAG CAG CAT GCA AGG GCC CAG GTC GCG   660
 S   R   Q   T   S   S   S   S   S   S   S   S   S   Q   E   Q   H   A   R   A   Q   V   A   220

CAG ACA AGC TCA TCA TCA TCG TCA TCA TCC TCG TCC TCC CAG GAG CAG GAT CAG GAG CAG CAG CTG CCG CCT
 Q   T   S   S   S   S   S   S   S   S   S   Q   E   Q   D   Q   E   Q   Q   L   P   P
```

FIG. 4A

```
CCA CAC AAC ATC TGC TTC CCG CCG TTG ACA ATG GGA GAT AGA GGT GAA GAG CTG GCT GCG    720
 P   H   N   I   C   F   P   P   L   T   M   G   D   R   G   E   E   L   A   A    240

GCG GCG GCG CAG CAG CAG CAG CCA CTG CCG CCG GGG CAG GCG CAA CCG CAG CTC CGC ATC    780
 A   A   A   Q   Q   Q   Q   P   L   P   P   G   Q   A   Q   P   Q   L   R   I    260

GCA GGT CTG CCA CCA TGG ATG CTG AGC CAC CTC AAT GCA TAA GGAGAGGGTCGATGAACACATCG    845
 A   G   L   P   P   W   M   L   S   H   L   N   A   *                             273

ACCTCCTCTCTCTCTCGTCATGGATCATCATGACGTACGGCGTACCACATATGGTTGCTGCCTGCCCCATCGATCG       924
CGAGCAATGGCACGCTCATGCAAGTGATCATTGCTCCCCGTTGGTTAAACCCTAGCCTATGTTCATGGGCGTCAGCAACT    1003
AAGCTAAACTATTGTTTGCAAGAAAGGGTAAACCGCTGTGTAATCTTGTCCAGCTATCAGTATGCTTGT              1082
TACTGCCCAGTTAGTAGTATTAACCTTGAATCTAGCGGCGCTTTTGGTGAGAGGGTGCAGTTTACTTTAAACATCG       1161
TGTAAATAGTAGTATTAATCGATTTGGGCATCT(A)n                                              1195
```

FIG. 4B

```
          *              *              *              *              *
TTAAGAGAA ATG GGA AGG GGT AGG GTT GAA TTG AAG AGG ATA GAG AAC AAG
          M   G   R   G   R   V   E   L   K   R   I   E   N   K>       14

51
        *              *              *              *
ATC AAT AGA CAA GTG ACA TTC TCG AAA AGA AGA ACT GGT CTT TTG AAG
 I   N   R   Q   V   T   F   S   K   R   R   T   G   L   L   K>        30

111
 *              *              *              *              *
AAA GCT CAG GAG ATC TCT GTT CTT TGT GAT GCC GAG GTT TCC CTT ATT
 K   A   Q   E   I   S   V   L   C   D   A   E   V   S   L   I>        46

171
 *              *              *              *              *
GTC TTC TCC CAT AAG GGC AAA TTG TTC GAG TAC TCC TCT GAA TCT TGC
 V   F   S   H   K   G   K   L   F   E   Y   S   S   E   S   C>        62

231
 *              *              *              *              *
ATG GAG AAG GTA CTA GAA CGC TAC GAG AGG TAT TCT TAC GCC GAG AGA
 M   E   K   V   L   E   R   Y   E   R   Y   S   Y   A   E   R>        78

*              *              *              *              *
CAG CTG ATT GCA CCT GAC TCT CAC GTT AAT GCA CAG ACG AAC TGG TCA
 Q   L   I   A   P   D   S   H   V   N   A   Q   T   N   W   S>        94

291
        *              *              *              *
ATG GAG TAT AGC AGG CTT AAG GCC AAG ATT GAG CTT TTG GAG AGA AAC
 M   E   Y   S   R   L   K   A   K   I   E   L   L   E   R   N>        110

351
 *              *      *              *              *
CAA AGG CAT TAT CTG GGA GAA GAG TTG GAA CCA ATG AGC CTC AAG GAT
 Q   R   H   Y   L   G   E   E   L   E   P   M   S   L   K   D>        136

411
 *              *              *      *              *
CTC CAA AAT CTG GAG CAG CAG CTT GAG ACT GCT CTT AAG CAC ATT CGC
 L   Q   N   L   E   Q   Q   L   E   T   A   L   K   H   I   R>        152

471
 *              *              *              *      *
TCC AGA AAA AAT CAA CTC ATG AAT GAG TCC CTC AAC CAC CTC CAA AGA
 S   R   K   N   Q   L   M   N   E   S   L   N   H   L   Q   R>        168

*              *              *              *              *
AAG GAG AAG GAG ATA CAG GAG GAA AAC AGC ATG CTT ACC AAA CAG ATA
 K   E   K   E   I   Q   E   E   N   S   M   L   T   K   Q   I>        184

531
        *              *              *              *
AAG GAG AGG GAA AAC ATC CTA AAG ACA AAA CAA ACC CAA TGT GAG CAG
 K   E   R   E   N   I   L   K   T   K   Q   T   Q   C   E   Q>        200

591
 *      *      *              *              *
CTG AAC CGC AGC GTC GAC GAT GTA CCA CAG CCA CAA CCA TTT CAA CAC
```

FIG. 5A

```
    L   N   R   S   V   D   D   V   P   Q   P   Q   P   F   Q   H>  216
                                            651
    *               *               *               *               *
    CCC CAT CTT TAC ATG ATC GCT CAT CAG ACT TCT CCT TTC CTA AAT ATG
    P   H   L   Y   M   I   A   H   Q   T   S   P   F   L   N   M>  232
                                                            711
    *               *               *               *       *
    GGT GGT TTG TAC CAA GGA GAA GAC CAA ACG GCG ATG AGG AGG AAC AAT
    G   G   L   Y   Q   G   E   D   Q   T   A   M   R   R   N   N>  248

*               *               *               *               *
    CTG GAT CTG ACT CTT GAA CCC ATT TAC AAT TAC CTT GGC TGT TAC GCC
    L   D   L   T   L   E   P   I   Y   N   Y   L   G   C   Y   A>  262

GCT TGA --
    A   *   X>                                                      263
```

FIG. 5B

```
ATG GGA AGG GGT AGG GTT GAA ATG AAG AGG ATA GAG AAC AAG ATC AAC
 M   G   R   G   R   V   E   M   K   R   I   E   N   K   I   N     16
              60
 *            *                   *               *               *
CGA CAA GTG ACG TTT TCG AAA AGA AGA GCT GGT CTT TTG AAG AAA GCC
 R   Q   V   T   F   S   K   R   R   A   G   L   L   K   K   A     32
      *           *          120
                              *               *               *
CAT GAG ATC TCG ATC CTT TGT GAT GCT GAG GTT TCC CTT ATT GTC TTC
 H   E   I   S   I   L   C   D   A   E   V   S   L   I   V   F     48
      *           *           *          180
                                          *                   *
TCC CAT AAG GGG AAA CTG TTC GAG TAC TCG TCT GAA TCT TGC ATG GAG
 S   H   K   G   K   L   F   E   Y   S   S   E   S   C   M   E     64
      *           *           *               *          240
                                                          *
AAG GTA CTA GAA CAC TAC GAG AGG TAC TCT TAC GCC GAG AAA CAG CTA
 K   V   L   E   H   Y   E   R   Y   S   Y   A   E   K   Q   L     80
      *           *           *               *
AAA GTT CCA GAC TCT CAC GTC AAT GCA CAA ACG AAC TGG TCA GTG GAA
 K   V   P   D   S   H   V   N   A   Q   T   N   W   S   V   E     96
 *           300
              *                   *               *               *
TAT AGC AGG CTT AAG GCT AAG ATT GAG CTT TTG GAG AGA AAC CAA AGG
 Y   S   R   L   K   A   K   I   E   L   L   E   R   N   Q   R    112
      *           *          360
                              *                   *               *
CAT TAT CTG GGC GAA GAT TTA GAA TCA ATC AGC ATA AAG GAG CTA CAG
 H   Y   L   G   E   D   L   E   S   I   S   I   K   E   L   Q    128
      *           *               *          420
                                              *                   *
AAT CTG GAG CAG CAG CTT GAC ACT TCT CTT AAA CAT ATT CGC TCG AGA
 N   L   E   Q   Q   L   D   T   S   L   K   H   I   R   S   R    144
                                                             480
      *           *               *               *          *
AAA AAT CAA CTA ATG CAC GAG TCC CTC AAC CAC CTC CAA AGA AAG GAG
 K   N   Q   L   M   H   E   S   L   N   H   L   Q   R   K   E    160
      *           *               *               *
AAA GAA ATA CTG GAG GAA AAC AGC ATG CTT GCC AAA CAG ATA AGG GAG
 K   E   I   L   E   E   N   S   M   L   A   K   Q   I   R   E    176
 *          540
             *                    *               *               *
AGG GAG AGT ATC CTA AGG ACA CAT CAA AAC CAA TCA GAG CAG CAA AAC
 R   E   S   I   L   R   T   H   Q   N   Q   S   E   Q   Q   N    192
```

FIG. 6A

```
                                600
    *                *           *                 *             *
CGC AGC CAC CAT GTA GCT CCT CAG CCG CAA CCG CAG TTA AAT CCT TAC
 R   S   H   H   V   A   P   Q   P   Q   P   Q   L   N   P   Y      208

*                *           *          660
                                             *                 *
ATG GCA TCA TCT CCT TTC CTA AAT ATG GGT GGC ATG TAC CAA GGA GAA
 M   A   S   S   P   F   L   N   M   G   G   M   Y   Q   G   E      224

720
    *                *                *           *             *
TAT CCA ACG GCG GTG AGG AGG AAC CGT CTC GAT CTG ACT CTT GAA CCC
 Y   P   T   A   V   R   R   N   R   L   D   L   T   L   E   P      240

*                *           *
ATT TAC AAC TGC AAC CTT GGT TAC TTT GCC GCA TGA
 I   Y   N   C   N   L   G   Y   F   A   A   *                      251
```

FIG. 6B

```
ATG GGA AGG GGT AGG GTT GAA ATG AAG AGG ATA GAG AAC AAG ATC AAC
 M   G   R   G   R   V   E   M   K   R   I   E   N   K   I   N     16
              60
  *            *            *            *            *
AGA CAA GTG ACG TTT TCG AAA AGA AGA GCT GGT CTT TTG AAG AAA GCC
 R   Q   V   T   F   S   K   R   R   A   G   L   L   K   K   A     32
                      120
  *            *       *            *            *
CAT GAG ATC TCG ATT CTT TGT GAT GCT GAG GTT TCC CTT ATT GTC TTC
 H   E   I   S   I   L   C   D   A   E   V   S   L   I   V   F     48
                                        180
  *            *            *            *            *
TCC CAT AAG GGG AAA CTG TTC GAG TAC TCG TCT GAA TCT TGC ATG GAG
 S   H   K   G   K   L   F   E   Y   S   S   E   S   C   M   E     64
                                                     240
  *            *            *            *             *
AAG GTA CTA GAA CGC TAC GAG AGG TAC TCT TAC GCC GAG AAA CAG CTA
 K   V   L   E   R   Y   E   R   Y   S   Y   A   E   K   Q   L     80
  *            *            *            *
AAA GCT CCA GAC TCT CAC GTC AAT GCA CAA ACG AAC TGG TCA ATG GAA
 K   A   P   D   S   H   V   N   A   Q   T   N   W   S   M   E     96
              300
  *             *            *            *            *
TAT AGC AGG CTT AAG GCT AAG ATT GAG CTT TGG GAG AGG AAC CAA AGG
 Y   S   R   L   K   A   K   I   E   L   W   E   R   N   Q   R    112
                          360
  *            *            *            *            *
CAT TAT CTG GGA GAA GAT TTA GAA TCA ATC AGC ATA AAG GAG CTA CAG
 H   Y   L   G   E   D   L   E   S   I   S   I   K   E   L   Q    128
                                             420
  *            *            *             *            *
AAT CTG GAG CAG CAG CTT GAC ACT TCT CTT AAA CAT ATT CGC TCC AGA
 N   L   E   Q   Q   L   D   T   S   L   K   H   I   R   S   R    144
                                                             480
  *            *            *            *                    *
AAA AAT CAA CTA ATG CAC TAG T CCCTCA ACCACCTCCA AAGAAAGGAG
 K   N   Q   L   M   H   *  X                                     150
                                                     540
                *            *            *            *            *
AAAGAAATAC TGGAGGAAAA CAGCATGCTT GCCAAACAGA TAAAGGAGAG GGAGAGTATC
                                                             600
       *            *            *            *            *
CTAAGGACAC ATCAAAACCA ATCAGAGCAG CAAAACCGCA GCCACCATGT AGCTCCTCAG
                                                             660
       *            *            *            *            *
CCGCAACCGC AGTTAAATCC TTACATGGCA TCATCTCCTT TCCTAAATAT GGGTGGCATG
                                                             720
       *            *            *            *            *
TACCAAGGAG AATATCCAAC GGCGGTGAGG AGGAACCGTC TCGATCTGAC TCTTGAACCC
       *            *            *
ATTTACAACT GCAACCTTGG TTACTTTGCC GCATGA
```

FIG. 7

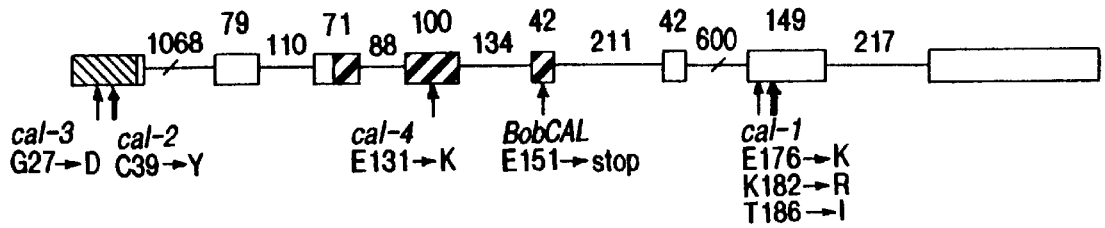

FIG. 8A

```
CAL    MGRGRVLLKRIKNKINRQVTFSKRRTGLLKKAQKISVLCDAKVSLIVFSK      50
BoCAL          M                  A       H    I
BobCAL         M                  A       H    I
AP1            Q                  A       H
                                                       A V

CAL    KGKLFEYSSESCMEKVLERYERYSYAERQLIAPDSHVNAQTNWSMEYSRL     100
BoCAL             H                K KV
BobCAL                             K K
AP1           TD     I                      E D  --         N

CAL    KAKIELLERNQRHYLGEELEPMSLKDLQNLEQQLETALKHIRSRKNQLMY     150
BoCAL                    D SI I E         D S               H
BobCAL          W        D SI I E         D                 H
AP1                      D QA  P E         D       T        Y

CAL    ESLNHLQRKEKEIQEENSMLTKQIKERENILKTKQTQCEQLNRSVDDVPQ     200
BoCAL                L  V A    R    S     R H N  S  Q   HHVA
BobCAL *
AP1        I E K    A    Q    S         K  RAQ E WD Q QGHNMP -

CAL    PQPFQHPHL---YMIAHQTSPFLNMGGLYQGEDQTAMRRNNLDLTLEPIY     247
BoCAL     QLN YM     -----AS       M    YP  V   R
BobCAL
AP1       L P QHQIQHP  LS  P           ED PM    D E     V

CAL    NY-LGCYAA*                                             255
BoCAL    CN  YF
BobCAL
AP1      CN   F
```

```
         *          *          *          *          *
GAATTCCCCG GATCTCCATA TACATATCAT ACATATATAT AGTATACTAT
        60
         *          *          *          *          *
CTTTAGACTG ATTTCTCTAT ACACTATCTT TTAACTTATG TATCGTTTCA
                   120
         *          *          *          *          *
AAACTCAGGA CGTACATGTT TTAAATTTGG TTATATAACC ACGACCATTT
                              180
         *          *          *          *          *
CAAGTATATA TGTCATACCA TACCAGATTT AATATAACTT CTATGAAGAA
                                         240
         *          *          *          *          *
AATACATAAA GTTGGATTAA AATGCAAGTG ACATCTTTTT AGCATAGGTT
                                                    300
         *          *          *          *          *
CATTTGGCAT AGAAGAAATA TATAACTAAA AATGAACTTT AACTTAAATA
         *          *          *          *          *
GATTTTACTA TATTACAATT TTTCTTTTTA CATGGTCTAA TTTATTTTTC
        360
         *          *          *          *          *
TAAAATTAGT ATGATTGTTG TTTTGATGAA ACAATAATAC CGTAAGCAAT
                   420
         *          *          *          *          *
AGTTGCTAAA AGATGTCCAA ATATTTATAA ATTACAAAGT AAATCAAATA
                              480
         *          *          *          *          *
AGGAAGAAGA CACGTGGAAA ACACCAAATA AGAGAAGAAA TGGAAAAAAC
                                         540
         *          *          *          *          *
AGAAAGAAAT TTTTTAACAA GAAAAATCAA TTAGTCCTCA AACCTGAGAT
                                                    600
         *          *          *          *          *
ATTTAAAGTA ATCAACTAAA ACAGGAACAC TTGACTAACA AAGAAATTTG
         *          *          *          *          *
AAATGTGGTC CAACTTTCAC TTAATTATAT TATTTTCTCT AAGGCTTATG
        660
         *          *          *          *          *
CAATATATGC CTTAAGCAAA TGCCGAATCT GTTTTTTTTT TTTGTTATTG
                   720
         *          *          *          *          *
GATATTGACT GAAAATAAGG GGTTTTTTCA CACTTGAAGA TCTCAAAAGA
                              780
         *          *          *          *          *
GAAAACTATT ACAACGGAAA TTCATTGTAA AAGAAGTGAT TAAGCAAATT
                                         840
         *          *          *          *          *
```

FIG. IOA

```
GAGCAAAGGT TTTTATGTGG TTTATTTCAT TATATGATTG ACATCAAATT
                                                    900
         *          *          *          *          *
GTATATATAT GGTTGTTTTA TTTAACAATA TATATGGATA TAACGTACAA
         *          *          *          *          *
ACTAAATATG TTTGATTGAC GAAAAAAAAT ATATGTATGT TTGATTAACA
       960
         *          *          *          *          *
ACATAGCACA TATCAACTGA TTTTTGTCCT GATCATCTAC AACTTAATAA
              1020
         *          *          *          *          *
GAACACACAA CATTGAAAAA ATCTTTGACA AAATACTATT TTTGGGTTTG
                         1080
         *          *          *          *          *
AAATTTTGAA TACTTACAAT TATCTTCTCG ATCTTCCTCT CTTTCCTTAA
                                    1140
         *          *          *          *          *
ATCCTGCGTA CAAATCCGTC GACGCAATAC ATTACACAGT TGTCAATTGG
                                                   1200
         *          *          *          *          *
TTCTCAGCTC TACCAAAAAC ATCTATTGCC AAAAGAAAGG TCTATTTGTA
         *          *          *          *          *
CTTCACTGTT ACAGCTGAGA ACATTAAATA TAATAAGCAA ATTTGATAAA
      1260
         *          *          *          *          *
ACAAAGGGTT CTCACCTTAT TCCAAAAGAA TAGTGTAAAA TAGGGTAATA
              1320
         *          *          *          *          *
GAGAAATGTT AATAAAAGGA AATTAAAAAT AGATATTTTG GTTGGGTTCA
                         1380
         *          *          *          *          *
GATTTTGTTT CGTAGATCTA CAGGGAAATC TCCGCCGTCA ATGCAAAGCG
                                    1440
         *          *          *          *          *
AAGGTGACAC TTGGGGAAGG ACCAGTGGTC GTACAATGTT ACTTACCCAT
                                                   1500
         *          *          *          *          *
TTCTCTTCAC GAGACGTCGA TAATCAAATT GTTTATTTTC ATATTTTTAA
         *          *          *          *          *
GTCCGCAGTT TTATTAAAAA ATCATGGACC CGACATTAGT ACGAGATATA
      1560
         *          *          *          *          *
CCAATGAGAA GTCGACACGC AAATCCTAAA GAAACCACTG TGGTTTTTGC
              1620
         *          *          *          *          *
AAACAAGAGA AACCAGCTTT AGCTTTTCCC TAAAACCACT CTTACCCAAA
```

FIG. 10B

```
                          1680
    *         *          *          *          *
TCTCTCCATA AATAAAGATC CCGAGACTCA AACACAAGTC TTTTTATAAA
                                   1740
    *         *          *          *          *
GGAAAGAAAG AAAAACTTTC CTAATTGGTT CATACCAAAG TCTGAGCTCT
                                              1800
    *         *          *          *          *
TCTTTATATC TCTCTTGTAG TTTCTTATTG GGGGTCTTTG TTTTGTTTGG
    *         *          *          *          *
TTCTTTTAGA GTAAGAAGTT TCTTAAAAAA GGATCAAAAA TGGGAAGGGG
         1860
    *         *          *          *          *
TAGGGTTCAA TTGAAGAGGA TAGAGAACAA GATCAATAGA CAAGTGACAT
               1920
    *         *          *          *          *
TCTCGAAAAG AAGAGCTGGT CTTTTGAAGA AAGCTCATGA GATCTCTGTT
                                   1980
    *         *          *          *          *
CTCTGTGATG CTGAAGTTGC TCTTGTTGTC TTCTCCCATA AGGGGAAACT
                                              2040
    *         *          *          *          *
CTTCGAATAC TCCACTGATT CTTGGTAACT TCAACTAATT CTTTACTTTT
                                                   2100
    *         *          *          *          *
AAAAAAATCT TTTAATCTGC TACTTTATAT AGTTTTTTTC CCCC----GG
    *         *          *          *          *
TCTATGATTC ATACTGTTTT GTTATTATAA AGGTATCATA GAGATCGGTA
         2160
    *         *          *          *          *
CTTGATTTGT TATAGGAAAT CTTGGTTTAA TTGCATAAAA CCATCATTAG
                    2220
    *         *          *          *          *
ATTTATCCTA AAATGTGATG ATATTTTGGT CACATCTCCA TATTATTTAT
                         2280
    *         *          *          *          *
ATAATAAAAT GATAATTGGT TGATGATAAA GCTAACCCTA ATTCTGTGAA
                                         2340
    *         *          *          *          *
ATGATCAGTA TGGAGAAGAT ACTTGAACGC TATGAGAGGT ACTCTTACGC
                                                   2400
    *         *          *          *          *
CGAAAGACAG CTTATTGCAC CTGAGTCCGA CGTCAATGTA TTTCAATAAA
    *         *          *          *          *
TATTTCTCCT TTTAATCCAC ATATATATTA TATCAATCTA TTTGTAGTAT
    2460
    *         *          *          *          *
```

FIG. 10C

```
TGATGAATTT TATTTGTATA AAACTTCTGG TACACAGACA AACTGGTCGA
                2520
             *        *          *          *          *
TGGCGTATAA CAGGCTTAAG GCTAAGATTG AGCTTTTGGA GAGAAACCAG
                          2580
             *        *          *          *          *
AGGTACACAT TTACACTCAT CACATTTCTA TCTAGAAAAT CGATCGGGTT
                                            2640
             *        *          *          *          *
CCATTTTAAA GTAAGTTAAA ATTCATTGAT GCTATTGAAA TTCAGGCATT
                                                       2700
             *        *          *          *          *
ATCTTGGGGA AGACTTGCAA GCAATGAGCC CTAAAGAGCT TCAGAATCTG
             *        *          *          *          *
GAGCAGCAGC TTGACACTGC TCTTAAGCAC ATCCGCACTA GAAAAGTATT
        2760
             *        *          *          *          *
GCCTTCTGCT ATTTCGTTGA ACATATCTAT ATAACTTAAA CGTTTACAAG
                2820
             *        *          *          *          *
TGTTATTATA ATGTGAACAT TGAAATACAT ATGTGTATGT ATCAATATAT
                          2880
             *        *          *          *          *
ATATCAGTAA TCAATATCAA TTTGATATGT CTATAGGTTG GTTCGAATGT
                                            2940
             *        *          *          *          *
ATGAGTTATG TTGTGTATTT TAAGACTCCA TATTACTTAA AGTAATGGGT
                                                       3000
             *        *          *          *          *
TGTTAATGTT GATGTGTGTG TATGCAGAAC CAACTTATGT ACGAGTCCAT
             *        *          *          *          *
CAATGAGCTC CAAAAAAAGG TATGTAAAAC CCCTATCAAA TGTATGTCTT
        3060
             *        *          *          *          *
ATAGAGAAAC GTATAGGAAA GCTAATTAAC AATCGTGCCG TTTCGGAATG
                3120
             *        *          *          *          *
ACAGGAGAAG GCCATACAGG AGCAAAACAG CATGCTTTCT AAACAGGAAC
                          3180
             *        *          *          *          *
ACATGTCATC ATTTCTCTTT CATCAACATG TTGTCCATTG CATTACTGTT
                                            3240
             *        *          *          *          *
ACCTTCCACT GTTCTGCTCC ACACTTCCAG CCAAGCTATA CCTACGATAT
                                                       3300
             *        *          *          *          *
CTTCATATCT CCACTTAACT TCGGCACCAT TAAATAAAAA TAGAAAATCT
```

FIG. 10D

```
          *          *          *          *          *
       TTGCAAATTT GTTTGAAATA GCATAGATGT TGTCTATTGA TTGATATAAT
        3360
          *          *          *          *          *
       CACCAGCCTG TACGTAGATA TGGTTTGTCC GTTTAGTTTT AAGGTGTCTC
                    3420
          *          *          *          *          *
       TCGGATTGAA AATATTTTGA AATCTTTTGA AATGTTTGTC CCATCATTCT
                               3480
          *          *          *          *          *
       TACTTAGCTC ATATCTATGT ATATGAATAT AGACACTACT CCTAATTATA
                                          3540
          *          *          *          *          *
       AAATGTTATA ATAGTTCATT GCATGAGTGC AACTGTGAAA ATAACTATTT
                                                     3600
          *          *          *          *          *
       GTAACCATTG CATATATATA GTTTCTTCAC TTTGAAAATT GATGATGATA
          *          *          *          *          *
       ATATGGTTTG AAATAAATTT GCTGGCAGAT CAAGGAGAGG GAAAAAATTC
        3660
          *          *          *          *          *
       TTAGGGCTCA ACAGGAGCAG TGGGATCAGC AGAACCAAGG CCACAATATG
                    3720
          *          *          *          *          *
       CCTCCCCCTC TGCCACCGCA GCAGCACCAA ATCCAGCATC CTTACATGCT
                               3780
          *          *          *          *          *
       CTCTCATCAG CCATCTCCTT TTCTCAACAT GGGGTAACAA AAAATTACTA
                                          3840
          *          *          *          *          *
       ATCAGTCTTA ATTTAAAGCA CATATGTTAT GCAAGCTAGT TACGTTAGGT
                                                     3900
          *          *          *          *          *
       GTTGTAATTT CATTGAAGTT ATAGCTGTTA GTGATGGTTA CATGATGCTA
          *          *          *          *          *
       GATTTTGAAA CTAGAAAACT TTATTTTAAA ACATTATTTT ATTAACGTAG
        3960
          *          *          *          *          *
       GTTAATGCAA TGGTCGCCAA ACGAACAAAC TTATTAGTGT GGAAAAATGT
                    4020
          *          *          *          *          *
       ACATGGAATG GTTGCGAAAA GCCTAAGTCG ACTTTTGTTG TTGTTGGTCT
                               4080
          *          *          *          *          *
       ATGTGTTTAA GTACAATTTT AGTTTGTTAG ATAAATGAAA TTAATATATC
                                          4140
                            FIG. 10E
```

```
             *          *          *          *          *
      TTTGACATTT CACAATGGAC TGATATTTGA TTTTCCTTTG TTGTACGGTG
                                                       4200
             *          *          *          *          *
      AAACATATGA TTACATATGC ACTTTCATAT ATATCCTATG TATGATTGTG

*          *          *          *          *
      AATGCAGTGG TCTGTATCAA GAAGATGATC CAATGGCAAT GAGGAGGAAT
           4260
             *          *          *          *          *
      GATCTCGAAC TGACTCTTGA ACCCGTTTAC AACTGCAACC TTGGCCGTTC
                      4320
             *          *          *          *          *
      GCCGCATGAA GCATTTCCAT ATATATATAT TTGTAATCGT CAACAATAAA

*          *
      AACTAGTTTG CCATCATACA TATAAATAG
```

FIG. 10F

```
            *          *          *          *          *
     GCACCTGAGT CCGACTCCAA TGTAAACCAA TTTCTCTCCA TTAACTTATA
             60
              *          *          *          *          *
     TAAATTAAAT ATTATTTCAG TATTAGTGAT ATATACTTAT CTGTATTAAA
                       120
              *          *          *          *          *
     CTTGTGAGAT ATAGACGAAC TGGTCGATGG AGTATAATAG GCTTAAGGCT
                                  180
              *          *          *          *          *
     AAGATTGAGC TTTTGGAGAG AAACCAGAGG TACATTTTCA TTCATCATTT
                                             240
              *          *          *          *          *
     ATATTAATAG ATGAAATATC AAACAGGATT AATGTTAGTT AAAAATGCAT
                                                        300
              *          *          *          *          *
     GATTACTTAT AAGAAAATGA TGCATTTAAA TAACAAAAAA ATGCATCGAT
              *          *          *          *          *
     GCTCTATTGA AATTTAGGCA CTATCTTGGG GAAGACTTGC AAGCAATGAG
             360
              *          *          *          *          *
     CCCTAAGGAA CTCCAGAATC TAGAGCAACA GCTTGATACT GCTCTTAAGC
                       420
              *          *          *          *          *
     ACATCCGCTC TAGAAAAGTA TGAATCCTCC TATTTCTTTA ATTAACATGT
                                  480
              *          *          *          *          *
     ATACAACTTA AACACATATT ATTTTATTAT TCAATACATA TATATGAATA
                                             540
              *          *          *          *          *
     GTACATATGT GATTTTATTG GTTGGATATA AAAGATCAAT CACGTCGATT
                                                        600
              *          *          *          *          *
     AGATGTATGA CTTTTTAAAG AATTAGTATA TAGAGTATGA TTAGTCAATG
              *          *          *          *          *
     TAATGGTACG TACGTTTATG CAGAACCAAC TTATGTACGA CTCCATCAAT
             660
              *          *          *          *          *
     GAGCTCCAAA GAAAGGTATG TATAAACCCT ATCAAATTGA CGTTTACATA
                       720
              *          *          *          *          *
     GAATAACTGC GTGTAAGAAT CCTATAGGGG AGCTAACAAT CGTGCCGTTT
                                  780
              *          *          *          *          *
     TGGAAATGAC AGGAGAAAGC CATACAGGAA CAAAACAGCA TGCTTTCCAA
                                             840
              *          *          *          *          *
```

FIG. IIA

```
GCAGGTGCCA TTTGTCATTA TTTTTATATC GTCAAAATGT TTTCTATTGT
                                                   900
              *          *          *          *    *
AGTACTGTTA GCTTCCACTG TTCTACTCCA CACTTCAAGC CAAGCTATAC

*          *          *          *          *
CTACCTACGA CTACGAGATT CTCCACATAT TTCTCCACTT AGCTTCGGCA

960
     *          *          *          *          *
CCACTATAAC TAAAATATAG ATAAAATATC ATTTTTATAG TCTATGATTG

1020
     *          *          *          *          *
ATATACTCGT CAGCCAGTAC GTAGTTGGGT ATTTGCCCGT TTAGTTTTAA

1080
     *          *          *          *          *
GGTTCTTTTC CGGATTGAAA ATATTT---- -ACCCTACCT TTGATGCTAT

1140
     *          *          *          *          *
TATATGTATA TCTATTTAGA AGTCGTGGCT TTGAAAATTG ATGATGATAT

1200
     *          *          *          *          *
GTATGGTATA AGTTGGTAAC AAACTGGTGT GTGAAATTGA AACTTGTCAG

*          *          *          *          *
ATTAAGGAGA GGGAAAACGT TCTTAGGGCG CAACAAGAGC AATGGGACGA

1260
     *          *          *          *          *
GCAGAACCAT GGCCATATAT GCCTCCGCCT CCACCCCCGC AGCAGCATCA

1320
     *          *          *          *          *
AATCCAGCAT CCTTACATGC TCTCTCATCA GCCATCTCCT TTTCTCAACA

1380
     *          *          *          *          *
TGGGGTAGTT AAAAATTCGT TCCTCTTACT TTCAAGTCAT ATGTGTATAT

1440
     *          *          *          *          *
ATACAAGATA GTTAGGTGTT ATAAGTCCAG TGAGTTAGGT TGTGTTAGTG

1500
     *          *          *          *          *
ATGGTTAGAT GTCTAGATTG TGAATTACAA GTACTAAGAT TTTTCAGTTA

*          *          *          *          *
TATAATTAAC GTATTGATCA TCAATCAAAT GGTCGTAAAA AAACAGACTT

1560
     *          *          *          *          *
ATATTTTTGG GAAAGTAGAT GGAATGGCTG CTAAAAGTCT AAGAAACCTT

1620
     *          *          *          *          *
TGGGAGCAGG TCGTATTTAT TGTTGTTCAA ATTAAACTTG AGGTAGTTAG
```

FIG. 11B

```
                         1680
     *         *          *          *          *
ATAAATAAAC TATCTTTGAT ATGGCCTTTA CCAATTTCAC TACAAAACAT
                                    1740
     *         *          *          *          *
GTGATATTTT CAGCACCTAT GTAGATAATT TGTAAGCTAT ATCATGTGCA
                                               1800
     *         *          *          *          *
TATGAATGTA AATGCAGGGG GCTGTATCAA GAAGAAGATC AAATGGCAAT

*         *          *          *          *
GAGGAGGAAC GATCTCGATC TGTCTCTTGA ACCCGGTTAC AACTGCAACC

1860
     *
TTGGCCGTCG CCGCT
```

FIG. IIC

```
         *          *          *          *          *
GAGCTCTTCT TTATATCTCT TCTTGTAGTT TCTTGTTTCG TTTGGTTCTC
        60
         *          *          *          *          *
TTAGAGGAAA TAGTTCCTTT AAAAGGGATA AAAATGGGAA GGGGTAGGGT
                   120
         *          *          *          *          *
TCAGTTGAAG AGGATAGAAA ACAAGATCAA TAGACAAGTG ACATTCTCGA
                              180
         *          *          *          *          *
AAAGAAGAGC TGGTCTTATG AAGAAAGCTC ATGAGATCTC TGTTCTGTGT
                                        240
         *          *          *          *          *
GATGCTGAAG TTGCGCTTGT TGTCTTCTCC CATAAGGGGA AACTCTTTGA
                                                  300
         *          *          *          *          *
ATACCCCACT GATTCTTGGT AACTTTCTCA TTTAAGAAAC AAAA---TAC
         *          *          *          *          *
CCTAAGATTG TATTTTACAT GATCATTTAC TTGTTTTACA CAGTATATAC
        360
         *          *          *          *          *
TCTATGTATA TAATATGATC ATAAATTGTT GATGATAAGA AGCTAGCCCT
                   420
         *          *          *          *          *
AATTCTGTGA ATTGAACAGT ATGGAGGAGA TACTTGAACG CTATGAGAGA
                              480
         *          *          *          *          *
TACTCTTACG CCGAGAGACA GCTTATAGCA CCTGAGTCCG ACTCCAATGT
                                        540
         *          *          *          *          *
AAACCAATTT CTCTCCATTA ACTTATATAA ATTAAATATT ATTTCAGTAT
                                                  600
         *          *          *          *          *
TAGTGATATA TACTTATCTG TATTAAACTT GTGAGATATA GACGAACTGG
         *          *          *          *          *
TCGATGGAGT ATAATAGGCT TAAGGCTAAG ATTGAGCTTT TGGAGAGAAA
        660
         *          *          *          *          *
CCAGAGGTAC ATTTTCATTC ATCATTTATA TATATGATGA AATATCAAAC
                   720
         *          *          *          *          *
AGGATTAATG TTAGTTAAAA ATGCATGATT ACTTATAAAA AAATGATGCA
                              780
         *          *          *          *          *
TTTAAATAAC AAAAAAATGC ATCGATGCTC TATTGAAATT TAGGCACTAT
                                        840
         *          *          *          *          *
```

FIG. 12A

```
CTTGGGGAAG ACTTGCAAGC AATGAGCCCT AAGGAACTCC AGAATCTAGA
                                                   900
           *          *          *          *     *
GCAACAGCTT GATACTGCTC TTAAGCACAT CCGCTCTAGA AAAGTATGAA

*          *          *          *          *
TCCTCCTATT TCTTTAATTA ACATGTATAC AACTTAAACA CATATTATTT
      960
      *    *          *          *          *
TATTATTCAA ATACATATAT ATAAATAGTA CATATGTGAT TTTATTGGTT
                1020
           *    *          *          *          *
GGATTTGAAA AGATCAATCA CGTCGATTAG AATGTATGAC TTTTTAAAGA
                     1080
           *          *          *          *          *
ATTAGTATAT AGAGTATGAT TAGTCAATGT AATGGATCGT TTATGCAGAA
                                1140
           *          *          *    *          *
CCAACTTATG TACGACTCCA TCAATGAGCT CCAAAGAAAG GTATGTATAA
                                           1200
           *          *          *          *
ACCCTATCAA ATTGACGTTT ACATAGAATA ACTGCGTGTA AGAATCCTAT

*          *          *          *          *
AGGGGAGCTA AAAATCGTGC CGTTTTGGAA ATGACAGGAG AAAGCCATAC
      1260
      *    *          *          *          *
AGGAACAAAA CAGCATGCTT TCCAAGCAGG TGCCATTTGT CATTATTTTT
                1320
           *    *          *          *          *
ATTTCGTCAA AATGTTTTCT ATTGTAGATC TGTTAGCTTC CACTGTTCTC
                     1380
           *          *    *          *          *
ACCACACTTC AAGCCAAGCT ATACCTACCT ACGACTAC-- -CCTACATTT
                                           1440
           *          *          *          *    *
GATGCTATTT ATATGTATAT CTATTTAGAA GTCGTGGCTT TGAAAATTGA
                                                   1500
           *          *          *          *     *
TGATGATATG GTATGGTATA AGTTGGTAAC AAACTGGTGT GTGAAATTGA

*          *          *          *          *
AACTTGTCAG ATTAAGGAGA GGGAAAACGT TCTTAGGGCG CAACAAGAGC
      1560
      *    *          *          *          *
AATGGGACGA GCAGAACCAT GGCCATAATA TGCCTCCGCC TCCACCCCCG
                1620
           *    *          *          *          *
CAGCAGCATC AAATCCAGCA TCCTTACATG CTCTCTCATC AGCCATCTCC
```

FIG. 12B

```
                                    1680
         *          *            *            *           *
   TTTTCTCAAC  ATGGGGTAGT  TAAAAATTCG  TTCCTCTTAC  TTTCAAGTAC
                                              1740
         *          *            *            *           *
   ATATGTGTTA  TATATACAAG  ATAGTTAGGT  GTTATAAGTC  CAGTGAGTTA
                                                        1800
         *          *            *            *           *
   AGTTGTGTTA  GTGATGGTTA  GATGTCTAAA  TTGTGAAATA  CAAGTACTAA

*          *            *            *           *
   GATTTTTCAT  GTATATATTT  AAACGTATTA  ATCATCAATC  AAATGGTCGT

1860
       *          *            *            *           *
   AAAAGAAACA  GACTTATATT  TTTGGGAAAA  GTAGATGGAA  TGGCTGCTAA

1920
         *          *            *            *           *
   AAGTCTAAGA  AACCTTTGGG  AGCAGGTCGT  TTTTATTGTT  GTTCAAATTA

1980
         *          *            *            *           *
   AACTTGAGGT  AGTTAGATAA  ATAAACTATC  TTTGATATGG  GCCTTTACCA

2040
         *          *            *            *           *
   ATTTCACTAC  AAAACATGTG  ATATTTTCAG  CACCTATGTA  GATAATTTTG

2100
         *          *            *            *           *
   TAAGCTATAT  CATGTGCATA  TGAATGTAAA  TGTAGAGGGC  TGTATCAAGA

*          *            *            *           *
   AGAAGATCAA  ATGGCAATGA  GGAGGAACGA  TCTCGATCTG  TCTCTTGAAC

2160
       *          *            *
   CCGTTTACAA  CTGCAACCTT  GGCCGTCGCT  GCTGA
```

FIG. 12C

```
GGATCCCTCC GGAAGCCTTA GATCAATGGT AGTTGTGGTT ATTTTAAGAT
    60
CAGATTCTTT TGGAAATCCA GTAACATAGT CTGGGAATAT GATTTGCTTG
          120
TTGGTCACCG TTACTGCTTC TGCGTTCGTC ATTTCCGATT TTACGTACTT
               180
TTGATCACTA TGATAATTTC TTCTTTCTTA CGTCGAGATG TGTCTGCTTT
                         240
TTGTAGATTG AATTTCTCAA TGTTGCTTTG ATCATAAGAC CATTTGATTT
                                   300
CTTTCCTTCA TTGATCGATC CAATTTCTTC GGGAGATAAA TAAGGTAAAA

ATGGACTATT ATTTTTGGAA AATACAGGAG AAAAAAATTC TTAAGAATAA
   360
AAGAGTATTT ATAGTGACCA TGAATTTTGT TGTTTTTTTA AAAAGAAAAA
         420
AAAACTCGAT TGGATTGGAT GACACATTGA AATTAACATT CAAATAGCAT
                    480
CTTAGTTAAC AGATATTGCA TGCACCATAT AATAAAATAT CATAATTATG
                              540
TGTGATGCGA GGTTTGTTTT GGTCAAAATG TTATTTTAAT CACAATTTAA
                                        600
TAACAGATCA TTTACCAATT TGTTTTTTGA TAATTTATGC CAACTTAGTA

AATTCATCCA AAAAGTTGAA AAATATAGAT GTGTAATATG TTGACGGATA
  660
TACAACACTC AAAACAATAT ACTCAAAAAA AAAAAAAATT GAAAGCGGCA
            720
ACGATTCAAA CATATATGCT AAATTTTAAT AATGGACAAA GGAGGAAGTA
                        780
CTGCATATGT ACGAAAAGTG TTGATAATGG AGAGCAGCGG ATAGTGTCGC
                                  840
```

FIG. 13A

```
CAAGGGCACG AGCTTTAGAT TCTTTTAGTT TGCTCTAAAT GTTCTTCTTT
                                                     900
     *          *          *          *          *
GGTACTTTTA ATTGCTTTAG TTGCTTGCTT CTTATCTCCA CATAAATAAA

*          *          *          *          *
TGGGGTAACC ATTTTCTCTC GTATCTTATT CCGATCTTTG GATCTATGTA
     960
      *         *          *          *          *
CGTACTACAT GAATAAATCG TGTTCAATAA GTTATTATCA TTTGGTCTGC
                1020
      *          *         *          *          *
TTAAAGTGAT CATGGTGTAT TAATCTATAA TACGTAGTTC TCTTAATTTA
                           1080
      *          *          *         *          *
TTCCCTAGAA TTCCATCAAA GACAAATTTT AGCAAAAAGA AAAGTTGAGT
                                     1140
      *          *          *          *         *
ATATAATTTG CTTAGTAGTA CAAAAAAAAA CTTTATGGTA ATTTGTATTT
                                                    1200
      *          *          *          *          *
TGGATATTTC CTTNATTAAC CCAAACTTCA AAATTAATTT TCTTCTGCTG

*          *          *          *          *
TATCTTTATA TCCAACGTGA AATCTATTGA CTCAACAAAA TACACAGTTG
     1260
      *          *          *          *          *
TCAATTGAAG TTCAACTCTA CCAAGAAACA TCTATATGTA CTTCACTGTT
                1320
      *          *          *          *          *
CTTACCGCCG AGCAATTAAA ACCTCTATAA CTACTTGGTT ACATTATTAC
                           1380
      *          *         *          *          *
ATTTTTATTT ACAAAAAATA TATATCAACA ACCAATAATA TAGTTAGAAA
                                     1440
      *          *          *         *          *
ATGAAAGAAA ATTATTTAAG AAATATCCGC CGTCAATGCA AATCGAATGC
                                                    1500
      *          *          *          *         *
GACACTTGGG GAAGCTCTGA AGTCTGTGGT CTGTGCATAT TTCACTTGTC

*          *          *          *          *
TAGCTAACCC ATTTTCACGT CACTAGACGT CGATAATCAA TTATTGTTAT
     1560
      *          *          *          *          *
TTTTTTTATC AATGTTCCAC TTATTGAAAA TTATATACGA GAAAACATAG
                1620
      *          *          *          *          *
ACTCGACATT AGGCAATGGA AGTCTAATCA GACCAATGAG AAGTCGACAA
```

FIG. 13B

```
                            1680
CACATCCTAG AAACCAACTC TGGTTTATTT CCTTCCCTAA TACCAAGTTA

1740
TAGNNTTCTT TCAAACCGCT ATTTCCAAAA TATCTCTTCT TTAAATAAAG

1800
AGTGAAAGAA GCACTCTTTC ACATTACCAT CATTAGAAAA CTTTCCTAAT

TAGATCAAGA TCGTCGTTAT CTCTCTTGTT TTTTCTTCAT ATAATTTAGT

1860
TATTTTAAGA GAAATGGGAA GGGGTAGGGT TGAATTGAAG AGGATAGAGA

1920
ACAAGATCAA TAGACAAGTG ACATTCTCGA AAAGAAGAAC TGGTCTTTTG

1980
AAGAAAGCTC AGGAGATCTC TGTTCTTTGT GATGCCGAGG TTTCCCTTAT

2040
TGTCTTCTCC CATAAGGGCA AATTGTTCGA GTACTCCTCT GAATCTTGGT

2100
AATTGCTTAA TTCCTTCTTT TTTTAATGTT ATTTTTAGTG TGCCTTCGTT

TGCCCTAACT AGTAGTCTTT GTTCTACTTA AGGCATATTT TCTGTGTCTT

2160
CTATGCTATT ATCTGTCTTT GCTGAAAATT TGCCACTGAT TTGGTATCTA

2220
TTTACTTGGG ATCTACGAAC TGATTGTGTT GGTCATATCA TTAGTTTATT

2280
TTTATCAATA ATTTATTATA TATCAAAGAA AATGAAATTT TTTAGGACTT

2340
TTAGTGAACC CTACAATACG ATCTACTTAA TTATAGTGGC ATGGATTTGT

2400
AAGAAATCTT CAGCATCTTC TTTAATCTGG AAATGTACAT TTTGCTTCAA

GTCAAGTTTA GTATATTAGG TACAGAAAGA ACGGATGTTT ATGGTCTAGA

```
CTAGGGTTTT TGCTTTTAGG AAAGCTATAC TTTTGCTTAA ATATCTTTAA
           2520
GTTGCATTTT ATGAACACAC ACACACATAT ATATATATAT ATATTAGTAT
                      2580
ACCAATAATC TTAATTAAGT TTAGAAAGAA ACTCTTCATT TTTTCCCATT
                                 2640
TAATAATGGT TTATAGCTAG GTATAGAGAA ACTGGAAATA AGTATGTGAC
                                            2700
ATCTAAGTAT GGGGAGTCTT TGACCTCTGG GGATTAATGT AAAACAGATC

GTTCTTTTTT TTCTAAACAG TTCCTCCGTA CTGATGGTCA AACTTAACTT
2760
CAACAGTTCC TTTTAAACTT TTATAGGGTG CTTGAATACG TCTTGGGGTG
           2820
TGGGGTTAGT GGCTCAACTG GTTTATTTAT TTTTAAAAAT GGTAGAAATC
                      2880
AGTACTGTTT CTAGCTAGGG TTTAGGCACA AAACTAGAGA TCATCTTTAT
                                 2940
TCCATAATAG AAAGGAAGAA ACTAATGTTT AATGACATAG ATTAATTAGA
                                            3000
TAACCCTACA TAATCAGATG CTATATGTTA TCACATATTT TGGGTGAATC

GTTAATTACG TTTGAAACAA GTGGCCTCTT GTGCTAGCTG ATAAGATAGT
3060
TGNGTATGCA ATTATATTGG TGGTTGAATC CAAACTAATT CTAACTCGTA
           3120
AGCTTAATAT TTGTAGCATG GAGAAGGTAC TAGAACGCTA CGAGAGGTAT
                      3180
TCTTACGCCG AGAGACAGCT GATTGCACCT GACTCTCACG TTAATGTATG
                                 3240
TTTAATGGTC TCCATCATAT ATTTGTGTAT ATTTTGAATC TTGCATGTGT
                                            3300
TTTAACATAG CATATAACTG ATTATTGGCT TTCATGTTGG AAATTAATTG
```

FIG. 13D

```
                *          *          *          *          *
         TGAAGGCACA GACGAACTGG TCAATGGAGT ATAGCAGGCT TAAGGCCAAG
              3360
                *          *          *          *          *
         ATTGAGCTTT TGGAGAGAAA CCAAAGGTAC ATAGTACATT TAAATTTATT
                        3420
                *          *          *          *          *
         GTAGTAGTTA AATATTGAGG AATAACAGAA GAGAGAATGT TCTTAATTAA
                                  3480
                *          *          *          *          *
         CTAAATCATC ATAGGCATTA TCTGGGAGAA GAGTTGGAAC CAATGAGCCT
                                             3540
                *          *          *          *          *
         CAAGGATCTC CAAAATCTGG AGCAGCAGCT TGAGACTGCT CTTAAGCACA
                                                        3600
                *          *          *          *          *
         TTCGCTCCAG AAAAGTGTGT AAATATATCC CACACTCTAT CTCTATGCAT
                *          *          *          *          *
         AACTAACTTT GACTTTGTGT GGATGTATTA CATATAGTCA AATATTGTAT
              3660
                *          *          *          *          *
         AGAGATTGTC TCATATAAAT AAATAATTTT TGGCCTTTTT GTATGCAGAA
                        3720
                *          *          *          *          *
         TCAACTCATG AATGAGTCCC TCAACCACCT CCAAAGAAAG GTAGCTAAGT
                                  3780
                *          *          *          *          *
         TAAAACCATT TTATCTCTCA AGTCCTGTGT GTATAGAGTC ATGACTTATA
                                             3840
                *          *          *          *          *
         TGTTAGAGAT ATAAATCTTT TAATAAATAA ATAACATATA GGTTATATAT
                                                        3900
                *          *          *          *          *
         AATTCAGGTT AATATATTAT TAATTACTAG ATGTATATAT ACTTATATAG
                *          *          *          *          *
         ATCATATAAA AAGAGAAATT GACAATGGTG TCATTTTTGT GGAAATGACA
              3960
                *          *          *          *          *
         GGAGAAGGAG ATACAGGAGG AAAACAGCAT GCTTACCAAA CAGGTGATCA
                        4020
                *          *          *          *          *
         TTGTTTTTTG CATTTCTAAC TGTTTCACTA TTTACAATTC CACTGTTGAA
                                  4080
                *          *          *          *          *
         CTCCACTTCA ATCTCTACCT TAACGTACCA TCTCTCCACT TTCGGCCCCA
                                             4140
```

FIG. 13E

```
ACTCTTTTGA GTAAAAAGAA TTGATATGTA GTTTCTTTTG ATTGGTATAA
                                                    4200
TCATGAGCCT AGCTGCACGT ATAGGTAAGC TTTGTCCGTT TAGTATTAAG

GTTGTCTCCC AGATTTGAAC TTGAACTTGA ACTGTCTTCT CATAATCATA
     4260
GTCTATGTGT AAATTACACA TACATTAGCT AGATAGCTAG GAGCTATATT
                4320
TTAAGTTTTA TTGAGAAGTA AGAAAACGTA CGATGAAACT ACTTGATTAA
                          4380
GAACATATAT TAAATGAAAA AATATCACAA TAGTAAGACC TTGACGACGC
                                         4440
TAAAATTCGC TTAACATTTT GCAGATTTAA TTATTACTTT GCATTTTGTT
                                                    4500
TGAAAATATC ATATTACAAA AAAAAGTATA AGAATAAAAA ATTGAAGTTC

CTTGAATAAA TGCAAATAGC TGATTAGTTG CAAATGGGAA TCTATATAAC
     4560
GATGATGCTT ATATCATTTT CTTGGCGTGT GTAATCGGTA TAGATAAAGG
                4620
AGAGGGAAAA CATCCTAAAG ACAAAACAAA CCCAATGTGA GCAGCTGAAC
                          4680
CGCAGCGTCG ACGATGTACC ACAGCCACAA CCATTTCAAC ACCCCCATCT
                                         4740
TTACATGATC GCTCATCAGA CTTCTCCTTT CCTAAATATG GGGTAACGGC
                                                    4800
AGTATTTCTT ATTTTTTTAA GTTCTTTTTT CTTACCATAA TGTCAAATTC

TCATATATAG TGAAGTGTTG TCAGTCAGTC ATATAGGCAA TGATAGTGAA
     4860
TGCACTTCAT ATATAGGGTT TGTGTTAGGT ATGGCGTTAG AGGTTGATGG
                4920
TATGCATGCA TATTATTGTA TTATGATTTT TAATTTGCTA TATATGATTG
```

FIG. 13F

```
                                  4980
    *           *           *           *           *
TAATTTCAGT  GGTTTGTACC  AAGGAGAAGA  CCAAACGGCG  ATGAGGAGGA

5040
    *           *           *           *           *
ACAATCTGGA  TCTGACTCTT  GAACCCATTT  ACAATTACCT  TGGCTGTTAC

5100
    *           *           *           *           *
GCCGCTTGAA  TAGACTACAT  CGATCTATAT  CAATCTCTTT  AAAATAATAT

*           *           *           *           *
AAGATCGATC  CTCTATTCAT  GATCTATATT  AAACACCGGT  TAATTAATAT

5160
    *           *           *           *           *
ATTTTTGGTA  TGTCCTTATA  TCATATCAAC  ATCATCAAGC  CTTTTTCCAA

5220
    *           *           *           *           *
TTCAATATAT  CTTGTATTTC  GGGGAGCAAT  GAATAAATGT  AATATTTGTG

5280
    *           *           *           *           *
GACTGAGAGA  GCTAGAAAGA  ATTGTTGTTC  AAACCTTTTC  TATATTGATC

5340
    *           *           *           *           *
TCATCGTTAC  ATTGTAATTT  GATTTCTTTC  ACACCCCAAA  ATATTTGTAA

5400
    *           *           *           *           *
TACGAATTTA  GTCTTTGATG  ATTTGAACTT  TACTTGGTCA  AAGTAAATCA

*           *           *           *           *
CAGCCTTAGA  AGGTAAATTT  TGAATTGAAA  ATAGAAATAA  AAATGTTGGG

5460
    *           *           *           *           *
AACGTGACAT  TCGGTTTCTT  CTCCATTTGC  TTCATGTAGG  TGCGTGATAC

5520
    *           *           *           *           *
GATCGGAAAT  GAGAATTATT  GGGCCCTTGT  GGGCTTCATA  ATTATTAGTT

5580
    *           *           *           *           *
CATTGTTTAA  GCCCATAATA  CTTGGCATTT  TTGCCAAAGA  AGAAACTGTA

5640
    *           *           *           *           *
TAAAAGAAAT  CGGAGAAGAA  AAGAAAAATA  GTAGTCGCGG  CAATGGAGGA

5700
    *           *           *           *           *
TCTATGGAAG  AGGGCAAAAT  CGTTCGCAGA  AGAAGCGGGT  AAGAAGTCTC

*           *           *           *           *
AGACGATAAC  ACAATCATCC  TCCGCGACCT  TCGTCAATCT  CGTCACCGAG
    5760
```

FIG. 13G

```
          *         *         *         *         *
TCTAGATAAT CTTCTCAAGA AGGATTTAGA ATGGCATAAT CCAAAGGCTC
     60
      *         *         *         *         *
AAATCTCGGC ATCTGAAACC ATATTATCAA TTTATTCATG ATTTAGGATG
              120
                *         *         *         *
CAACCAATTA AAAATAATCA GTGCATATGA TTTCATAAGT CTCTCGACCA
                        180
      *         *         *         *         *
AAACACTTTA CTACTCGATC ATGGTGCGAA ACAAGTCGAG AATGCTAGGT
                                  240
      *         *         *         *         *
CTATATGTGA TGCTTAGGCC ACACGGCATG TAATGTGATA CAACGATCCT
                                            300
      *         *         *         *         *
AGAGATCGGT TCTGAGATAT GCAAGCAAGG TCACACGACC ATTCATATAT

*         *         *         *         *
GGTGTCTCTC TAGGCCACAC GGCAAGCTAT GATGCATTAA GCCACACGGC
    360
      *         *         *         *         *
TTTCAATCAC ATGATGCAAC AATGTGATCT ATCAAGGG-- ---CTCGAGC
              420
      *         *         *         *         *
TGCACACAGA CGGACGCGAG CTGGCTGTCG TCGGATGCGA GCTGAACGGG
                        480
      *         *         *         *         *
ACGGGACTCG TCTGCTTCCT ATCGGGTTCG CGAGCTGCTT CCTATCGGGT
                                  540
      *         *         *         *         *
TTTCAAGCGG CTGATCGGGA TTACAAGCTG GTTGATCAGG AACACGAGCT
                                            600
      *         *         *         *         *
GGCTGTGATG CGAACGGAAG CTGAGGTTGT CTAGGATCAG GAACACCTTA

*         *         *         *         *
GGGATGGAGC TGATCGGTTG CTGACGAGCT GGAACGCGAG CTAGGACGAA
    660
      *         *         *         *         *
TTAGGGTTCG TCGGGATTAG GTTAAAGTCG CCGGCTAGGT TAGGTTTAAG
              720
      *         *         *         *         *
GGATTGGCGA TTTTAGCTTA GATTGCAGAG AACAATCGTG CTGATAACAT
                        780
      *         *         *         *         *
GTTGTAATTA GAAGATTGAA GATTGAATAG TTCTGTGTTT TATTAACATA
                                  840
      *         *         *         *         *
```

FIG. 14A

```
ACATGAATT- ----AAAGAT TCCACGAGTT TCGTACATGT TCTATTGCTA
                                                   900
         *          *          *          *         *
GTTAGGTTAA GGGAGTTAAG CAAAGTAGAG TGATTGGCAT TAACTCTTCA

*          *          *          *         *
GTAGTGCCCA CGAAGACTCT AGTTAGAAGT CAGTTCAATC TGACAAGCTG
      960
         *          *          *          *         *
TTAGAGGTTC ACTAACACTT GAGTTTGGAT CTTGAAGGTC CATATAATAG
               1020
         *          *          *          *         *
TATAACGTAG ACCCAATATA ATACAAAACT ATAGTATTGA CTATAAATTT
                          1080
         *          *          *          *         *
GAGTGTCTAC ACCAACTCGT TTAAGCAAGA CAGGTCCCGA GACCGGAGTG

*          *
GTTTCTTTGT TGAGCTC---
```

FIG. 14B

```
                *          *          *          *          *
       AAGCTTTAGG GTTTTAGGGT TTTTGATTCC AAGATTTAGG GTTTTCATAA
                60
                *          *          *          *          *
       TTCAGATCAG AACAATCAAT CAACATGTTC TAATGGAATC GATTTCAATC
                          120
                *          *          *          *          *
       TAGTGATTAT AAGATGATCA GTTTTAGGTT ATACCAATTT TTAGGATTTA
                                      180
                *          *          *          *          *
       TCAAGATCAT TGGATTTCCA TAATAATGGA TTAGGGTTTT AGGGTTTGAT
                                                 240
                *          *          *          *          *
       CATTATGTTT TTAGATTAAT CGGTATACTT TTGTTTGTAG GGTTGAAACC
                                                           300
                *          *          *          *          *
       GGACCACCAA AGAGAACGGA TGAACCTCGA GCTGCACACC GACAGATGCG
                *          *          *          *          *
       AGCTGGCTGT CGTCGGATGC GAGCTGAACG GGACGGGACG CGTCTGCTTC
                360
                *          *          *          *          *
       CTATCGGGTT CGCGAGCTGC TTCCTATCGG GTTTGCAAGC GGCTGATCGG
                          420
                *          *          *          *          *
       GATTGCGAGC TGGTTGATCG GGAACACGAG CTGGCTGTGA TGCGAACGGA
                                      480
                *          *          *          *          *
       AGCTGAGGTC GTCTAGGATC AGGAACACCT TAGGGATGGA GCTGATCGGT
                                                 540
                *          *          *          *          *
       TGCTGACGAG CTGGAACGCG AGCTAGGACA AATTAGGGTT CGTCGGGATT
                                                           600
                *          *          *          *          *
       AGGTTAAAGT CGCCGGCTAG GTTAGGTTTA AGGGATTGGC GATTTTAGCT
                *          *          *          *          *
       TAGATTGCAG AGAACAATCG TGCTGATAAC GTGTTGTAAA ACAAACGGTT
                660
                *          *          *          *          *
       TTAGAAACTG AATGTTTATG TGTATTATTA ATCATAATAT GGGTTTTTT-
                          720
                *          *          *          *          *
       ---------T ACAGTGCGAG AATGATAGAC TCGCATAGCC AATGAAGTCC
                                      780
                *          *          *          *          *
       AGTCAGACCA ATGAGAAGTC GACAGCAAAA CCTAGTAAAC TACTCTTGTT
                                                 840
                *          *          *          *          *
```

FIG. 15A

```
TTATCCTTGT CCAAAACCAG CTTTAGGTTT CCCTGAAACC GCTTATTCCA
                                                    900
         *          *          *          *          *
AAACATCTTC TCCTTAAATA AAGAAAGACT CTTTCACATT GTTATTATCA
         *          *          *          *          *
TCAGAAGGGA AAGAAGAAAA ACTTTCCTAA TTAGATCGAG CTTGTCGTTA
    960
     *          *          *          *          *
TCTCTCTATT ATAGTTTATA TTTCTTACTG GGGCTTGTTT GGTTGCTTCT
              1020
     *          *          *          *          *
CTTTTTGGAC TTCTTTTATA TAATTTATAT ATTCTACGAG AAATGGGAAG
                        1080
     *          *          *          *          *
GGGTAGGGTT GAAATGAAGA GGATAGAGAA CAAGATCAAC AGACAAGTGA
                                  1140
     *          *          *          *          *
CGTTTTCGAA AAGAAGAGCT GGTCTTTTGA AGAAAGCCCA TGAGATCTCG
                                                    1200
     *          *          *          *          *
ATTCTTTGTG ATGCTGAGGT TTCCCTTATT GTCTTCTCCC ATAAGGGGAA
     *          *          *          *          *
ACTGTTCGAG TACTCGTCTG AATCTTGGTA ACTGCATAAT TCCCTTTTTA
    1260
     *          *          *          *          *
ATTGTTTTAG TGTGCCTTTG TTCGCCCTAA TAAATAGTTT TTGTTCTCCT
              1320
     *          *          *          *          *
TTAGGCCATT TCTTGGTATC TTCTTATGTT TTTATGAAAA TTCTCACAAA
                        1380
     *          *          *          *          *
TTTTGTAGTT AATTACTTGG ATCTACGAAT TGATTTCACC AAAGTGAAAT
                                  1440
     *          *          *          *          *
TAAACCATTA TAGCATATTT GCTTATATCA GAAGAAAATA AAAAAAATAG
                                                    1500
     *          *          *          *          *
GGCATAATAA GGTGTTATGT GAAGTGAAAG TTTACTTCAG GTAACACGTT
     *          *          *          *          *
ATTAAGATAT GCTTAACCCT AGATCAAGAT CTACTTCTAC TGGTCGCGAC
    1560
     *          *          *          *          *
ATGGATTTAC AAGAAATCGT CACTGTATAT GAACTTTAAT TTAAACATGT
              1620
     *          *          *          *          *
ATAGACCTTT TTGTTTCAAA TAGAGAGTTA AGTAATTTAA TCATAGAAAG
```

FIG. 15B

```
                                 1680
            *          *          *          *          *
        AACCAACGTT ATGTTCATCT AGGCTAGAGT GATTTTTGCC TAACAATTTT
                                            1740
            *          *          *          *          *
        GAAAAGCTGT CCTTATGCTT AAATATCTTT CAGCAGCATA GTAGTATGAA
                                                      1800
            *          *          *          *          *
        AGAAAATATT TCAATATCGT TGTATAAAGG TTCTATAATT TTCGTTTTTT

*          *          *          *          *
        TTTTTTTCGC AAATGGTTTA TATAGAGAAA CTAGAACTAG GGATGTGACA
                1860
            *          *          *          *          *
        TCTAGGTATA GGGGTCTTTG ACCTCTGGGA TCAATGTAAA AGAGACCATT
                      1920
            *          *          *          *          *
        CTATTTTCTA TCAACTTCTC AGTTTCCGAT GGTCAAAACT TAACTTCAAC
                                 1980
            *          *          *          *          *
        AACTGTTTTT CTTTTCAGAA GAGGACAAAC TATTATATGT ATATTATGTT
                                            2040
            *          *          *          *          *
        ATGTCGTTTC ATACATAAAT ATCTAATAAC AAATTTATTT TTAAAAACAT
                                                      2100
            *          *          *          *          *
        ATAACAAAAC TTTATTGAAG AATTGGAAAC TCAAAACGGG GACATATAGG

*          *          *          *          *
        ACGCTGCACG TCTAGAGGTG TGGGGTTAGT GATTCAACGG GTTTTTAATG
                2160
            *          *          *          *          *
        TAGAGAAACT GTAGATGTAA GATTGTTTCT AGGGTTAAGG CACTAAACCA
                      2220
            *          *          *          *          *
        GGGATTATCT CTTTTCCATG ATAAAAGTTA ATGTCTTAAA TGCATCGCTA
                                 2280
            *          *          *          *          *
        ATTAATTAGG CAAACTAGAT GATAGTACGT AGTGTGTGTG TGTGTGTGTA
                                            2340
            *          *          *          *          *
        TTGGATATTT TGGGTTAATA GTTACATCTT AGACAAATGT GTGGTCTTCT
                                                      2400
            *          *          *          *          *
        GATAAGCTGA GAAAATATTT GGGTGCAGAC TCTTAGTGGT AATTAATTAT

*          *          *          *          *
        ATCTAGAAAN NCCCANATAC NAATTTAATA CGGCTACTTT TTGGGTGAAT
                2460
            *          *          *          *          *
```

FIG. 15C

```
           GAATCTACAC TAACCCTAAG CCTAATGATA GCATGGAGAA GGTACTAGAA
                      2520
                        *          *          *          *
           CGCTACGAGA GGTACTCTTA CGCCGAGAAA CAGCTAAAAG CTCCAGACTC
                                 2580
                 *          *       *          *          *
           TCACGTCAAT GTATGTTTAA TGATCTCCAA GACTCTGTCA AACATATATG
                                                 2640
                 *          *          *       *          *
           TACTATATCT TGAATGTGTT TTCTTAATTA ACATAATTGA TGCACTGTTT
                                                                2700
                 *          *          *          *          *
           ACATAATGAA AATTAATTGT GTAGGCACAA ACGAACTGGT CAATGGAATA
                 *          *          *          *          *
           TAGCAGGCTT AAGGCTAAGA TTGAGCTTTG GGAGAGGAAC CAAAGGTACT
                 2760
                   *          *          *          *          *
           TATAGAATTT AGGAATTAGC ATGTGTAAAT AATAGTTTAT TGTATTAGTT
                      2820
                        *          *          *          *
           TTTTTTGGTA AAATTATTGT ATTAGTTAAA CACTGGGAAT TAACAAAAAA
                                 2880
                 *          *       *          *          *
           GATGGTGGTA TGGATTAATC ATAGGCATTA TCTGGGAGAA GATTTAGAAT
                                                 2940
                 *          *          *       *          *
           CAATCAGCAT AAAGGAGCTA CAGAATCTGG AGCAGCAGCT TGACACTTCT
                                                                3000
                 *          *          *          *          *
           CTTAAACATA TTCGCTCCAG AAAAGTGTGT AAATAAGCAC ATACAAACGC
                 *          *          *          *          *
           AAACATCTCT ATCTTATCTT TGAGTTTGTG AAGATATATA TGCCTAATTT
                 3060
                   *          *          *          *          *
           TATATAGAGT TTGTCTCATA TGAATGAATA CAATTTGAAC TCAATTGTAT
                      3120
                        *          *          *          *
           GCAGAATCAA CTAATGCACT AGTCCCTCAA CCACCTCCAA AGAAAGGTAC
                                 3180
                 *          *       *          *          *
           GTTAAAACCA TTTCATCTCT CAAGTCGTAC GTGTGTATGT GTGACTTATG
                                                 3240
                 *          *          *       *          *
           TTACCGTTTA AATCTTTCAG TTAAATACAA AACATATGGT TTTACACATG
                                                                3300
                 *          *          *          *          *
           TTAGACTATT TTGGTGAAGG AAACATTGTA AATGTAAACA AAGGGGTTTT
```

FIG. 15D

```
                *          *          *          *          *
           TTGGATTGAA TAAAATTTAA CATTCATTCA AAAAAAACAT ATGGTTCATA
               3360
                *          *          *          *          *
           TATATATTCG GTTTATATGA TTATATATAT ATATTTATAT AGGTTAATAT
                          3420
                *          *          *          *          *
           ATTAGTGTTT AATTATATGT GTATACATAT AGATGTAGAA AGAACCTCTA
                                    3480
                *          *          *          *          *
           GAGCGATCCC TGAGAATTGT TTCATTTTGT AAAATTGACA GGAGAAAGAA
                                               3540
                *          *          *          *          *
           ATACTGGAGG AAAACAGCAT GCTTGCCAAA CAGGTAATCA TTGTATGTTG
                                                          3600
                *          *          *          *          *
           CATTTTTTAC TGTTTCACAA CTGTTTTACT ATTTAAACTC CACTGTTCTA
                *          *          *          *          *
           CTCCACTTCA ACCTTAAACT ACCATTGCTC AACTTTCGGC ACCAACTCTT
               3660
                *          *          *          *          *
           TTTTAAAAAG GAAGAATTAG TTGTTTCATG TGATTGGTAT AATCATGAGC
                          3720
                *          *          *          *          *
           ATATGTGCAC ACATGTAGGT GGGCTTTGTC CGTTTAGTAT TAAGGTTGTC
                                    3780
                *          *          *          *          *
           TCCTAGAATT GAACTTGAAC TGTCTTCTCG TAATCATAGT CTATATATAA
                                               3840
                *          *          *          *          *
           CACGCTGCAC ATACAGTAGC CAGTAGGTTT ATTTGAGCAA GATAC-----
                                                          3900
                *          *          *          *          *
           ---TGCTCTT ACTGTAATAC CGTGCCAACA TTGATTGTGA TTCGATACAT
                *          *          *          *          *
           AAATTTAGTT GATCATAACG TTTATCGGTA TTTGAAATTG GTAGATAAAG
               3960
                *          *          *          *          *
           GAGAGGGAGA GTATCCTAAG GACACATCAA AACCAATCAG AGCAGCAAAA
                          4020
                *          *          *          *          *
           CCGCAGCCAC CATGTAGCTC CTCAGCCGCA ACCGCAGTTA AATCCTTACA
                                    4080
                *          *          *          *          *
           TGGCATCATC TCCTTTCCTA AATATGGGGT AACGGTAGTG TTTCATTTTT
                                                          4140
```

FIG. 15E

```
          *           *           *           *           *
     ATCTTGGTAT  ACATATATAC  ATATAGATCC  GACACTCTTG  GTGTTAGTAA
                                                              4200
          *           *           *           *           *
     TTCAGTGTAT  GCGATGATGT  TGTATGTATG  TATGTTCATA  TTTAGGGTTT

*           *           *           *           *
     GTGTTAAGTG  TGGCGTTAGA  GGTTGATGGC  TTTGTAACTA  CATGTCTAGA
        4260
          *           *           *           *           *
     ACTATACAAT  AATTAATAAG  ATGGAATGAT  ATATATATAT  ACATATATTT
                     4320
          *           *           *           *           *
     TAATTTGCCA  TATGATTGTG  ATTTCAGTGG  CATGTACCAA  GGAGAATATC
                                 4380
          *           *           *           *           *
     CAACGGCGGT  GAGGAGGAAC  CGTCTCGATC  TGACTCTTGA  ACCCATTTAC
                                                 4440
          *           *           *           *           *
     AACTGCAACC  TTGGTTACTT  TGCCGCATGA  ATGGACTCGC  CATATATCGA
                                                              4500
          *           *           *           *           *
     CATAAAATAA  TTTATATAAG  ATCGATTTTT  ACGTATAATA  ATAGGCAGCA

*           *           *           *           *
     ATGGTTAGCC  ACCATATCTA  TATACACTGG  AAATTCTATT  TATC----TT
        4560
          *           *           *           *           *
     ACATTGATTT  ATACTACATA  AACCCTCCAG  ACCAAACTCG  TCTCCATGCC
                     4620
          *           *           *           *           *
     AACTGATAGA  TTTCCTAGAC  ATGCTACACA  CTCCATGACT  CCGACTAATT
                                 4680
          *           *           *           *           *
     TTTGGTTTGG  CGTTTTCTAT  GTTTTTATTA  ATTGTTTTGA  ATTTTACTCT
                                                 4740
          *           *           *           *           *
     TTCACGATAT  TTAAAATTTT  TCAAACTTAT  TTTTGTTGCT  CACAGTGAAC
                                                              4800
          *           *           *           *           *
     AAATCTTCTG  TGAAGAAGTG  GTATATATTC  TGTGGAGCCA  CTTCCCCAAT

*
     GTTCTTTGGT  GGATCC
```

FIG. 15F

```
         T   K   K   I   K   G   I   Q   Q   A   T   A   G   V   S   N   T   S   E   N   P   N   K   T   I   V   P
         ACA AAG AAA AAA ATC AAA GGG ATT CAG CAA GCC ACT GCA GGA GTC TCA CAA GAC ACT TCG GAA AAT CCT AAC AAA ACA ATA GTT CCT 540

A   A   L   P   Q   L   T   P   T   L   V   S   L   L   E   V   I   E   P   E   V   L   Y   A   G   Y   D   S   V
     GCA GCA TTA CCA CAG CTC ACC CTC ACC TTG GTG TCA GTG ATT GAA CCC GAG GTG TTG TAT GCA GGA TAT GAT AGC TCT GTT 570

P   D   S   A   W   R   I   M   T   T   L   N   M   L   G   G   R   Q   V   I   A   A   V   K   W   A   K   A   I   L
     CCA GAT TCA GCA TGG AGA ATT ATG ACC ACA CTC AAC ATG TTA GGT GGG CGT CAA GTG ATT GCA GCA GTG AAA TGG GCA AAG GCG ATA CTA 600

G   L   R   N   L   H   L   D   D   Q   M   T   T   K   L   M   F   L   Q   Y   S   W   M   M   A   L   G   W   R   S
     GGC TTG AGA AAC TTA CAC CTC GAT GAC CAA ATG ACC ATG AAA CTC ATG TTT CTC CAG TAC TCA TGG ATG ATG GCC TTG GGT TGG AGA TCA 630

Y   R   Q   S   G   N   L   C   F   A   P   D   L   I   I   N   E   Q   R   M   S   L   P   C   M   Y   L   L   Q
     TAC AGA CAA TCA GGA AAC CTG CTC TGC TTT GCT CCT GAT CTT ATT AAT GAG CAG AGA ATG TCT CTA CCC TGC ATG TAT CTG CTT CTC CAA 660

C   K   H   M   L   V   S   S   E   L   Q   R   L   Q   V   S   Y   E   E   Y   L   C   M   Y   T   L   I   K   A   I   V
     TGT AAA CAT ATG CTG GTC TCC TCT GAA TTA CAA AGA TTG CAG GTA TCC TAT GAA GAG TAT CTC TGT ATG TAT ACC TTA CTG ATC AAA GCC ATC GTC 690

S   S   V   P   Y   E   G   L   K   S   Q   E   L   F   D   E   I   R   M   T   Y   I   K   E   L   G   K   A   I   V
     TCC TCA GTT CCT TAT GAA GGT CTG AAG AGC CAA GAG CTG TTT GAT GAG ATT CGA ATG ACT TAT ATC AAA GAG CTA GGA AAA GCC ATC GTC 720

Y   R   E   G   N   S   S   Q   N   W   Q   R   F   Y   Q   L   T   K   L   L   D   S   M   H   E   V   V   E   N   L
     AAA AGG GAA GGG AAC TCC AGT CAG AAC TGG CAA CGG TTT TAC CAA CTG ACA AAG CTT CTG GAC TCC ATG CAT GAG GTG GTT GAG AAT CTC 750

L   T   Y   C   F   Q   T   F   L   D   Y   T   M   S   I   E   F   P   E   M   L   A   E   I   I   T   N   Q   I   P
     CTT ACC TAC TGC TTC CAG ACA TTT TTG GAT TAC ACC ATG AGT ATT GAA TTC CCA GAG ATG TTA GCT GAA ATC ATC ACT AAT CAG ATA CCA 780

K   Y   S   N   G   N   I   Y   Y   L   F   H   Q   Y   stop
     AAA TAT TCA AAT GGA AAT ATC TAC AAA AAG CTT CTG TTT CAT CAA AAA TGA
```

CAULIFLOWER FLORAL MERISTEM IDENTITY GENES AND METHODS OF USING SAME

This work was supported by grant DCB-9018749 awarded by the National Science Foundation. The United States Government has certain rights in this invention.

BACKGROUND OF THE INVENTION

1. Field of the Invention

This invention relates generally to the field of plant flowering and more specifically to genes involved in the regulation of flowering.

2. Background Information

A flower is the reproductive structure of a flowering plant. Following fertilization, the ovary of the flower becomes a fruit and bears seeds. As a practical consequence, production of fruit and seed-derived crops such as grapes, beans, corn, wheat and rice is dependent upon flowering.

Early in the plant life cycle, vegetative growth occurs, and roots, stems and leaves are formed. During the later period of reproductive growth, flowers as well as new shoots or branches develop. However, the factors responsible for the transition from vegetative to reproductive growth, and the onset of flowering, are poorly understood.

A variety of external signals, such as length of daylight and temperature, affect the time of flowering. The time of flowering also is subject to genetic controls that prevent young plants from flowering prematurely. Thus, the pattern of genes expressed in a plant is an important determinant of the time of flowering.

Given these external signals and genetic controls, a relatively fixed period of vegetative growth precedes flowering in a particular plant species. The length of time required for a crop to mature to flowering limits the geographic location in which it can be grown and can be an important determinant of yield. In addition, since the time of flowering determines when a plant is reproductively mature, the pace of a plant breeding program also depends upon the length of time required for a plant to flower.

Traditionally, plant breeding involves generating hybrids of existing plants, which are examined for improved yield or quality. The improvement of existing plant crops through plant breeding is central to increasing the amount of food grown in the world since the amount of land suitable for agriculture is limited. For example, the development of new strains of wheat, corn and rice through plant breeding has increased the yield of these crops grown in underdeveloped countries such as Mexico, India and Pakistan. Unfortunately, plant breeding is inherently a slow process since plants must be reproductively mature before selective breeding can proceed.

For some plant species, the length of time needed to mature to flowering is so long that selective breeding, which requires several rounds of backcrossing progeny plants with their parents, is impractical. For example, perennial trees such as walnut, hickory, oak, maple and cherry do not flower for several years after planting. As a result, breeding of such plant species for insect or disease-resistance or to produce improved wood or fruit, for example, would require many years, even if only a few rounds of selection were performed.

Methods of promoting early flowering can make breeding of long generation plants such as trees practical for the first time. Methods of promoting early flowering also would be useful for shortening growth periods, thereby broadening the geographic range in which a crop such as rice, corn or coffee can be grown. Unfortunately, methods for promoting early flowering in a plant have not yet been described. Thus, there is a need for methods that promote early flowering. The present invention satisfies this need and provides related advantages as well.

SUMMARY OF THE INVENTION

The present invention provides a nucleic acid molecule encoding a CAULIFLOWER (CAL) gene product. For example, the invention provides a nucleic acid molecule encoding *Arabidopsis thaliana* CAL and a nucleic acid molecule encoding *Brassica oleracea* CAL.

The invention also provides a nucleic acid molecule encoding a truncated CAL gene product. For example, the invention provides a nucleic acid molecule encoding the truncated *Brassica oleracea* var. *botrytis* CAL gene product. The invention also provides a nucleotide sequence that hybridizes under relatively stringent conditions to a nucleic acid molecule encoding a CAL gene product, a truncated CAL gene product, or a complementary sequence thereto.

The invention further provides the *Arabidopsis thaliana* CAL gene, *Brassica oleracea* CAL gene and *Brassica oleracea* var. *botrytis* CAL gene. In addition, the invention provides a nucleotide sequence that hybridizes under relatively stringent conditions to the *Arabidopsis thaliana* CAL gene, *Brassica oleracea* CAL gene or *Brassica oleracea* var. *botrytis* CAL gene, or a complementary sequence thereto.

The invention also provides vectors, including expression vectors, containing a nucleic acid molecule encoding a CAL gene product. The invention further provides a kit for converting shoot meristem to floral meristem in an angiosperm and a kit for promoting early flowering in an angiosperm.

In addition, the invention provides a CAL polypeptide, such as the *Arabidopsis thaliana* CAL polypeptide or the *Brassica oleracea* CAL polypeptide, as well as an antibody that specifically binds a CAL polypeptide. The invention further provides the truncated *Brassica oleracea* var. *botrytis* CAL polypeptide and an antibody that specifically binds the truncated *Brassica oleracea* var. *botrytis* CAL polypeptide.

The invention further provides a method of identifying a Brassica having a modified CAL allele by detecting a polymorphism associated with a CAL locus, where the CAL locus comprises a modified CAL allele that does not encode an active CAL gene product. For example, the polymorphism can be a restriction fragment length polymorphism and the modified CAL allele can be the *Brassica oleracea* var. *botrytis* CAL allele.

BRIEF DESCRIPTION OF THE DRAWINGS

FIG. 1 illustrates the nucleotide (SEQ ID NO: 1) and amino acid (SEQ ID NO: 2) sequence of the *Arabidopsis thaliana* AP1 cDNA.

FIG. 2 illustrates the nucleotide (SEQ ID NO: 3) and amino acid (SEQ ID NO: 4) sequence of the *Brassica oleracea* AP1 cDNA.

FIG. 3 illustrates the nucleotide (SEQ ID NO: 5) and amino acid (SEQ ID NO: 6) sequence of the *Brassica oleracea* var. *botrytis* AP1 cDNA.

FIG. 4 illustrates the nucleotide (SEQ ID NO: 7) and amino acid (SEQ ID NO: 8) sequence of the *Zea mays* AP1 cDNA. The GenBank accession number is L46400.

FIG. 5 illustrates the nucleotide (SEQ ID NO: 9) and amino acid (SEQ ID NO: 10) sequence of the *Arabidopsis thaliana* CAL cDNA.

FIG. 6 illustrates the nucleotide (SEQ ID NO: 11) and amino acid (SEQ ID NO: 12) sequence of the *Brassica oleracea* CAL cDNA.

FIG. 7 illustrates the nucleotide (SEQ ID NO: 13) and amino acid (SEQ ID NO: 14) sequence of the *Brassica oleracea* var. *botrytis* CAL cDNA.

FIGS. 8A–8B illustrate CAL gene structure and provide a comparison of various CAL amino acid sequences.

FIG. 8A. Exon-intron structure of Arabidopsis CAL gene. Exons are shown as boxes and introns as a solid line. Sizes (in base pairs) are indicated above. Locations of changes resulting in mutant alleles are indicated by arrows. MADS and K domains are hatched.

FIG. 8B. An alignment of three deduced amino acid sequences of CAL cDNAs. The complete *Arabidopsis thaliana* CAL amino acid sequence is displayed. The *Brassica oleracea* CAL (BoCAL) and *Brassica oleracea* var. *botrytis* CAL (BobCAL) amino acid sequences are shown directly below the Arabidopsis sequence where the sequences differ. The AP1 amino acid sequence is shown for comparison. The MADS domain is indicated in bold and the K domain is underlined. GenBank accession numbers are as follows: *Arabidopsis thaliana* CAL (L36925); *Brassica oleracea* CAL (L36926) and *Brassica oleracea* var. *botrytis* CAL (L36927).

FIG. 9 illustrates the nucleotide (SEQ ID NO: 15) and amino acid (SEQ ID NO: 16) sequence of the *Arabidopsis thaliana* LEAFY (LFY) cDNA.

FIG. 10 illustrates the genomic sequence of *Arabidopsis thaliana* AP1 (SEQ ID NO: 17).

FIG. 11 illustrates the genomic sequence of *Brassica oleracea* AP1 (SEQ ID NO: 18).

FIG. 12 illustrates the genomic sequence of *Brassica oleracea* var. *botrytis* AP1 (SEQ ID NO: 19).

FIG. 13 illustrates the genomic sequence of *Arabidopsis thaliana* CAL (SEQ ID NO: 20).

FIG. 14 illustrates the genomic sequence of *Brassica oleracea* CAL (SEQ ID NO: 21).

FIG. 15 illustrates the genomic sequence of *Brassica oleracea* var. *botrytis* CAL (SEQ ID NO: 22).

FIG. 16 illustrates the nucleotide (SEQ ID NO: 23) and amino acid (SEQ ID NO: 24) sequence of the rat glucocorticoid receptor ligand binding domain.

DETAILED DESCRIPTION OF THE INVENTION

The present invention provides a nucleic acid molecule encoding a CAULIFLOWER (CAL) gene product, which is a floral meristem identity gene product involved in the conversion of shoot meristem to floral meristem. For example, the invention provides a nucleic acid molecule encoding *Arabidopsis thaliana* CAL and a nucleic acid molecule encoding *Brassica oleracea* CAL (BOCAL) (Kempin et al., *Science*, 267:522–525 (1995), which is incorporated herein by reference). As disclosed herein, a CAL gene product can be expressed in an angiosperm, thereby converting shoot meristem to floral meristem in the angiosperm or promoting early flowering in the angiosperm. The invention also provides a nucleic acid molecule encoding a truncated CAL gene product such as a nucleic acid molecule encoding *Brassica oleracea* var. *botrytis* CAL (BobCAL). The invention also provides a nucleic acid molecule containing the *Arabidopsis thaliana* CAL gene, a nucleic acid molecule containing the *Brassica oleracea* CAL gene and a nucleic acid molecule containing the *Brassica oleracea* var. *botrytis* CAL gene. The invention further provides a kit for converting shoot meristem to floral meristem and a kit for promoting early flowering in an angiosperm. The invention provides a CAL polypeptide and an antibody that specifically binds CAL polypeptide. In addition, the invention provides the truncated BobCAL polypeptide and an antibody that specifically binds the truncated BobCAL polypeptide. The invention further provides a method of identifying a Brassica having a modified CAL allele by detecting a polymorphism associated with a CAL locus, where the CAL locus comprises a modified CAL allele that does not encode an active CAL gene product.

The present invention provides a non-naturally occurring angiosperm containing a first ectopically expressible nucleic acid molecule encoding a first floral meristem identity gene product. For example, the invention provides a transgenic angiosperm containing a first ectopically expressible floral meristem identity gene product such as APETALA1 (AP1), CAULIFLOWER (CAL) or LEAFY (LFY). Such a transgenic angiosperm can be, for example, a cereal plant, leguminous plant, oilseed plant, tree, fruit-bearing plant or ornamental flower.

A flower, like a leaf or shoot, is derived from the shoot apical meristem, which is a collection of undifferentiated cells set aside during embryogenesis. The production of vegetative structures, such as leaves or shoots, and of reproductive structures, such as flowers, is temporally segregated, such that a leaf or shoot arises early in a plant life cycle, while a flower develops later. The transition from vegetative to reproductive development is the consequence of a process termed floral induction (Yanofsky, *Ann. Rev. Plant Physiol. Plant Mol. Biol.* 46:167–188 (1995)).

Once induced, shoot apical meristem either persists and produces floral meristem, which gives rise to flowers, and lateral meristem, which gives rise to branches, or is itself converted to floral meristem. The fate of floral meristem is to differentiate into a single flower having a fixed number of floral organs in a whorled arrangement. Dicots, for example, contain four whorls (concentric rings) in which sepals (first whorl) and petals (second whorl) surround stamens (third whorl) and carpels (fourth whorl).

Although shoot meristem and floral meristem both consist of meristemic tissue, shoot meristem is distinguishable from the more specialized floral meristem. Shoot meristem generally is indeterminate and gives rise to an unspecified number of floral and lateral meristems. In contrast, floral meristem is determinate and gives rise to the fixed number of floral organs that comprise a flower.

By convention herein, a wild-type gene sequence is represented in upper case italic letters (for example, *APETALA1*), and a wild-type gene product is represented in upper case non-italic letters (APETALA1). Further, a mutant gene allele is represented in lower case italic letters (*ap1*), and a mutant gene product is represented in lower case non-italic letters (ap1).

Genetic studies have identified a number of genes involved in regulating flower development. These genes can be classified into different groups depending on their function. Flowering time genes, for example, are involved in floral induction and regulate the transition from vegetative to reproductive growth. In comparison, the floral meristem identity genes, which are the subject matter of the present invention as disclosed herein, encode proteins that promote the conversion of shoot meristem to floral meristem. In addition, floral organ identity genes encode proteins that determine whether sepals, petals, stamens or carpels are formed (Yanofsky, supra, 1995; Weigel, *Ann. Rev. Genetics* 29:19–39 (1995)). Some of the floral meristem identity gene products also have a role in specifying organ identity.

Floral meristem identity genes have been identified by characterizing genetic mutations that prevent or alter floral meristem formation. Among floral meristem identity gene mutations in *Arabidopsis thaliana*, those in the gene LEAFY (LFY) generally have the strongest effect on floral meristem identity. Mutations in LFY completely transform the basal-most flowers into secondary shoots and have variable effects on later-arising (apical) flowers. In comparison, mutations in the floral meristem identity gene APETALA1 (AP1) result in replacement of a few basal flowers by inflorescence shoots that are not subtended by leaves. An apical flower produced in an ap1 mutant has an indeterminate structure in which a flower arises within a flower. These mutant phenotypes indicate that both AP1 and LFY contribute to establishing the identity of the floral meristem although neither gene is absolutely required. The phenotype of lfy ap1 double mutants, in which structures with flower-like characteristics are very rare, indicates that LFY and AP1 encode partially redundant activities.

In addition to the LFY and AP1 genes, a third locus that greatly enhances the ap1 mutant phenotype has been identified in Arabidopsis. This locus, designated CAULIFLOWER (CAL), derives its name from the resulting "cauliflower" phenotype, which is strikingly similar to the common garden variety of cauliflower. In an ap1 cal double mutant, floral meristem that develops behaves as shoot meristem in that there is a massive proliferation of meristems in the position that normally would be occupied by a single flower. However, a plant homozygous for a particular cal mutation (cal-1) has a normal phenotype, indicating that AP1 can substitute for the loss of CAL in these plants. In addition, because floral meristem that forms in an ap1 mutant behaves as shoot meristem in an ap1 cal double mutant, CAL can largely substitute for AP1 in specifying floral meristem. These genetic data indicate that CAL and AP1 encode activities that are partially redundant in converting shoot meristem to floral meristem.

Other genetic loci play at least minor roles in specifying floral meristem identity. For example, although a mutation in APETALA2 (AP2) alone does not result in altered inflorescence characteristics, ap2 ap1 double mutants have indeterminate flowers (flowers with shoot-like characteristics) (Bowman et al., *Development* 119:721–743 (1993)). Also, mutations in the CLAVATA1 (CLV1) gene result in an enlarged meristem and lead to a variety of phenotypes (Clark et al., *Development* 119:397–418 (1993)). In a clv1 ap1 double mutant, formation of flowers is initiated, but the center of each flower often develops as an indeterminate inflorescence. Thus, mutations in CLAVATA1 result in the loss of floral meristem identity in the center of wild-type flowers. Genetic evidence also indicates that the gene product of UNUSUAL FLORAL ORGANS (UFO) plays a role in determining the identity of floral meristem. Additional floral meristem identity genes associated with altered floral meristem formation remain to be isolated.

Mutations in another locus, designated TERMINAL FLOWER (TFL), produce phenotypes that generally are reversed as compared to mutations in the floral meristem identity genes. For example, tfl mutants flower early, and the indeterminate apical and lateral meristems develop as determinate floral meristems (Alvarez et al., *Plant J.* 2:103–116 (1992)). These characteristics indicate that the TFL promotes maintenance of shoot meristem. TFL also acts directly or indirectly to negatively regulate AP1 and LFY expression in shoot meristem since AP1 and LFY are ectopically expressed in the shoot meristem of tfl mutants (Gustafson-Brown et al., *Cell* 76:131–143 (1994); Weigel et al., *Cell* 69:843–859 (1992)). It is recognized that a plant having a mutation in TFL can have a phenotype similar to a non-naturally occurring angiosperm of the invention. Such tfl mutants, however, are explicitly excluded from the scope of the present invention.

The results of such genetic studies indicate that several floral meristem identity gene products, including AP1, CAL and LFY, act redundantly to convert shoot meristem to floral meristem and that TFL acts directly or indirectly to negatively regulate expression of the floral meristem identity genes. As disclosed herein, ectopic expression of a single floral meristem identity gene product such as AP1, CAL or LFY is sufficient to convert shoot meristem to floral meristem. Thus, the present invention provides a non-naturally occurring angiosperm that contains an ectopically expressible nucleic acid molecule encoding a floral meristem identity gene product, provided that such ectopic expression is not due to a mutation in an endogenous TERMINAL FLOWER gene.

As disclosed herein, an ectopically expressible nucleic acid molecule encoding a floral meristem identity gene product can be, for example, a transgene encoding a floral meristem identity gene product under control of a heterologous gene regulatory element. In addition, such an ectopically expressible nucleic acid molecule can be an endogenous floral meristem identity gene coding sequence that is placed under control of a heterologous gene regulatory element. The ectopically expressible nucleic acid molecule also can be, for example, an endogenous floral meristem identity gene having a modified gene regulatory element such that the endogenous floral meristem identity gene is no longer subject to negative regulation by TFL.

The term "ectopically expressible" is used herein to refer to a gene transcript or gene product that can be expressed in a tissue other than a tissue in which it normally is produced. The actual ectopic expression thereof is dependent on various factors and can be constitutive or inducible expression. As disclosed herein, AP1, which normally is expressed in floral meristem, is ectopically expressible in shoot meristem. As disclosed herein, when a floral meristem identity gene product such as AP1, CAL or LFY is ectopically expressed in shoot meristem, the shoot meristem is converted to floral meristem and early flowering can occur (see Examples II, IV and V).

In particular, an ectopically expressible nucleic acid molecule encoding a floral meristem identity gene product can be expressed prior to the developmental time at which the corresponding endogenous gene normally is expressed. For example, an Arabidopsis plant grown under continuous light conditions expresses AP1 just prior to day 18, when normal flowering begins. However, as disclosed herein, AP1 can be ectopically expressed in shoot meristem earlier than day 18, resulting in early conversion of shoot meristem to floral meristem and early flowering. As shown in Example IID, a transgenic Arabidopsis plant that ectopically expresses AP1 in shoot meristem under control of a constitutive promoter flowers earlier than the corresponding non-transgenic plant (day 10 as compared to day 18).

As used herein, the term "floral meristem identity gene product" means a gene product that promotes conversion of shoot meristem to floral meristem. As disclosed herein, expression of a floral meristem identity gene product such as AP1, CAL or LFY in shoot meristem can convert shoot meristem to floral meristem. Furthermore, expression of a floral meristem identity gene product in shoot meristem also can promote early flowering (Examples IID, IVA and V). A floral meristem identity gene product is distinguishable from a late flowering gene product or an early flowering gene product, which are not encompassed within the present invention. In addition, reference is made herein to an "inactive" floral meristem identity gene product, as exemplified by BobCAL (see below). Expression of an inactive floral meristem identity gene product in an angiosperm does not result in the conversion of shoot meristem to floral meristem in the angiosperm.

A floral meristem identity gene product can be, for example, an AP1 gene product such as Arabidopsis AP1, which is a 256 amino acid gene product encoded by the AP1 cDNA sequence isolated from *Arabidopsis thaliana* (FIG. 5, SEQ ID NO: 2). The Arabidopsis AP1 cDNA encodes a highly conserved MADS domain, which can function as a DNA-binding domain, and a K domain, which is structurally similar to the coiled-coil domain of keratins and can be involved in protein-protein interactions.

In Arabidopsis, AP1 RNA is expressed in flowers but is not detectable in roots, stems or leaves (Mandel et al., *Nature* 360:273–277 (1992), which is incorporated herein by reference). The earliest detectable expression of AP1 RNA is in young floral meristem at the time it initially forms on the flanks of shoot meristem. Expression of AP1 increases as the floral meristem increases in size; no AP1 expression is detectable in shoot meristem. In later stages of development, AP1 expression ceases in cells that will give rise to reproductive organs (stamens and carpels), but is maintained in cells that will give rise to non-reproductive organs (sepals and petals; Mandel, supra, 1992).

As used herein, the term "APETALA1" or "AP1" means a floral meristem identity gene product that is characterized, in part, by having an amino acid sequence that is related to the Arabidopsis AP1 amino acid sequence shown in FIG. 1 (SEQ ID NO: 2) or to the *Zea mays* AP1 amino acid sequence shown in FIG. 4 (SEQ ID NO: 8). In nature, AP1 is expressed in floral meristem.

CAULIFLOWER (CAL) is another example of a floral meristem identity gene product. As used herein, the term "CAULIFLOWER" or "CAL" means a floral meristem identity gene product that is characterized in part by having an amino acid sequence that has at least about 70 percent identity with the amino acid sequence shown in FIG. 5 (SEQ ID NO: 10) in the region from amino acid 1 to amino acid 160 or with the amino acid sequence shown in FIG. 6 (SEQ ID NO: 12) in the region from amino acid 1 to amino acid 160. In nature, CAL is expressed in floral meristem.

The present invention provides a nucleic acid molecule encoding a CAL, including, for example, the Arabidopsis CAL cDNA sequence shown in FIG. 5 (SEQ ID NO: 9). As disclosed herein, CAL, like AP1, contains a MADS domain and a K domain. The MADS domains of CAL and AP1 differ in only five of 56 amino acid residues, where four of the five differences represent conservative amino acid replacements. Over the entire sequence, the Arabidopsis CAL and Arabidopsis AP1 sequences (SEQ ID NOS: 10 and 2) are 76% identical and are 88% similar if conservative amino acid substitutions are allowed.

Similar to the expression pattern of AP1, CAL RNA is expressed in young floral meristem in Arabidopsis. However, in contrast to AP1 expression, which is high throughout sepal and petal development, CAL expression is low in these organs.

LEAFY (LFY) is yet another example of a floral meristem identity gene product. As used herein, the term "LEAFY" or "LFY" means a floral meristem identity gene product that is characterized in part by having an amino acid sequence that is related to the amino acid sequence shown in FIG. 9 (SEQ ID NO: 16) In nature, LFY is expressed in floral meristem as well as during vegetative development. As disclosed herein, ectopic expression of floral meristem identity gene products, which normally are expressed in floral meristem, such as AP1 or CAL or LFY or combinations thereof, in shoot meristem can convert shoot meristem to floral meristem and promote early flowering.

Flower development in Arabidopsis is recognized in the art as a model for flower development in angiosperms in general. Gene orthologs corresponding to the Arabidopsis genes involved in the early steps of flower formation have been identified in distantly related plant species, and these gene orthologs show remarkably similar RNA expression patterns. Mutations in these genes also result in phenotypes that correspond to the phenotype produced by a similar mutation in Arabidopsis. For example, orthologs of the Arabidopsis floral meristem identity genes AP1 and LFY and the Arabidopsis organ identity genes AGAMOUS, APETALA3 and PISTILLATA have been isolated from monocots such as maize and, where characterized, reveal the anticipated RNA expression patterns and related mutant phenotypes. (Schmidt et al., *Plant Cell* 5:729–737 (1993); and Veit et al., *Plant Cell* 5:1205–1215 (1993), each of which is incorporated herein by reference). Furthermore, a gene ortholog can be functionally interchangeable in that it can function across distantly related species boundaries (Mandel et al., *Cell* 71:133–143 (1992), which is incorporated herein by reference). Taken together, these data suggest that the underlying mechanisms controlling the initiation and proper development of flowers are conserved across distantly related dicot and monocot boundaries. Therefore, results obtained using Arabidopsis can be predictive of results that can be expected in other angiosperms.

Floral meristem identity genes in particular are conserved throughout the plant kingdom. For example, a gene ortholog of Arabidopsis AP1 has been isolated from *Antirrhinum majus* (snapdragon; Huijser et al., *EMBO J.* 11:1239–1249 (1992), which is herein incorporated by reference). As disclosed herein, an ortholog of Arabidopsis AP1 also has been isolated from *Zea Mays* (maize; see Example IA). Similarly, gene orthologs of Arabidopsis LFY have been isolated from *Antirrhinum majus*, tobacco and poplar tree (Coen et al., *Cell,* 63:1311–1322 (1990); Kelly et al., *Plant Cell* 7:225–234 (1995); and Strauss et al., *Molec. Breed* 1:5–26 (1995), each of which is incorporated herein by reference). In addition, a mutation in the Antirrhinum AP1 ortholog results in a phenotype similar to the Arabidopsis ap1 mutant phenotype described above (Huijser et al., supra, 1992). Similarly, a mutation in the Antirrhinum LFY ortholog results in a phenotype similar to the Arabidopsis lfy mutant phenotype (Coen et al., supra, 1995). These studies indicate that AP1 and LFY function similarly in distantly related angiosperms.

A floral meristem identity gene product also can function across species boundaries. For example, Arabidopsis LFY can convert shoot meristem to floral meristem when expressed in aspen trees (Weigel and Nilsson, *Nature* 377:495–500 (1995), which is incorporated herein by reference). As disclosed herein, a nucleic acid molecule encoding an Arabidopsis AP1 or CAL gene product (SEQ ID NOS: 1 and 9), for example, also can be used to convert shoot meristem to floral meristem in an angiosperm. Thus, a nucleic acid molecule encoding an Arabidopsis AP1 gene product (SEQ ID NO: 1) or an Arabidopsis CAL gene product (SEQ ID NO: 9) can be introduced into an angiosperm such as corn, wheat or rice and, upon expression, can convert shoot meristem to floral meristem in the transgenic angiosperm. Furthermore, as disclosed herein, the conserved nature of an AP1 or CAL or LFY gene among diverse angiosperms, allows a nucleic acid molecule encoding a floral meristem identity gene product from essentially any angiosperm to be introduced into essentially any other angiosperm, wherein the expression of the nucleic acid molecule in shoot meristem can convert shoot meristem to floral meristem.

If desired, a novel AP1, CAL or LFY sequence can be isolated from an angiosperm using a nucleotide sequence as a probe and methods well known in the art of molecular biomolecular biology (Sambrook et al. (eds.), *Molecular Cloning: A Laboratory Manual* (Second Edition), Plainview, N.Y.: Cold Spring Harbor Laboratory Press (1989), which is herein incorporated by reference). As exemplified herein and discussed in detail below (see Example IA), the AP1 ortholog from *Zea Mays* (maize; SEQ ID NO: 7) was isolated using the Arabidopsis AP1 cDNA as a probe (SEQ ID NO: 1).

In one embodiment, the invention provides a non-naturally occurring angiosperm that contains an ectopically expressible nucleic acid molecule encoding a floral meristem identity gene product and that is characterized by early flowering. As used herein, the term "characterized by early flowering," when used in reference to a non-naturally occurring angiosperm of the invention, means a non-naturally occurring angiosperm that forms flowers sooner than flowers would form on a corresponding naturally occurring angiosperm that does not ectopically express a floral meristem identity gene product, grown under the same conditions. Flowering times for naturally occurring angiosperms are well known in the art and depend, in part, on genetic factors and on the environmental conditions, such as day length. Thus, given a defined set of environmental conditions, a naturally occurring plant will flower at a relatively predictable time.

It is recognized that various transgenic plants that are characterized by early flowering have been described. Such transgenic plants are described herein and are readily distinguishable or explicitly excluded from the present invention. For example, a product of a "late-flowering gene" can promote early flowering but does not specify the conversion of shoot meristem to floral meristem. Therefore, a transgenic plant expressing a late-flowering gene product is distinguishable from a non-naturally occurring angiosperm of the invention. For example, a transgenic plant expressing the late-flowering gene, CONSTANS (CO), flowers earlier than a corresponding wild type plant (Putterill et al., *Cell* 80:847–857 (1995)). However, expression of exogenous CONSTANS does not convert shoot meristem to floral meristem.

Early flowering also has been observed in a transgenic tobacco plant expressing an exogenous rice MADS domain gene. Although the product of this gene promotes early flowering, it does not specify the identity of floral meristem and, thus, cannot convert shoot meristem to floral meristem (Chung et al., Plant Mol. Biol. 26:657–665 (1994)). Therefore, the early-flowering CO and rice MADS domain gene transgenic plants are distinguishable from the early-flowering non-naturally occurring angiosperms of the invention.

Mutations in a class of genes known as "early-flowering genes" also result in plants that flower prematurely. Such early flowering genes include, for example, EARLY FLOWERING 1-3 (ELF1, ELF2, ELF3); EMBRYONIC FLOWER 1,2 (EMF1, EMF2); LONG HYPOCOTYL 1,2 (HY1, HY2); PHYTOCHROME B (PHYB), SPINDLY (SPY) and TERMINAL FLOWER (TFL) (Weigel, supra, 1995). However, the wild type product of an early flowering gene retards flowering and is distinguishable from a floral meristem identity gene product in that it does not promote conversion of shoot meristem to floral meristem.

An Arabidopsis plant having a mutation in the TERMINAL FLOWER (TFL) gene flowers early and is characterized by the conversion of shoots to flowers (Alvarez et al., *Plant J.* 2:103–116 (1992), which is incorporated herein by reference). However, TFL is not a floral meristem identity gene product, as defined herein. Specifically, it is the loss of TFL that promotes conversion of shoot meristem to floral meristem. Since the function of TFL is to antagonize formation of floral meristem, a tfl mutant, which has lost this antagonist function, permits conversion of shoot meristem to floral meristem. Although TFL is not a floral meristem identity gene product and does not itself convert shoot meristem to floral meristem, the loss of TFL can result in a plant with an ectopically expressed floral meristem identity gene product. Such tfl mutants, in which a mutation in TFL results in conversion of shoot meristem to floral meristem, are explicitly excluded from the present invention.

As used herein, the term "non-naturally occurring angiosperm" means an angiosperm that contains a genome that has been modified by man. A transgenic angiosperm, for example, contains an exogenous nucleic acid molecule and, therefore, contains a genome that has been modified by man. Furthermore, an angiosperm that contains, for example, a mutation in an endogenous floral meristem identity gene regulatory element as a result of exposure to a mutagenic agent by man also contains a genome that has been modified by man. In contrast, a plant containing a spontaneous or naturally occurring mutation is not a "non-naturally occurring angiosperm" and, therefore, is not encompassed within the invention.

As used herein, the term "transgenic" refers to an angiosperm that contains in its genome an exogenous nucleic acid molecule, which can be derived from the same or a different species. The exogenous nucleic acid molecule that is introduced into the angiosperm can be a gene regulatory element such as a promoter or other regulatory element or can be a coding sequence, which can be linked to a heterologous gene regulatory element.

As used herein, the term "angiosperm" means a flowering plant. Angiosperms are well known and produce a variety of useful products including materials such as lumber, rubber, and paper; fibers such as cotton and linen; herbs and medicines such as quinine and vinblastine; ornamental flowers such as roses and orchids; and foodstuffs such as grains, oils, fruits and vegetables.

Angiosperms are divided into two broad classes based on the number of cotyledons, which are seed leaves that generally store or absorb food. Thus, a monocotyledonous angiosperm is an angiosperm having a single cotyledon, and a dicotyledonous angiosperm is an angiosperm having two cotyledons.

Angiosperms encompass a variety of flowering plants, including, for example, cereal plants, leguminous plants, oilseed plants, trees, fruit-bearing plants and ornamental flowers, which general classes are not necessarily exclusive.

Such angiosperms include for example, a cereal plant, which produces an edible grain cereal. Such cereal plants include, for example, corn, rice, wheat, barley, oat, rye, orchardgrass, guinea grass, sorghum and turfgrass. In addition, a leguminous plant is an angiosperm that is a member of the pea family (Fabaceae) and produces a characteristic fruit known as a legume. Examples of leguminous plants include, for example, soybean, pea, chickpea, moth bean, broad bean, kidney bean, lima bean, lentil, cowpea, dry bean, and peanut. Examples of legumes further also include alfalfa, birdsfoot trefoil, clover and sainfoin. Furthermore, an oilseed plant is an angiosperm that has seeds useful as a source of oil. Examples of oilseed plants include soybean, sunflower, rapeseed and cottonseed.

A tree is an angiosperm and is a perennial woody plant, generally with a single stem (trunk). Examples of trees include alder, ash, aspen, basswood (linden), beech, birch, cherry, cottonwood, elm, eucalyptus, hickory, locust, maple, oak, persimmon, poplar, sycamore, walnut and willows. Such trees are used for pulp, paper, and structural material, as well as providing a major source of fuel.

A fruit-bearing plant also is an angiosperm and produces a mature, ripened ovary (usually containing seeds) that is suitable for human or animal consumption. Examples of fruit-bearing plants include grape, orange, lemon, grapefruit, avocado, date, peach, cherry, olive, plum, coconut, apple and pear trees and blackberry, blueberry, raspberry, strawberry, pineapple,cucmato, cucumber and eggplant plants. An ornamental flower is an angiosperm cultivated for its decorative flower. Examples of ornamental flowers include rose, orchid, lily, tulip and chrysanthemum, snapdragon, camelia, carnation and petunia. The skilled artisan will recognize that the invention can be practiced on these or other angiosperms, as desired.

In various embodiments, the present invention provides a non-naturally occurring angiosperm having an ectopically expressible first nucleic acid molecule encoding a first floral meristem identity gene product, provided the first nucleic acid molecule is not ectopically expressed due to a mutation in an endogenous TFL gene. If desired, a non-naturally occurring angiosperm of the invention can contain an ectopically expressible second nucleic acid molecule encoding a second floral meristem identity gene product, which is different from the first floral meristem identity gene product.

An ectopically expressible nucleic acid molecule can be expressed, as desired, either constitutively or inducibly. Such an ectopically expressible nucleic acid molecule can be an endogenous nucleic acid molecule and can contain, for example, a mutation in its endogenous gene regulatory element or can contain an exogenous, heterologous gene regulatory element that is linked to and directs expression of the endogenous nucleic acid molecule. In addition, an ectopically expressible nucleic acid molecule encoding a floral meristem identity gene product can be an exogenous nucleic acid molecule encoding a floral meristem identity gene product and containing a heterologous gene regulatory element.

The invention provides, for example, a non-naturally occurring angiosperm containing a first ectopically expressible nucleic acid molecule encoding a first floral meristem identity gene product. If desired, a non-naturally occurring angiosperm of the invention can contain a floral meristem identity gene having a modified gene regulatory element and also can contain a second ectopically expressible nucleic acid molecule encoding a second floral meristem identity gene product, provided that neither the first nor second ectopically expressible nucleic acid molecule is ectopically expressed due to a mutation in an endogenous TERMINAL FLOWER gene.

As used herein, the term "modified gene regulatory element" means a regulatory element having a mutation that results in ectopic expression in shoot meristem of the floral meristem identity gene regulated by the gene regulatory element. Such a gene regulatory element can be, for example, a promoter or enhancer element and can be positioned 5' or 3' to the coding sequence or within an intronic sequence of the floral meristem identity gene. Such a modification can be, for example, a nucleotide insertion, deletion or substitution and can be produced by chemical mutagenesis using a mutagen such as ethylmethane sulfonate (see Example IIIA) or by insertional mutagenesis using a transposable element. For example, a modified gene regulatory element can be a functionally inactivated binding site for TFL or a gene product regulated by TFL, such that modification of the gene regulatory element results in ectopic expression of the floral meristem identity gene product in shoot meristem.

The invention also provides a transgenic angiosperm containing a first exogenous gene promoter that regulates a first ectopically expressible nucleic acid molecule encoding a first floral meristem identity gene product and a second exogenous gene promoter that regulates a second ectopically expressible nucleic acid molecule encoding a second floral meristem identity gene product.

The invention also provides a transgenic angiosperm containing a first exogenous ectopically expressible nucleic acid molecule encoding a first floral meristem identity gene product and a second exogenous gene promoter that regulates a second ectopically expressible nucleic acid molecule encoding a second floral meristem identity gene product, provided that the first nucleic acid molecule is not ectopically expressed due to a mutation in an endogenous TERMINAL FLOWER gene.

The invention also provides a transgenic angiosperm containing a first exogenous ectopically expressible nucleic acid molecule encoding a first floral meristem identity gene product and a second exogenous ectopically expressible nucleic acid molecule encoding a second floral meristem identity gene product, where the first floral meristem identity gene product is different from the second floral meristem identity gene product and provided that neither nucleic acid molecule is ectopically expressed due to a mutation in an endogenous TERMINAL FLOWER gene.

The ectopic expression of first and second floral meristem identity gene products can be particularly useful. For example, ectopic expression of AP1 and LFY in a plant promotes flowering earlier than ectopic expression of AP1 alone or ectopic expression of LFY alone. Thus, plant breeding, for example, can be further accelerated, if desired.

First and second floral meristem identity gene products can be, for example, AP1 and CAL, or can be AP1 and LFY or can be CAL and LFY. It should be recognized that where a transgenic angiosperm of the invention contains two exogenous nucleic acid molecules, the order of introducing such a first and a second nucleic acid molecule is not important for purposes of the present invention. Thus, a transgenic angiosperm of the invention having, for example, AP1 as the first floral meristem identity gene product and CAL as the second floral meristem identity gene product is equivalent to a transgenic angiosperm having CAL as the first floral meristem identity gene product and AP1 as the second floral meristem identity gene product.

The invention also provides methods of converting shoot meristem to floral meristem in an angiosperm by ectopically expressing an ectopically expressible nucleic acid molecule encoding a floral meristem identity gene product in the angiosperm. Thus, the invention provides, for example, methods of converting shoot meristem to floral meristem in an angiosperm by introducing an exogenous ectopically expressible nucleic acid molecule encoding a floral meristem identity gene product into the angiosperm, thereby producing a transgenic angiosperm. A floral meristem identity gene product such as AP1, CAL or LFY, or a chimeric protein containing, in part, a floral meristem identity gene product (see below) is useful in the methods of the invention.

As used herein, the term "introducing," when used in reference to an angiosperm, means transferring an exogenous nucleic acid molecule into the angiosperm. For example, an exogenous nucleic acid molecule can be introduced into an angiosperm by methods such as Agrobacterium-mediated transformation or direct gene transfer methods including microprojectile-mediated transformation (Klein et al., *Nature* 327:70–73 (1987), which is incorporated herein by reference). These and other methods of introducing a nucleic acid molecule into an angiosperm are well known in the art (Bowman et al. (ed.), *Arabidopsis: An Atlas of Morphology and Development*, New York: Springer (1994); Valvekens et al., *Proc. Natl. Acad. Sci.. USA* 85:5536–5540 (1988); and Wang et al., *Transformation of Plants and Soil Microorganisms*, Cambridge, UK: University Press (1995), each of which is incorporated herein by reference).

As used herein, the term "converting shoot meristem to floral meristem" means promoting the formation of flower progenitor tissue where shoot progenitor tissue would normally be formed. As a result of the conversion of shoot meristem to floral meristem, flowers form in an angiosperm where shoots normally would form. The conversion of shoot meristem to floral meristem can be identified using well known methods, such as scanning electron microscopy, light microscopy or visual inspection.

The invention also provides methods of converting shoot meristem to floral meristem in an angiosperm by introducing a first ectopically expressible nucleic acid molecule encoding a first floral meristem identity gene product and a second ectopically expressible nucleic acid molecule encoding a second floral meristem identity gene product into the angiosperm. As discussed above, first and second floral meristem identity gene products useful in the invention can be, for example, AP1 and CAL or AP1 and LFY or CAL and LFY.

The invention also provides methods of promoting early flowering in an angiosperm by ectopically expressing a nucleic acid molecule encoding a floral meristem identity gene product in the angiosperm, provided that the nucleic acid molecule is not ectopically expressed due to a mutation in an endogenous TERMINAL FLOWER gene. For example, the invention provides methods of promoting early flowering in an angiosperm by introducing an ectopically expressible nucleic acid molecule encoding a floral meristem identity gene product into the angiosperm, thus producing a transgenic angiosperm. A floral meristem identity gene product such as AP1, CAL or LFY, or a chimeric protein containing, in part, a floral meristem identity gene product (see below) is useful in methods of promoting early flowering.

The present invention further provides nucleic acid molecules encoding floral meristem identity gene products. For example, the invention provides a nucleic acid molecule encoding CAL, having at least about 70 percent amino acid identity with amino acids 1 to 160 of SEQ ID NO: 10 or SEQ ID NO: 11. The invention also provides a nucleic acid molecule encoding *Arabidopsis thaliana* CAL having the amino acid sequence shown in FIG. 5 (SEQ ID NO: 10) and a nucleic acid molecule encoding *Brassica oleracea* CAL having the amino acid sequence shown in FIG. 6 (SEQ ID NO: 12). In addition, the invention provides a nucleic acid molecule encoding *Brassica oleracea* AP1 having the amino acid sequence shown in FIG. 2 (SEQ ID NO: 4) and a nucleic acid molecule encoding *Brassica oleracea* var. *botrytis* AP1 having the amino acid sequence shown in FIG. 3 (SEQ ID NO: 6). The invention also provides a nucleic acid molecule encoding *Zea mays* AP1 having the amino acid sequence shown in FIG. 4 (SEQ ID NO: 8).

As disclosed herein, CAL is highly conserved among different angiosperms. For example, Arabidopsis CAL (SEQ ID NO: 10) and *Brassica oleracea* CAL (SEQ ID NO: 12) share about 80 percent amino acid identity. In the region from amino acid 1 to amino acid 160, Arabidopsis CAL and *Brassica oleracea* CAL are about 89 percent identical at the amino acid level. Using a nucleotide sequence derived from a conserved region of SEQ ID NO: 9 or SEQ ID NO: 11, a nucleic acid molecule encoding a novel CAL ortholog can be isolated from other angiosperms. Using methods such as those described by Purugganan et al. (*Genetics* 40: 345–356 (1995)), one can readily confirm that the newly isolated molecule is a CAL ortholog. Thus, a nucleic acid molecule encoding CAL, which has at least about 70 percent amino acid identity with Arabidopsis CAL (SEQ ID NO: 10) or *Brassica oleracea* CAL (SEQ ID NO: 12), can be isolated and identified using well known methods.

The invention also provides a nucleic acid molecule encoding a truncated CAL gene product. For example, the invention provides a nucleic acid molecule encoding the *Brassica oleracea* var. *botrytis* CAL gene product (BobCAL). BobCAL contains 150 amino acids of the approximately 255 amino acids encoded by a full-length CAL cDNA (see FIG. 7; SEQ ID NO: 14; see, also, FIG. 8B).

The invention also provides a nucleic acid containing the *Arabidopsis thaliana* AP1 gene (FIG. 10; SEQ ID NO: 17), a nucleic acid molecule containing the *Brassica oleracea* AP1 gene (FIG. 11; SEQ ID NO: 18) and a nucleic acid molecule containing the *Brassica oleracea* var. *botrytis* AP1 gene (FIG. 12; SEQ ID NO: 19). In addition, the invention also provides a nucleic acid containing the *Arabidopsis thaliana* CAL gene (FIG. 13; SEQ ID NO: 20) and a nucleic acid molecule containing the *Brassica oleracea* CAL gene (FIG. 11; SEQ ID NO: 21). In addition, the invention provides a nucleic acid molecule containing the *Brassica oleracea* var. *botrytis* CAL gene (FIG. 15; SEQ ID NO: 22).

The invention further provides a nucleotide sequence that hybridizes under relatively stringent conditions to a nucleic acid molecule encoding a CAL, or a complementary sequence thereof. In particular, such a nucleotide sequence can hybridize under relatively stringent conditions to a nucleic acid molecule encoding Arabidopsis CAL (SEQ ID NO: 9) or *Brassica oleracea* CAL (SEQ ID NO: 11), or a complementary sequence thereof. Similarly, the present invention provides a nucleotide sequence that hybridizes under relatively stringent conditions to a nucleic acid molecule encoding *Zea mays* AP1 (SEQ ID NO: 7), or a complementary sequence thereof.

In general, a nucleotide sequence that hybridizes under relatively stringent conditions to a nucleic acid molecule is a single-stranded nucleic acid sequence that can range in size from about 10 nucleotides to the full-length of a gene or a cDNA. Such a nucleotide sequence can be chemically synthesized, using routine methods or can be purchased from a commercial source. In addition, such nucleotide sequences can be obtained by enzymatic methods such as random priming methods, the polymerase chain reaction (PCR) or by standard restriction endonuclease digestion, followed by denaturation (Sambrook et al., supra, 1989).

A nucleotide sequence that hybridizes under relatively stringent conditions to a nucleic acid molecule can be used, for example, as a primer for PCR (Innis et al. (ed.) *PCR Protocols: A Guide to Methods and Applications*, San Diego, Calif.: Academic Press, Inc. (1990)). Such a nucleotide sequence generally contains about 10 to about 50 nucleotides.

A nucleotide sequence that hybridizes under relatively stringent conditions to a nucleic acid molecule also can be used to screen a cDNA or genomic library to obtain a related nucleotide sequence. For example, a cDNA library that is prepared from rice or wheat can be screened with a nucleotide sequence derived from the *Zea mays* AP1 sequence in order to isolate a rice or wheat ortholog of AP1. Generally, such a nucleotide sequence contains at least about 14–16 nucleotides depending, for example, on the hybridization conditions to be used.

A nucleotide sequence derived from a nucleic acid molecule encoding *Zea mays* AP1 (SEQ ID NO: 7) also can be used to screen a *Zea mays* cDNA library to isolate a sequence that is related to but distinct from AP1. Furthermore, such a hybridizing nucleotide sequence can be used to analyze RNA levels or patterns of expression, as by northern blotting or by in situ hybridization to a tissue section. Such a nucleotide sequence also can be used in Southern blot analysis to evaluate gene structure and identify the presence of related gene sequences.

One skilled in the art would select a particular nucleotide sequence that hybridizes under relatively stringent conditions to a nucleic acid molecule encoding a floral meristem identity gene product based on the application for which the sequence will be used. For example, in order to isolate an ortholog of AP1, one can choose a region of AP1 that is highly conserved among known AP1 sequences such as Arabidopsis AP1 (SEQ ID NO: 1) and *Zea mays* AP1 (GenBank accession number L46400; SEQ ID NO: 7). Similarly, in order to isolate an ortholog of CAL, one can choose a region of CAL that is highly conserved among known CAL cDNAs, such as Arabidopsis CAL (SEQ ID NO: 9) and Brassica CAL (SEQ ID NO: 11). It further would be recognized, for example, that the region encoding the MADS domain, which is common to a number of genes, can be excluded from the nucleotide sequence. In addition, one can use a full-length Arabidopsis AP1 or CAL cDNA nucleotide sequence (SEQ ID NO: 1 or SEQ ID NO: 9) to isolate an ortholog of AP1 or CAL.

For example, the Arabidopsis AP1 cDNA shown in FIG. 1 (SEQ ID NO: 1) can be used as a probe to identify and isolate a novel AP1 ortholog. Similarly, the Arabidopsis CAL cDNA shown in FIG. 5 (SEQ ID NO: 9) can be used to identify and isolate a novel CAL ortholog (see Examples IA and IIIC, respectively). In order to identify related MADS domain genes, a nucleotide sequence derived from the MADS domain of AP1 or CAL, for example, also can be useful to isolate a related gene sequence encoding this DNA-binding motif.

Hybridization utilizing a nucleotide sequence of the invention requires that hybridization be performed under relatively stringent conditions such that non-specific hybridization is minimized. Appropriate hybridization conditions can be determined empirically, or can be estimated based, for example, on the relative G+C content of the probe and the number of mismatches between the probe and target sequence, if known. Hybridization conditions can be adjusted as desired by varying, for example, the temperature of hybridizing or the salt concentration (Sambrook, supra, 1989).

The invention also provides a vector containing a nucleic acid molecule encoding a CAL gene product. In addition, the invention provides a vector containing a nucleic acid molecule encoding the *Zea mays* AP1 gene product. A vector can be a cloning vector or an expression vector and provides a means to transfer an exogenous nucleic acid molecule into a host cell, which can be a prokaryotic or eukaryotic cell. Such vectors are well known and include plasmids, phage vectors and viral vectors. Various vectors and methods for introducing such vectors into a cell are described, for example, by Sambrook et al., supra, 1989, and by Glick and Thompson (eds.), *Methods in Plant Molecular Biology and Biotechnology*, Boca Raton, Fla.: CRC Press (1993), which is incorporated herein by reference.

The invention also provides an expression vector containing a nucleic acid molecule encoding a floral meristem identity gene product such as CAL, AP1 or LFY. Expression vectors are well known in the art and provide a means to transfer and express an exogenous nucleic acid molecule into a host cell. Thus, an expression vector contains, for example, transcription start and stop sites such as a TATA sequence and a poly-A signal sequence, as well as a translation start site such as a ribosome binding site and a stop codon, if not present in the coding sequence.

An expression vector can contain, for example, a constitutive regulatory element useful for promoting expression of an exogenous nucleic acid molecule in a plant cell. The use of a constitutive regulatory element can be particularly advantageous because expression from the element is relatively independent of developmentally regulated or tissue-specific factors. For example, the cauliflower mosaic virus 35S promoter (CaMV35S) is a well-characterized constitutive regulatory element that produces a high level of expression in all plant tissues (Odell et al., *Nature* 313:810–812 (1985), which is incorporated herein by reference). The CaMV35S promoter is particularly useful because it is active in numerous different angiosperms (Benfey and Chua, *Science* 250:959–966 (1990), which is incorporated herein by reference; Odell et al., supra, 1985). Other constitutive regulatory elements useful for expression in an angiosperm include, for example, the nopaline synthase (nos) gene promoter (An, *Plant Physiol.* 81:86 (1986), which is herein incorporated by reference).

In addition, an expression vector of the invention can contain a regulated gene regulatory element such as a promoter or enhancer element. A particularly useful regulated promoter is a tissue-specific promoter such as the shoot meristem-specific CDC2 promoter (Hemerly et al., *Plant Cell* 5:1711–1723 (1993), which is incorporated herein by reference), or the AGL8 promoter, which is active in the apical shoot meristem immediately after the transition to flowering (Mandel and Yanofsky, *Plant Cell* 7:1763–1771 (1995), which is incorporated herein by reference).

An expression vector of the invention also can contain an inducible regulatory element, which has conditional activity dependent upon the presence of a particular regulatory factor. Useful inducible regulatory elements include, for example, a heat-shock promoter (Ainley and Key, *Plant Mol. Biol.* 14:949 (1990), which is herein incorporated by reference) or a nitrate-inducible promoter derived from the spinach nitrite reductase gene (Back et al., *Plant Mol. Biol.* 17:9 (1991), which is herein incorporated by reference). A hormone-inducible element (Yamaguchi-Shinozaki et al., *Plant Mol. Biol.* 15:905 (1990) and Kares et al., *Plant Mol. Biol.* 15:225 (1990), which are herein incorporated by reference) or a light-inducible promoter, such as that associated with the small subunit of RuBP carboxylase or the LHCP gene families (Feinbaum et al., *Mol. Gen. Genet.* 226:449 (1991) and Lam and Chua, *Science* 248:471 (1990), which are herein incorporated by reference) also can be useful in an expression vector of the invention. A human glucocorticoid response element also can be used to achieve steroid hormone-dependent gene expression in plants (Schena et al., *Proc. Natl. Acad. Sci. USA* 88:10421 (1991), which is herein incorporated by reference).

An appropriate gene regulatory element such as a promotor is selected depending on the desired pattern or level of expression of a nucleic acid molecule linked thereto. For example, a constitutive promoter, which is active in all tissues, would be appropriate to express a desired gene product in all cells containing the vector. In addition, it can be desirable to restrict expression of a nucleic acid molecule to a particular tissue or during a particular stage of development. A developmentally regulated or tissue-specific expression can be useful for this purpose and can avoid potential undesirable side-effects that can accompany unregulated expression. Inducible expression also can be particularly useful to manipulate the timing of gene expression such that, for example, a population of transgenic angiosperms of the invention that contain an expression vector comprising a floral meristem identity gene linked to an inducible promoter can be induced to flower essentially at the same time. Such timing of flowering can be useful, for example, for manipulating the time of crop harvest.

The invention also provides a kit containing an expression vector having a nucleic acid molecule encoding a floral meristem identity gene product. Such a kit is useful for converting shoot meristem to floral meristem in an angiosperm or for promoting early flowering in an angiosperm. If desired, such a kit can contain appropriate reagents, which can allow relatively high efficiency of transformation of an angiosperm with the vector. Furthermore, a control plasmid lacking the floral meristem identity gene can be included in the kit to determine, for example, the efficiency of transformation.

The invention further provides a host cell containing a vector comprising a nucleic acid molecule encoding CAL. A host cell can be prokaryotic or eukaryotic and can be, for example, a bacterial cell, yeast cell, insect cell, xenopus cell, mammalian cell or plant cell.

The invention also provides a transgenic garden variety cauliflower plant containing an exogenous nucleic acid molecule selected from the group consisting of a nucleic acid molecule encoding a CAL gene product and a nucleic acid molecule encoding an AP1 gene product. Such a transgenic cauliflower plant can produce an edible flower in place of the typical cauliflower vegetable.

A nucleic acid encoding CAL has been isolated from a *Brassica oleracea* line that produces wild-type flowers (BoCAL) and from the common garden variety of cauliflower, *Brassica oleracea* var. *botrytis* (BobCAL), which lacks flowers. The *Brassica oleracea* CAL cDNA (SEQ ID NO: 10) is highly similar to the Arabidopsis CAL cDNA (SEQ ID NO: 12; and see FIG. 8). In contrast, the *Brassica oleracea* var. *botrytis* CAL cDNA contains a stop codon, predicting that the BobCAL protein will be truncated after amino acid 150 (SEQ ID NO: 14 and see FIG. 8). The correlation of full-length Arabidopsis and *Brassica oleracea* CAL gene products with a flowering phenotype indicates that transformation of non-flowering garden varieties of cauliflower such as *Brassica oleracea* var. *botrytis* with a full-length CAL cDNA can induce flowering in the transgenic cauliflower plant.

As used herein, the term "CAL gene product" means a full-length CAL gene product that does not terminate substantially before amino acid 255 and that, when ectopically expressed in shoot meristem, converts shoot meristem to floral meristem. A nucleic acid molecule encoding a CAULIFLOWER gene product can be, for example, a nucleic acid molecule encoding Arabidopsis CAL shown in FIG. 5 (SEQ ID NO: 9) or a nucleic acid molecule encoding *Brassica oleracea* CAL shown in FIG. 6 (SEQ ID NO: 11). In comparison, a nucleic acid molecule encoding a truncated CAL gene product that terminates substantially before amino acid 255, such as the encoded truncated BobCAL gene product (SEQ ID NO: 13), is not a nucleic acid molecule encoding a CAL gene product as defined herein. Furthermore, ectopic expression of BobCAL in an angiosperm does not result in conversion of shoot meristem to floral meristem.

As used herein, the term "AP1 gene product" means a full-length AP1 gene product that does not terminate substantially before amino acid 256. A nucleic acid molecule encoding an AP1 gene product can be, for example, a nucleic acid molecule encoding Arabidopsis AP1 shown in FIG. 1 (SEQ ID NO: 1), *Brassica oleracea* AP1 shown in FIG. 2, (SEQ ID NO: 3), *Brassica oleracea* var. *botrytis* AP1 shown in FIG. 3 (SEQ ID NO: 5) or *Zea mays* AP1 shown in FIG. 4 (SEQ ID NO: 7).

The invention provides a CAL polypeptide having at least about 70 percent amino acid identity with amino acids 1 to 160 of SEQ ID NO: 10 or SEQ ID NO: 12. For example, the *Arabidopsis thaliana* CAL polypeptide, having the amino acid sequence shown as amino acids 1 to 255 in FIG. 5 (SEQ ID NO: 10), and the *Brassica oleracea* CAL polypeptide, having the amino acid sequence shown as amino acids 1 to 255 in FIG. 6 (SEQ ID NO: 12) are provided by the invention.

The invention also provides the truncated *Brassica oleracea* var. *botrytis* CAL polypeptide having the amino acid sequence shown as amino acids 1 to 150 in FIG. 7 (SEQ ID NO: 14). The BobCAL polypeptide can be useful as an immunogen to produce an antibody that specifically binds the truncated BoCAL polypeptide, but does not bind a full length CAL gene product. Such an antibody can be useful to distinguish between a full length CAL and truncated CAL.

The invention provides also provides a *Zea mays* AP1 polypeptide. As used herein, the term "polypeptide" is used in its broadest sense to include proteins, polypeptides and peptides, which are related in that each consists of a sequence of amino acids joined by peptide bonds. For convenience, the terms "polypeptide," "protein" and "gene product" are used interchangeably. While no specific attempt is made to distinguish the size limitations of a protein and a peptide, one skilled in the art would understand that proteins generally consist of at least about 50 to 100 amino acids and that peptides generally consist of at least two amino acids up to a few dozen amino acids. The term polypeptide is used generally herein to include any such amino acid sequence.

The term polypeptide also includes an active fragment of a floral meristem identity gene product. As used herein, the term "active fragment," means a polypeptide portion of a floral meristem identity gene product that can convert shoot meristem to floral meristem or can provide early flowering. For example, an active fragment of a CAL polypeptide can consist of an amino acid sequence derived from a CAL protein as shown in FIGS. 5 or 6 (SEQ ID NOS: 10 and 12) and that has an activity of a CAL. An active fragment can be, for example, an amino terminal or carboxyl terminal truncated form of *Arabidopsis thaliana* CAL or *Brassica oleracea* CAL (SEQ ID NOS: 10 or 12, respectively). Such an active fragment can be produced using well known recombinant DNA methods (Sambrook et al., supra, 1989). The product of the BobCAL gene, which is truncated at amino acid 150, lacks activity in converting shoot meristem to floral meristem and, therefore, is an example of a polypeptide portion of a CAL floral meristem identity gene product that is not an "active fragment."

An active fragment of a floral meristem identity gene product can convert shoot meristem to floral meristem and is readily identified using the methods described in Example II, below). Briefly, Arabidopsis can be transformed with a nucleic acid molecule encoding a portion of a floral meristem identity gene product, in order to determine whether the fragment can convert shoot meristem to floral meristem or promote early flowering and, therefore, has an activity of a floral meristem identity gene product.

The invention further provides an antibody that specifically binds a CAL polypeptide, an antibody that specifically binds the truncated *Brassica oleracea* var. *botrytis* CAL polypeptide, and an antibody that specifically binds the *Zea mays* AP1 polypeptide. As used herein, the term "antibody" is used in its broadest sense to include polyclonal and monoclonal antibodies, as well as polypeptide fragments of antibodies that retain a specific binding activity for CAL protein of at least about $1 \times 10^5$ $M^{-1}$. One skilled in the art would know that anti-CAL antibody fragments such as Fab, F(ab')$_2$ and Fv fragments can retain specific binding activity for CAL and, thus, are included within the definition of an antibody. In addition, the term "antibody" as used herein includes naturally occurring antibodies as well as non-naturally occurring antibodies and fragments that have binding activity such as chimeric antibodies or humanized antibodies. Such non-naturally occurring antibodies can be constructed using solid phase peptide synthesis, produced recombinantly or obtained, for example, by screening combinatorial libraries consisting of variable heavy chains and variable light chains as described by Huse et al., *Science* 246:1275–1281 (1989), which is incorporated herein by reference.

An antibody "specific for" a polypeptide, or that "specifically binds" a polypeptide, binds with substantially higher affinity to that polypeptide than to an unrelated polypeptide. An antibody specific for a polypeptide also can have specificity for a related polypeptide. For example, an antibody specific for Arabidopsis CAL also can have specificity for *Brassica oleracea* CAL.

An anti-CAL antibody, for example, can be prepared using a CAL fusion protein or a synthetic peptide encoding a portion of Arabidopsis CAL or of *Brassica oleracea* CAL as an immunogen. One skilled in the art would know that purified CAL protein, which can be prepared from natural sources or produced recombinantly, or fragments of CAL, including a peptide portion of CAL such as a synthetic peptide, can be used as an immunogen. Non-immunogenic fragments or synthetic peptides of CAL can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art and described, for example, by Harlow and Lane, *Antibodies: A laboratory manual* (Cold Spring Harbor Laboratory Press, 1988), which is incorporated herein by reference. An antibody that specifically binds the truncated Bob CAL polypeptide or an antibody that specifically binds the *Zea mays* AP1 polypeptide similarly can be produced using such methods. An antibody that specifically binds the truncated *Brassica oleracea* var. *botrytis* CAL polypeptide can be particularly useful to distinguish between full-length CAL polypeptide and truncated CAL polypeptide.

The invention provides a method of identifying a Brassica having a modified CAL allele by detecting a polymorphism associated with a CAL locus, where the CAL locus comprises a modified CAL allele that does not encode an active CAL gene product. Such a method is useful for the genetic improvement of Brassica plants, a genus of great economic value.

Brassica plants are a highly diverse group of crop plants useful as vegetables and as sources of condiment mustard, edible and industrial oil, animal fodder and green manure. Brassica crops encompass a variety of well known vegetables including cabbage, cauliflower, broccoli, collard, kale, mustard greens, Chinese cabbage and turnip, which can be interbred for crop improvement (see, for example, King, *Euphytica* 50:97–112 (1990) and Crisp and Tapsell, *Genetic improvement of vegetable crops* pp. 157–178 (1993), each of which is herein incorporated by reference).

Breeding of Brassica crops is useful, for example, for improving the quality and early development of vegetables. In addition, such breeding can be useful to increase disease resistance, such as resistance, of a Brassica to clubroot disease or mildew; viral resistance, such as resistance to turnip mosaic virus and cauliflower mosaic virus; or pest resistance (King, supra, 1990).

The use of polymorphic molecular markers in the breeding of Brassicae is well recognized in the art (Crisp and Tapsell, supra, 1993). Identification of a polymorphic molecular marker that is associated with a desirable trait can vastly accelerate the time required to breed the desirable trait into a new Brassica species or variant. In particular, since many rounds of backcrossing are required to breed a new trait into a different genetic background, early detection of a desirable trait by molecular methods can be performed prior to the time a plant is fully mature, thus accelerating the rate of crop breeding (see, for example, Figidore et al., *Euphytica* 69: 33–44 (1993), which is herein incorporated by reference).

A polymorphism associated with a CAL locus comprising a modified CAL allele that does not encode an active CAL gene product, is disclosed herein. FIG. 6 shows the nucleotide (SEQ ID NO: 11) and amino acid (SEQ ID NO: 12) sequence of *Brassica oleracea* CAL (BoCAL), and FIG. 7 shows the nucleotide (SEQ ID NO: 13) and amino acid (SEQ ID NO: 14) sequence of *Brassica oleracea* var. *botrytis* CAL (BobCAL). At amino acid 150, which is glutamic acid (Glu) in BOCAL, a stop codon is present in BobCAL. This polymorphism results in a truncated BobCAL gene product that is not active as a floral meristem identity gene product. The BoCAL nucleic acid sequence (ACGAGT) can be readily distinguished from the BobCAL nucleic acid sequence (ACTAGT) using well known molecular methods. For example, the polymorphic ACT- AGT BobCAL sequence is recognized by a SpeI restriction endonuclease site, whereas the ACGAGT BOCAL sequence is not recognized by SpeI. Thus, a restriction fragment length polymorphism (RFLP) in BobCAL provides a simple means for identifying a modified CAL allele (BobCAL) and, therefore, can serve as a marker to predict the inheritance of the "cauliflower" phenotype.

A modified CAL allele encoding a truncated CAL gene product also can serve as a marker to predict the "cauliflower" phenotype in other cauliflower variants. For example, nine romanesco variants of Brassica oleracea var. botrytis, which each have the "cauliflower" phenotype, were examined for the presence of a stop codon at position 151 of the CAL coding sequence. All nine of the romanesco variants contained the SpeI site that indicates a stop codon and, thus, a truncated CAL gene product. In contrast, Brassica oleracea variants that lack the "cauliflower" phenotype (broccoli and brussels sprouts) were examined for the SpeI site. In every case, the broccoli and brussel sprout variants had a full-length CAL coding sequence, as indicated by the absence of the distinguishing SpeI site. Thus, a truncated CAL gene product can be involved in the "cauliflower phenotype" in numerous different Brassica variants.

As used herein, the term "modified CAL allele" means a CAL allele that does not encode a CAL gene product active in converting shoot meristem to floral meristem. A modified CAL allele can have a modification within a gene regulatory element such that a CAL gene product is not produced. In addition, a modified CAL allele can have a modification such as a mutation, deletion or insertion in a CAL coding sequence which results in an inactive CAL gene product. For example, an inactive CAL gene product can result from a mutation creating a stop codon, such that a truncated, inactive CAL gene product lacking the ability to convert shoot meristem to floral meristem is produced.

As used herein, the term "associated" means closely linked and describes the tendency of two genetic loci to be inherited together as a result of their proximity. If two genetic loci are associated and are polymorphic, one locus can serve as a marker for the inheritance of the second locus. Thus, a polymorphism associated with a CAL locus comprising a modified CAL allele can serve as a marker for inheritance of the modified CAL allele. An associated polymorphism can be located in proximity to a CAL gene or can be located within a CAL gene.

A polymorphism in a nucleic acid sequence can be detected by a variety of methods. For example, if the polymorphism occurs in a particular restriction endonuclease site, the polymorphism can be detected by a difference in restriction fragment length observed following restriction with the particular restriction endonuclease and hybridization with a nucleotide sequence that is complementary to a nucleic acid sequence including a polymorphism.

The use of restriction fragment length polymorphism as an aid to breeding Brassicae is well known in the art (see, for example, Slocum et al., Theor. Appl. Genet. 80:57–64 (1990); Kennard et al., Theor. Appl. Genet. 87:721–732 (1994); and Figidore et al., supra, 1993, each of which is herein incorporated by reference). A restriction endonuclease such as SpeI, which is useful for identifying the presence of a BobCAL allele in an angiosperm, is readily available and can be purchased from a commercial source. Furthermore, a nucleotide sequence that is complementary to a nucleic acid sequence having a polymorphism associated with a CAL locus comprising a modified CAL allele can be derived, for example, from the nucleic acid molecule encoding Brassica oleracea var. botrytis CAL shown in FIG. 7 (SEQ ID NO: 13) or from the nucleic acid molecule encoding Brassica oleracea CAL shown in FIG. 6 (SEQ ID NO: 11).

In some cases, a polymorphism is not distinguishable by a RFLP, but nevertheless can be used to identify a Brassica having a modified CAL allele. For example, the polymerase chain reaction (PCR) can be used to detect a polymorphism associated with a CAL locus comprising a modified CAL allele. Specifically, a polymorphic region of a modified allele can be selectively amplified by using a primer that matches the nucleotide sequence of one allele of a polymorphic locus, but does not match the sequence of the second allele (Sobral and Honeycutt, The Polymerase Chain Reaction, pp. 304–319 (1994), which is herein incorporated by reference). Other well-known approaches for analyzing a polymorphism using PCR include discriminant hybridization of PCR-amplified DNA to allele-specific oligonucleotides and denaturing gradient gel electrophoresis (see Innis et al., supra, 1990).

The invention further provides a nucleic acid molecule encoding a chimeric protein, comprising a nucleic acid molecule encoding a floral meristem identity gene product such as AP1, LFY or CAL operably linked to a nucleic acid molecule encoding a ligand binding domain. Expression of a chimeric protein of the invention in an angiosperm is particularly useful because the ligand binding domain confers regulatable activity on a gene product such as a floral meristem identity gene product to which it is fused. Specifically, the floral meristem identity gene product component of the chimeric protein is inactive in the absence of the particular ligand, whereas, in the presence of ligand, the ligand binds the ligand binding domain, resulting in floral meristem identity gene product activity.

A nucleic acid molecule encoding a chimeric protein of the invention contains a nucleic acid molecule encoding a floral meristem identity gene product, such as a nucleic acid molecule encoding the amino acid sequence shown in FIG. 1 (SEQ ID NO: 2), in FIG. 5 (SEQ ID NO: 10), or in FIG. 9 (SEQ ID NO: 10), either of which is operably linked to a nucleic acid molecule encoding a ligand binding domain. The expression of such a nucleic acid molecule results in the production of a chimeric protein comprising a floral meristem identity gene product fused to a ligand binding domain. Thus, the invention also provides a chimeric protein comprising a floral meristem identity gene product fused to a ligand binding domain.

A ligand binding domain useful in a chimeric protein of the invention can be a steroid binding domain such as the ligand binding domain of a glucocorticoid receptor, estrogen receptor, progesterone receptor, androgen receptor, thyroid receptor, vitamin D receptor or retinoic acid receptor. A particularly useful ligand binding domain is a glucocorticoid receptor ligand binding domain, encompassed, for example, within amino acids 512 to 795 of the rat glucocorticoid receptor as shown in FIG. 16 (SEQ ID NO: 24; Miesfeld et al., Cell 46:389–399 (1986), which is incorporated herein by reference).

A chimeric protein containing a ligand binding domain, such as the rat glucocorticoid receptor ligand binding domain, confers glucocorticoid-dependent activity on the chimeric protein. For example, the activity of chimeric proteins consisting of adenovirus E1A, c-myc, c-fos, the HIV-1 Rev transactivator, MyoD or maize regulatory factor R fused to the rat glucocorticoid receptor ligand binding domain is regulated by glucocorticoid hormone (Eilers et al., *Nature* 340:66 (1989); Superti-Furga et al., *Proc. Natl. Acad. Sci.. U.S.A.* 88:5114 (1991); Hope et al., *Proc. Natl. Acad. Sci.. U.S.A.* 87:7787 (1990); Hollenberg et al., *Proc. Natl. Acad. Sci. U.S.A.* 90:8028 (1993), each of which is incorporated herein by reference).

Such a chimeric protein also can be regulated in plants. For example, a chimeric protein containing a heterologous protein fused to a rat glucocorticoid receptor ligand binding domain (amino acids 512 to 795) was expressed under the control of the constitutive cauliflower mosaic virus 35S promoter in Arabidopsis. The activity of the chimeric protein was inducible; the chimeric protein was inactive in the absence of ligand, and became active upon treatment of transformed plants with a synthetic glucocorticoid, dexamethasone (Lloyd et al., *Science* 266:436–439 (1994), which is incorporated herein by reference). As disclosed herein, a ligand binding domain fused to a floral meristem identity gene product can confer ligand inducibility on the activity of a fused floral meristem identity gene product in plants such that, upon exposure to a particular ligand, the floral meristem identity gene product is active.

Methods for constructing a nucleic acid molecule encoding a chimeric protein are routine and well known in the art (Sambrook et al., supra, 1989). For example, the skilled artisan would recognize that a stop codon in the 5' nucleic acid molecule must be removed and that the two nucleic acid molecules must be linked such that the reading frame of the 3' nucleic acid molecule is preserved. Methods of transforming plants with nucleic acid molecules also are well known in the art (see, for example, Mohoney et al., U.S. Pat. No. 5,463,174, and Barry et al., U.S. Pat. No. 5,463,175, each of which is incorporated herein by reference).

As used herein, the term "operably linked," when used in reference to two nucleic acid molecules comprising a nucleic acid molecule encoding a chimeric protein, means that the two nucleic acid molecules are linked in frame such that a full-length chimeric protein can be expressed. In particular, the 5' nucleic acid molecule, which encodes the amino-terminal portion of the chimeric protein, must be linked to the 3' nucleic acid molecule, which encodes the carboxyl-terminal portion of the chimeric protein, such that the carboxyl-terminal portion of the chimeric protein is produced in the correct reading frame.

The invention further provides a transgenic angiosperm containing a nucleic acid molecule encoding a chimeric protein, comprising a nucleic acid molecule encoding a floral meristem identity gene product such as AP1, CAL or LFY linked to a nucleic acid molecule encoding a ligand binding domain. Such a transgenic angiosperm is particularly useful because the angiosperm can be induced to flower by contacting the angiosperm with a ligand that binds the ligand binding domain. Thus, the invention provides a method of promoting early flowering or of converting shoot meristem to floral meristem in a transgenic angiosperm containing a nucleic acid molecule encoding a chimeric protein of the invention, comprising expressing the nucleic acid molecule encoding the chimeric protein in the angiosperm, and contacting the angiosperm with a ligand that binds the ligand binding domain, wherein binding of the ligand to the ligand binding domain activates the floral meristem identity gene product. In particular, the invention provides methods of promoting early flowering or of converting shoot meristem to floral meristem in a transgenic angiosperm containing a nucleic acid molecule encoding a chimeric protein that consists of a nucleic acid molecule encoding AP1 or CAL or LFY linked to a nucleic acid molecule encoding a glucocorticoid receptor ligand binding domain by contacting the transgenic angiosperm with a glucocorticoid such as dexamethasone.

As used herein, the term "ligand" means a naturally occurring or synthetic chemical or biological molecule such as a simple or complex organic molecule, a peptide, a protein or an oligonucleotide that specifically binds a ligand binding domain. A ligand of the invention can be used, alone, in solution or can be used in conjunction with an acceptable carrier that can serve to stabilize the ligand or promote absorption of the ligand by an angiosperm.

One skilled in the art can readily determine the optimum concentration of ligand needed to bind a ligand binding domain and render a floral meristem identity gene product active. Generally, a concentration of about 1 nM to 1 μM dexamethasone is useful for activating floral meristem identity gene product activity in a chimeric protein comprising a floral meristem identity gene product and a glucocorticoid receptor ligand binding domain (Lloyd et al., supra, 1994).

A transgenic angiosperm expressing a chimeric protein of the invention can be contacted with ligand in a variety of manners including, for example, by spraying, injecting or immersing the angiosperm. Further, a plant may be contacted with a ligand by adding the ligand to the plant's water supply or to the soil, whereby the ligand is absorbed into the angiosperm.

The following examples are intended to illustrate but not limit the present invention.

EXAMPLE I

Identification and characterization of the *Zea mays* APETALA1 cDNA

This example describes the isolation and characterization of the *Zea mays* ZAP-1 "gene", which is an ortholog of the Arabidopsis floral meristem identity gene, AP1.

A. Identification and characterization of a nucleic acid sequence encoding ZAP-1

The utility of using a cloned floral homeotic gene from Arabidopsis to identify the putative ortholog in maize has previously been demonstrated (Schmidt et al., supra, (1993), which is incorporated herein by reference). As described in Mena et al. (*Plant J.* 8(6):845–854 (1995)), the maize ortholog of the Arabidopsis AP1 floral meristem identity gene, was isolated by screening a *Zea mays* ear cDNA library using the Arabidopsis AP1 cDNA (SEQ ID NO: 1) as a probe. A cDNA library was prepared from wild-type immature ears as described by Schmidt et al., supra, 1993, using an Arabidopsis AP1 cDNA sequence as a probe. The Arabidopsis AP1 cDNA (SEQ ID NO: 1), which is shown in FIG. 1 (SEQ ID NO 1), was used as the probe. Low-stringency hybridizations with the AP1 probe were conducted as described previously for the isolation of ZAG1 using the AG cDNA as a probe (Schmidt et al., supra, 1993). Positive plaques were isolated and cDNAs were recovered in Bluescript by in vivo excision. Double-stranded sequencing was performed using the Sequenase Version 2.0 kit (U.S. Biochemical, Cleveland, Ohio) according to the manufacturer's protocol.

The cDNA sequence and deduced amino acid sequence for ZAP1 are shown in FIG. 4 (SEQ ID NOS: 7 and 8). The deduced amino acid sequence for ZAP1 shares 89% identity with Arabidopsis AP1 through the MADS domain (amino acids 1 to 57) and 70% identity through the first 160 amino acids, which includes the K domain. The high level of amino acid sequence identity between ZAP1 and AP1 (SEQ ID NOS: 8 and 2), as well as the expression pattern of ZAP1 in maize florets (see below), indicates that ZAP1 is the maize ortholog of Arabidopsis AP1.

B. RNA expression pattern of ZAP1

Total RNA was isolated from different maize tissues as described by Cone et al., *Proc. Natl. Acad. Sci., USA* 83:9631–9635 (1986), which is herein incorporated by reference. RNA was prepared from ears or tassels at early developing stages (approximately 2 cm in size), husk leaves from developing ear shoots, shoots and roots of germinated seedlings, leaves from 2 to 3 week old plants and endosperm, and embryos at 18 days after pollination. Mature floral organs were dissected from ears at the time of silk emergence or from tassels at several days pre-emergence. To study expression patterns in the mature female flower, carpels were isolated and the remaining sterile organs were pooled and analyzed together. In the same way, stamens were dissected and collected from male florets and the remaining organs (excluding the glumes) were pooled as one sample.

RNA concentration and purity was determined by absorbance at 260/280 nM, and equal amounts (10 μg) were fractionated on formaldehyde-agarose gels. Gels were stained in a solution of 0.125 μg ml$^{-1}$ acridine orange to confirm the integrity of the RNA samples and the uniformity of gel loading, then RNA was blotted on to Hybond-N® membranes (Amersham International, Arlington Heights, Ill.) according to the manufacturer's instructions. Prehybridization and hybridization solutions were prepared as previously described (Schmidt et al., *Science* 238:960–963 (1987), which is incorporated herein by reference). The probe for ZAP1 RNA expression studies was a 445 bp SacI-NsiI fragment from the 3' end of the cDNA. Southern blot analyses were conducted to establish conditions for specific hybridization of this probe. No cross-hybridization was detected with hybridization at 60° C. in 50% formamide and washes at 65° C. in 0.1× SSC and 0.5% SDS.

The strong sequence similarity between ZAP1 and AP1 indicated that ZAP1 was the ortholog of this Arabidopsis floral meristem identity gene. As a first approximation of whether the pattern of ZAP1 expression paralleled that of AP1, a blot of total RNA from vegetative and reproductive organs was hybridized with a gene-specific fragment of the ZAP1 cDNA (nucleotides 370 to 820 of SEQ ID NO: 7). ZAP1 RNA was detected only in male and female inflorescences and in the husk leaves that surround the developing ear. No ZAP1 RNA expression was detectable in RNA isolated from root, shoot, leaf, endosperm, or embryo tissue. The restriction of ZAP1 expression to terminal and axillary inflorescences is consistent with ZAP1 being the Arabidopsis AP1 ortholog.

Male and female florets were isolated from mature inflorescences, and the reproductive organs were separated from the remainder of the floret. RNA was isolated from the reproductive and the sterile portions of the florets. ZAP1 RNA expression was not detected in maize stamens or carpels, whereas high levels of ZAP1 RNA were present in developing ear and tassel florets from which the stamens and carpels had been removed. Thus, the exclusion of ZAP1 expression in stamens and carpels and its inclusion in the RNA of the non-reproductive portions of the floret (lodicules, lemma and palea) is similar to the pattern of expression of AP1 in flowers of Arabidopsis.

EXAMPLE II

Conversion of shoot meristem to floral meristem in an APETALA1 transgenic plant

This example describes methods for producing a transgenic Arabidopsis plant, in which shoot meristem is converted to floral meristem.

A. Ectopic expression of APETALA1 converts inflorescence shoots into flowers

Transgenic plants that constitutively express AP1 from the cauliflower mosaic virus 35S (CaMV35S) promoter were produced to determine whether ectopic AP1 expression could convert shoot meristem to floral meristem. The AP1 coding sequence was placed under control of the cauliflower mosaic virus 35S promoter (Odell et al., supra, 1985) as follows. BamHI linkers were ligated to the HincII site of the full-length AP1 complementary DNA (Mandel et al., supra, (1992), which is incorporated herein by reference) in pAM116, and the resulting BamHI fragment was fused to the cauliflower mosaic virus 35S promoter (Jack et al., *Cell* 76:703–716 (1994), which is incorporated herein by reference) in pCGN18 to create pAM563.

Transgenic AP1 Arabidopsis plants of the Columbia ecotype were generated by selecting kanamycin-resistant plants after Agrobacterium-mediated plant transformation using the in planta method (Bechtold et al., *C.R. Acad. Sci. Paris* 316:1194–1199 (1993), which is incorporated herein by reference). All analyses were performed in subsequent generations. Approximately 120 independent transgenic lines that displayed the described phenotypes were obtained.

Remarkably, in 35S-AP1 transgenic plants, the normally indeterminate shoot apex) prematurely terminated as a floral meristem and formed a terminal flower. In addition, all lateral meristems that normally would produce inflorescence shoots also were converted into solitary flowers. These results demonstrate that ectopic expression of AP1 in shoot meristem is sufficient to convert shoot meristem to floral meristem, even though AP1 normally is not absolutely required to specify floral meristem identity.

B. LEAFY is not required for the conversion of inflorescence shoots to flowers in an APETALA1 transgenic plant To determine whether the 35S-AP1 transgene causes ectopic LFY activity, and whether ectopic LFY activity is required for the conversion of shoot meristem to floral meristem, the 35S-AP1 transgene was introduced into Arabidopsis lfy mutants. The 35S-AP1 transgene was crossed into the strong lfy-6 mutant background and the $F_2$ progeny were analyzed.

Lfy mutant plants containing the 35S-AP1 transgene displayed the same conversion of apical and lateral shoot meristem to floral meristem as was observed in transgenics containing wild type LFY. However, the resulting flowers had the typical lfy mutant phenotype, in which floral organs developed as sepaloid and carpelloid structures, with an absence of petals and stamens. These results demonstrate that LFY is not required for the conversion of shoot meristem to floral meristem in a transgenic angiosperm that ectopically expresses AP1.

C. APETALA1 is not sufficient to specify organ fate

As well as being involved in the early step of specifying floral meristem identity, AP1 also is involved in specifying sepal and petal identity at a later stage in flower development. Although AP1 RNA is initially expressed throughout the young flower primordium, it is later excluded from stamen and carpel primordia (Mandel et al., *Nature* 360:273–277 (1992)). Since the cauliflower mosaic virus 35S promoter is active in all floral organs, 35S-AP1 transgenic plants are likely to ectopically express AP1 in stamens and carpels. However, 35S-AP1 transgenic plants had normal stamens and carpels, indicating that AP1 is not sufficient to specify sepal and petal organ fate.

D. Ectopic expression of APETALA1 causes early flowering

In addition to its ability to alter inflorescence meristem identity, ectopic expression of AP1 also influences the vegetative phase of plant growth. Wild-type plants have a vegetative phase during which a basal rosette of leaves is produced, followed by the transition to reproductive growth. The transition from vegetative to reproductive growth was measured both in terms of the number of days post-germination until the first visible flowers were observed, and by counting the number of leaves. Under continuous light, wild-type and 35S-AP1 transgenic plants flowered after producing 9.88±1.45 and 4.16±0.97 leaves, respectively. Under short-day growth conditions (8 hours light, 16 hours dark, 24 C.), wild-type and 35S-AP1 transgenic plants flowered after producing 52.42±3.47 and 7.4±1.18 leaves, respectively.

In summary, under continuous light growth conditions, flowers appear on wild-type Arabidopsis plants after approximately 18 days, whereas the 35S-AP1 transgenic plants flowered after an average of only 10 days. Furthermore, under short-day growth conditions, flowering is delayed in wild-type plants until approximately 10 weeks after germination, whereas, 35S-AP1 transgenic plants flowered in less than 3 weeks. Thus, ectopic AP1 activity significantly reduced the time to flowering and reduced the delay of flowering caused by short day growth conditions.

EXAMPLE III

Isolation and characterization of the Arabidopsis and *Brassica oleracea* CAULIFLOWER genes This example describes methods for isolating and characterizing the Arabidopsis and *Brassica oleracea* CAL genes.

A. Isolation of the Arabidopsis and *Brassica oleracea* CAULIFLOWER genes

Genetic evidence that CAL and AP1 proteins may be functionally related indicated that these proteins may share similar DNA sequences. In addition, DNA blot hybridization revealed that the Arabidopsis genome contains a gene that is closely related to AP1. The CAL gene, which is closely related to AP1, was isolated and identified as a member of the family of Arabidopsis MADS domain genes known as the AGAMOUS-like (AGL) genes.

Hybridization with an AP1 probe was used to isolate a 4.8-kb Eco RI genomic fragment of CAL. The corresponding CAL complementary DNA (pBS85) was cloned by reverse transcription-polymerase chain reaction (RT-PCR) with the oligonucleotides AGL10-1 (5'-GATCGTCGTTATCTCTCTTG-3'; SEQ ID NO: 25) and AGL10-12 (5'-GTAGTCTATTCAAGCGGCG-3'; SEQ ID NO: 26).

The Arabidopsis CAL cDNA encodes a putative 255 amino acid protein (FIG. 5; SEQ ID NO: 10) having a calculated molecular weight of 30.1 kD and an isoelectric point of 8.78. The deduced amino acid sequence for CAL contains a MADS domain which generally is present in a class of transcription factors. The MADS domains of CAL and AP1 were markedly similar, differing in only 5 of 56 amino acid residues, 4 of which represent conservative replacements. Overall, the putative CAL protein is 76% identical to AP1; with allowance for conservative amino acid substitutions, the two proteins are 88% similar. These results indicate that CAL and AP1 may recognize similar target sequences and regulate many of the same genes involved in floral meristems identity.

CAL was mapped to the approximate location of the loci identified by classical genetic means for the cauliflower phenotype (Bowman et al., *Development* 119:721 (1993), which is herein incorporated by reference). Restriction fragment length polymorphism (RFLP) mapping filters were scored and the results analyzed with the Macintosh version of the Mapmaker program as described by Rieter et al., (*Proc. Natl. Acad. Sci., USA*, 89:1477 (1992), which is herein incorporated by reference). The results localized CAL to the upper arm of chromosome 1, near marker λ235.

A genomic fragment spanning the CAL gene was used to transform cal-1 ap1-1 plants. A 5850-bp Bam HI fragment containing the entire coding region of the Arabidopsis CAL gene as well as 1860 bp upstream of the putative translational start site was inserted into the pBIN19 plant transformation vector (Clontech, Palo Alto, Calif.) and used for transformation of root tissue from cal-1 ap1-1 plants as described by Valvekens et al. (*Proc. Natl. Acad. Sci.. USA* 85:5536 (1988), which is incorporated herein by reference). Seeds were harvested from primary transformants, and all phenotypic analyses were performed in subsequent generations. Four independent lines transformed with CAL showed a complementation of the cauliflower (cal) phenotype and displayed a range of phenotypes similar to those exhibited by ap1 mutants. These results demonstrated that CAL functions to convert shoot meristem to floral meristem.

In order to identify regions of functional importance in the CAL protein, cal mutants were generated and analyzed. The cal alleles were isolated by mutagenizing seeds homozygous for the ap1-1 allele in Ler with 0.1% or 0.05% ethylmethane sulfonate (EMS) for 16 hours. Putative new cal alleles were crossed to cal-1 ap1-1 chlorina plants to verify allelism. Two sets of oligonucleotides were used to amplify and clone new alleles: oligos AGL10-1 (SEQ ID NO: 25) and AGL10-2 (5'-GATGGAGACCATTAAACAT-3; SEQ ID NO: 27) for the 5' portion and oligos AGL10-3 (5'-GGAGAAGGTACTAGAACG-3'; SEQ ID NO: 28) and AGL10-4 (5'-GCCCTCTTCCATAGATCC-3'; SEQ ID NO: 29) for the 3' portion of the gene. All coding regions and intron-exon boundaries of the mutant alleles were sequenced.

Sequence analysis of the cal-1 allele, which exists in the wild-type Wassilewskija (WS) ectoype, revealed a cluster of three amino acid differences in the seventh exon, relative to the wild-type gene product from Landsberg erecta (Ler) (FIG. 8). One or more of these amino acid differences can be responsible for the cal phenotype, because the cal-1 gene was expressed normally and the transcribed RNA was correctly spliced in the WS background. The three additional cal alleles that were isolated, designated cal-2, cal-3, and cal-4, exhibited phenotypes similar to that of the cal-1 allele.

Sequence analyses revealed a single missense mutation for each (FIG. 8). Since mutations in the cal-2 and cal-3 alleles lie in the MADS domain, these mutations can affect the ability of CAL to bind DNA and activate its target genes. Because the cal-4 allele contains a substitution in the K domain, a motif thought to be involved in protein-protein interactions, this mutation can affect the ability of CAL to form homodimers or to interact with other proteins such as AP1.

B. RNA expression pattern of CAULIFLOWER

To characterize the temporal and spatial pattern of CAL RNA accumulation, RNA in situ hybridizations were performed using a CAL-specific probe. $^{35}$S-labeled antisense CAL and BOCAL mRNA was synthesized from Sca 1-digested cDNA templates and hybridized to 8 µm sections of Arabidopsis Ler or *Brassica oleracea* inflorescences. The probes did not contain any MADS box sequences in order to avoid cross-hybridization with other MADS box genes. Hybridization conditions were as previously described (Drews et al., *Cell* 65:991 (1991), which is herein incorporated by reference).

As with AP1, CAL RNA accumulated in young flower primordia, consistent with the ability of CAL to substitute for AP1 in specifying floral meristems. In contrast to AP1 RNA, however, which accumulated at high levels throughout sepal and petal development, CAL RNA was detected only at very low levels in these organs. These results demonstrate that CAL was unable to substitute for AP1 in specifying sepals and petals, at least in part as a result of the relatively low levels of CAL RNA in these developing organs.

C. Molecular Basis of the cauliflower phenotype

The cal phenotype in Arabidopsis is similar to the inflorescence structure that develops in the closely related species *Brassica oleracea* var. *botrytis*, the cultivated garden variety of cauliflower, indicating that the CAL gene can contribute to the cal phenotype of this agriculturally important species. Thus, CAL gene homologs were isolated from a *Brassica oleracea* line that produces wild-type flowers (BoCAL) and from the common garden variety of cauliflower *Brassica oleracea* var. *botrytis* (BobCAL).

The single-copy BobCAL gene (Snowball Y Improved, NK Lawn & Garden, Minneapolis, Minn.) was isolated from a size-selected genomic library in λBlueStar (Novagen) on a 16-kbp BamHI fragment with the Arabidopsis CAL gene as a probe. The BOCAL gene was isolated from a rapid cycling line (Williams and Hill, *Science* 232:1385 (1986)) by PCR on both RNA and genomic DNA. The cDNA was isolated by RT-PCR using the oligonucleotides: Bob1 (5'-TCTACGAGAAATGGGAAGG-3'; SEQ ID NO: 30) and Bob2 (5'-GTCGATATATGGCGAGTCC-3'; SEQ ID NO: 31). The 5' portion of the gene was obtained using oligonucleotides Bob 1 (SEQ ID NO: 30) and Bob4B (5'-CCATTGACCAGTTCGTTTG-3'; SEQ ID NO: 32). The 3' portion was obtained using oligonucleotides Bob3 (5'-GCTCCAGACTCTCACGTC-3'; SEQ ID NO: 33) and Bob2 (SEQ ID NO: 31).

RNA in situ hybridizations were performed to determine the expression pattern of BOCAL gene from *Brassica oleracea*. As in Arabidopsis, BoCAL RNA accumulated uniformly in early floral primordia and later was excluded from the cells that give rise to stamens and carpels.

DNA sequence analyses revealed that the open reading frame of the BoCAL gene is intact, whereas that of the BobCAL gene is interrupted by a stop codon in exon 5 (FIG. 8). Translation of the resulting BobCAL protein product is truncated after only 150 of the wild-type 255 amino acids. Because similar stop codon mutations in the fifth exon of the Arabidopsis AP1 coding sequence result in plants having a severe ap1 phenotype, the BobCAL protein likely is not functional. These results indicate that, as in Arabidopsis, the molecular basis for the cauliflower phenotype in *Brassica oleracea* var. *botrytis* is due, at least in part, to a mutation in the BobCAL gene.

EXAMPLE IV

Conversion of inflorescence shoots into flowers in an CAULIFLOWER transgenic plant This example describes methods for producing a transgenic CAL plant.

A. Ectopic expression of CAULIFLOWER converts inflorescence shoots to flowers

Transgenic Arabidopsis plants that ectopically express CAL in shoot meristem were generated. The full-length CAL cDNA was inserted downstream of the 35S cauliflower mosaic virus promoter in the EcoRI of pMON530 (Monsanto Co. Co., St. Louis, Mo.) This plasmid was introduced into Agrobacterium strain ASE (check) and used to transform the Columbia ecotype of Arabidopsis using a modified vacuum infiltration method described by Bechtold et al. (supra, 1993). The 96 lines generated that harbored the 35S-CAL construct had a range of weak to strong phenotypes. The transgenic plants with the strongest phenotypes (27 lines) closely resembled the tfl mutant.

35S-CAL transgenic plants had converted apical and lateral inflorescence shoots into flowers and showed an early flowering phenotype. These results demonstrate that CAL is sufficient for the conversion of shoots to flowers and for promoting early flowering.

EXAMPLE V

Conversion of shoots into flowers in a LEAFY transgenic plant

This example describes methods for producing a transgenic LFY Arabidopsis and aspen.

A. Conversion of Arabidopsis shoots by LEAFY

Transgenic Arabidopsis plants were generated by transforming Arabidopsis with LFY under the control of the cauliflower mosaic virus 35S promoter (CaMV35S) (Odell et al., supra, (1985)). A LFY complementary cDNA (Weigel et al, *Cell* 69:843–859 (1992), which is incorporated herein by reference) was inserted into a T-DNA transformation vector containing a CaMV 35S promoter/3' nos cassette (Jack et al., supra, 1994). Transformed seedlings were selected for kanamycin resistance. Several hundred transformants in three different genetic backgrounds (Nossen, Wassilewskija and Columbia) were recovered and several lines were characterized in detail.

High levels of LFY RNA expression were detected by northern blot analysis. In general, Nossen lines had weaker phenotypes, especially when grown in short days. The 35S-LFY transgene of line DW151.117 (ecotype Wassilewskija) was introgressed into the erecta background by backcrossing to a Landsberg erecta strain. Plants were grown under 16 hours light and 8 hours dark. The 35S-LFY transgene provided at least as much LFY activity as the endogenous gene and completely suppressed the lfy mutant phenotype when crossed into the background of the lfy-6 null allele.

Most 35S-LFY transgenic plants lines demonstrated a very similar, dominant and heritable phenotype. Secondary shoots that arose in lateral positions were consistently replaced by solitary flowers, and higher-order shoots were absent. Although the number of rosette leaves was unchanged from the wild type, 35S-LFY plants flowered earlier than wild type; the solitary flowers in the axils of the rosette leaves developed and opened precociously. In addition, the primary shoot terminated with a flower. In the most extreme cases, a terminal flower was formed immediately above the rosette. This gain of function phenotype (conversion of shoots to flowers) is the opposite of the lfy loss of function phenotype (conversion of flowers to shoots). These results demonstrate that LFY encodes a developmental switch that is both sufficient and necessary to convert shoot meristem to flower meristem.

The effects of constitutive LFY expression differ for primary and secondary shoot meristems. Secondary meristems were transformed into flower meristem, apparently as soon as it developed, and produced only a single, solitary flower. In contrast, primary shoot meristem produced leaves and lateral flowers before being consumed in the formation of a terminal flower. These developmental differences indicate that a meristem must acquire competence to respond to the activity of a floral meristem identity gene such as LFY.

B. Conversion of aspen shoots by LEAFY

Given that constitutive expression of LFY induced precocious flowering during the vegetative phase of Arabidopsis, the effect of LFY on the flowering of other species was examined. The perennial tree, hybrid aspen, is derived from parental species that flower naturally only after 8–20 years of growth (Schopmeyer (ed.), *USDA Agriculture Handbook* 450: *Seeds of Woody Plants in the United States*, Washington D.C., USA: U.S. Government Printing Office, pp. 645–655 (1974)). 35S-LFY aspen plants were obtained by Agrobacterium-mediated transformation of stem segments and subsequent regeneration of transgenic shoots in tissue culture.

Hybrid aspen was transformed exactly as described by Nilsson et al. (*Transgen. Res.* 1:209–220 (1992), which is incorporated herein by reference). Levels of LFY RNA expression were similar to those of 35S-LFY Arabidopsis, as determined by northern blot analysis. The number of vegetative leaves varied between different regenerating shoots, and those with a higher number of vegetative leaves formed roots, allowing for transfer to the greenhouse. Individual flowers were removed either from primary transformants that had been transferred to the greenhouse, or from catkins collected in spring, 1995, at Carlshem, Umeå, Sweden) from a tree whose age was determined by counting the number of annual rings in a core extracted with an increment borer at 1.5 meters above ground level. Flowers were fixed in formaldehyde/acetic acid/ethanol and destained in ethanol before photography.

The overall phenotype of 35S-LFY aspen was similar to that of 35S-LFY Arabidopsis. In wild-type plants of both species, flowers normally are formed in lateral positions on inflorescence shoots. In aspen, these inflorescence shoots, called catkins, arise from the leaf axils of adult trees. In both 35S-LFY Arabidopsis and 35S-LFY aspen, solitary flowers were formed instead of shoots in the axils of vegetative leaves. Moreover, as in Arabidopsis, the secondary shoots of trangenic aspen were more severely affected than the primary shoot.

Regenerating 35S-LFY aspen shoots initially produced solitary flowers in the axils of normal leaves. However, the number of vegetative leaves was limited, and the shoot meristem was prematurely consumed in the formation of an aberrant terminal flower. Precocious flower development was specific to 35S-LFY transformants and was not observed in non-transgenic controls. Furthermore, not a single instance of precocious flower development has been observed in more than 1,500 other lines of transgenic aspen generated with various constructs from 1989 to 1995 at the Swedish University of Agricultural Sciences. These results demonstrate that a heterologous floral meristem identity gene product is active in an angiosperm.

Although the invention has been described with reference to the examples above, it should be understood that various modifications can be made without departing from the spirit of the invention. Accordingly, the invention is limited only by the following claims.

---

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 1215 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: join(141..905, 909..971, 975..1047)

( i x ) FEATURE:
        ( A ) NAME/KEY: misc_feature
        ( B ) LOCATION: 1..1215
        ( D ) OTHER INFORMATION: /note= "product = Arabidopsis thaliana AP1"

( x i ) SEQUENCE DESCRIPTION: SEQ ID NO:1:

```
GAATTCCTCG  AGCTACGTCA  GGGCCCTGAC  GTAGCTCGAA  GTCGAGCTC  TTCTTTATAT         60

CTCTCTTGTA  GTTTCTTATT  GGGGGTCTTT  GTTTGTTTG  GTTCTTTTAG  AGTAAGAAGT        120

TTCTTAAAAA  AGGATCAAAA  ATG  GGA  AGG  GGT  AGG  GTT  CAA  TTG  AAG  AGG    170
                           Met  Gly  Arg  Gly  Arg  Val  Gln  Leu  Lys  Arg
                            1                 5                          10

ATA  GAG  AAC  AAG  ATC  AAT  AGA  CAA  GTG  ACA  TTC  TCG  AAA  AGA  AGA  GCT      218
Ile  Glu  Asn  Lys  Ile  Asn  Arg  Gln  Val  Thr  Phe  Ser  Lys  Arg  Arg  Ala
              15                          20                         25

GGT  CTT  TTG  AAG  AAA  GCT  CAT  GAG  ATC  TCT  GTT  CTC  TGT  GAT  GCT  GAA      266
```

-continued

| | | | | | | | | | | | | | | | |
|---|---|---|---|---|---|---|---|---|---|---|---|---|---|---|---|
|Gly|Leu|Leu|Lys|Lys|Ala|His|Glu|Ile|Ser|Val|Leu|Cys|Asp|Ala|Glu|
| | |  |30 |   |   |   |   |35 |   |   |   |   |40 |   |   |

```
GTT  GCT  CTT  GTT  GTC  TTC  TCC  CAT  AAG  GGA  AAA  CTC  TTC  GAA  TAC  TCC       314
Val  Ala  Leu  Val  Val  Phe  Ser  His  Lys  Gly  Lys  Leu  Phe  Glu  Tyr  Ser
               45                      50                      55

ACT  GAT  TCT  TGT  ATG  GAG  AAG  ATA  CTT  GAA  CGC  TAT  GAG  AGG  TAC  TCT       362
Thr  Asp  Ser  Cys  Met  Glu  Lys  Ile  Leu  Glu  Arg  Tyr  Glu  Arg  Tyr  Ser
          60                      65                      70

TAC  GCC  GAA  AGA  CAG  CTT  ATT  GCA  CCT  GAG  TCC  GAC  GTC  AAT  ACA  AAC       410
Tyr  Ala  Glu  Arg  Gln  Leu  Ile  Ala  Pro  Glu  Ser  Asp  Val  Asn  Thr  Asn
75                      80                      85                           90

TGG  TCG  ATG  GAG  TAT  AAC  AGG  CTT  AAG  GCT  AAG  ATT  GAG  CTT  TTG  GAG       458
Trp  Ser  Met  Glu  Tyr  Asn  Arg  Leu  Lys  Ala  Lys  Ile  Glu  Leu  Leu  Glu
               95                      100                     105

AGA  AAC  CAG  AGG  CAT  TAT  CTT  GGG  GAA  GAC  TTG  CAA  GCA  ATG  AGC  CCT       506
Arg  Asn  Gln  Arg  His  Tyr  Leu  Gly  Glu  Asp  Leu  Gln  Ala  Met  Ser  Pro
               110                     115                     120

AAA  GAG  CTT  CAG  AAT  CTG  GAG  CAG  CAG  CTT  GAC  ACT  GCT  CTT  AAG  CAC       554
Lys  Glu  Leu  Gln  Asn  Leu  Glu  Gln  Gln  Leu  Asp  Thr  Ala  Leu  Lys  His
               125                     130                     135

ATC  CGC  ACT  AGA  AAA  AAC  CAA  CTT  ATG  TAC  GAG  TCC  ATC  AAT  GAG  CTC       602
Ile  Arg  Thr  Arg  Lys  Asn  Gln  Leu  Met  Tyr  Glu  Ser  Ile  Asn  Glu  Leu
     140                     145                     150

CAA  AAA  AAG  GAG  AAG  GCC  ATA  CAG  GAG  CAA  AAC  AGC  ATG  CTT  TCT  AAA       650
Gln  Lys  Lys  Glu  Lys  Ala  Ile  Gln  Glu  Gln  Asn  Ser  Met  Leu  Ser  Lys
155                     160                     165                          170

CAG  ATC  AAG  GAG  AGG  GAA  AAA  ATT  CTT  AGG  GCT  CAA  CAG  GAG  CAG  TGG       698
Gln  Ile  Lys  Glu  Arg  Glu  Lys  Ile  Leu  Arg  Ala  Gln  Gln  Glu  Gln  Trp
               175                     180                     185

GAT  CAG  CAG  AAC  CAA  GGC  CAC  AAT  ATG  CCT  CCC  CCT  CTG  CCA  CCG  CAG       746
Asp  Gln  Gln  Asn  Gln  Gly  His  Asn  Met  Pro  Pro  Pro  Leu  Pro  Pro  Gln
               190                     195                     200

CAG  CAC  CAA  ATC  CAG  CAT  CCT  TAC  ATG  CTC  TCT  CAT  CAG  CCA  TCT  CCT       794
Gln  His  Gln  Ile  Gln  His  Pro  Tyr  Met  Leu  Ser  His  Gln  Pro  Ser  Pro
               205                     210                     215

TTT  CTC  AAC  ATG  GGT  GGT  CTG  TAT  CAA  GAA  GAT  GAT  CCT  ATG  GCA  ATG       842
Phe  Leu  Asn  Met  Gly  Gly  Leu  Tyr  Gln  Glu  Asp  Asp  Pro  Met  Ala  Met
220                     225                     230

AGG  AAT  GAT  CTC  GAA  CTG  ACT  CTT  GAA  CCC  GTT  TAC  AAC  TGC  AAC  CTT       890
Arg  Asn  Asp  Leu  Glu  Leu  Thr  Leu  Glu  Pro  Val  Tyr  Asn  Cys  Asn  Leu
235                     240                     245                          250

GGC  TGC  TTC  GCC  GCA  TGA  AGC  ATT  TCC  ATA  TAT  ATA  TTT  GTA  ATC  GTC       938
Gly  Cys  Phe  Ala  Ala       Ser  Ile  Ser  Ile  Tyr  Ile  Phe  Val  Ile  Val
               255                     260                          265

AAC  AAT  AAA  AAC  AGT  TTG  CCA  CAT  ACA  TAT  AAA  TAG  TGG  CTA  GGC  TCT       986
Asn  Asn  Lys  Asn  Ser  Leu  Pro  His  Thr  Tyr  Lys       Trp  Leu  Gly  Ser
               270                     275                                   280

TTT  CAT  CCA  ATT  AAT  ATA  TTT  TGG  CAA  ATG  TTC  GAT  GTT  CTT  ATA  TCA      1034
Phe  His  Pro  Ile  Asn  Ile  Phe  Trp  Gln  Met  Phe  Asp  Val  Leu  Ile  Ser
               285                     290                     295

TCA  TAT  ATA  AATTAGCAGG  CTCCTTCTT   CTTTTGTAAT  TTGATAAGTT                       1083
Ser  Tyr  Ile  Asn
               300

TATTTGCTTC  AATATGGAGC  AAAATTGTAA  TATATTTGAA  GGTCAGAGAG  AATGAACGTG              1143

AACTTAATAG  AAAAAAAAAA  AAAAAAAAAA  AAAAAAAAAA  AAAAAAAAAA  CCCGACGTAG              1203

CTCGAGGAAT  TC                                                                      1215
```

( 2 ) INFORMATION FOR SEQ ID NO:2:

(i) SEQUENCE CHARACTERISTICS:
(A) LENGTH: 300 amino acids
(B) TYPE: amino acid
(D) TOPOLOGY: linear (ii) MOLECULE TYPE: protein (xi) SEQUENCE DESCRIPTION: SEQ ID NO:2:

| Met | Gly | Arg | Gly | Arg | Val | Gln | Leu | Lys | Arg | Ile | Glu | Asn | Lys | Ile | Asn |
|---|---|---|---|---|---|---|---|---|---|---|---|---|---|---|---|
| 1 | | | | 5 | | | | | 10 | | | | | 15 | |

| Arg | Gln | Val | Thr | Phe | Ser | Lys | Arg | Arg | Ala | Gly | Leu | Leu | Lys | Lys | Ala |
|---|---|---|---|---|---|---|---|---|---|---|---|---|---|---|---|
| | | | 20 | | | | | 25 | | | | | 30 | | |

| His | Glu | Ile | Ser | Val | Leu | Cys | Asp | Ala | Glu | Val | Ala | Leu | Val | Val | Phe |
|---|---|---|---|---|---|---|---|---|---|---|---|---|---|---|---|
| | | 35 | | | | | 40 | | | | | 45 | | | |

| Ser | His | Lys | Gly | Lys | Leu | Phe | Glu | Tyr | Ser | Thr | Asp | Ser | Cys | Met | Glu |
|---|---|---|---|---|---|---|---|---|---|---|---|---|---|---|---|
| | 50 | | | | | 55 | | | | | 60 | | | | |

| Lys | Ile | Leu | Glu | Arg | Tyr | Glu | Arg | Tyr | Ser | Tyr | Ala | Glu | Arg | Gln | Leu |
|---|---|---|---|---|---|---|---|---|---|---|---|---|---|---|---|
| 65 | | | | | 70 | | | | | 75 | | | | | 80 |

| Ile | Ala | Pro | Glu | Ser | Asp | Val | Asn | Thr | Asn | Trp | Ser | Met | Glu | Tyr | Asn |
|---|---|---|---|---|---|---|---|---|---|---|---|---|---|---|---|
| | | | | 85 | | | | | 90 | | | | | 95 | |

| Arg | Leu | Lys | Ala | Lys | Ile | Glu | Leu | Leu | Glu | Arg | Asn | Gln | Arg | His | Tyr |
|---|---|---|---|---|---|---|---|---|---|---|---|---|---|---|---|
| | | | 100 | | | | | 105 | | | | | 110 | | |

| Leu | Gly | Glu | Asp | Leu | Gln | Ala | Met | Ser | Pro | Lys | Glu | Leu | Gln | Asn | Leu |
|---|---|---|---|---|---|---|---|---|---|---|---|---|---|---|---|
| | | | 115 | | | | | 120 | | | | | 125 | | |

| Glu | Gln | Gln | Leu | Asp | Thr | Ala | Leu | Lys | His | Ile | Arg | Thr | Arg | Lys | Asn |
|---|---|---|---|---|---|---|---|---|---|---|---|---|---|---|---|
| | 130 | | | | | 135 | | | | | 140 | | | | |

| Gln | Leu | Met | Tyr | Glu | Ser | Ile | Asn | Glu | Leu | Gln | Lys | Lys | Glu | Lys | Ala |
|---|---|---|---|---|---|---|---|---|---|---|---|---|---|---|---|
| 145 | | | | | 150 | | | | | 155 | | | | | 160 |

| Ile | Gln | Glu | Gln | Asn | Ser | Met | Leu | Ser | Lys | Gln | Ile | Lys | Glu | Arg | Glu |
|---|---|---|---|---|---|---|---|---|---|---|---|---|---|---|---|
| | | | | 165 | | | | | 170 | | | | | 175 | |

| Lys | Ile | Leu | Arg | Ala | Gln | Gln | Glu | Gln | Trp | Asp | Gln | Gln | Asn | Gln | Gly |
|---|---|---|---|---|---|---|---|---|---|---|---|---|---|---|---|
| | | | | 180 | | | | | 185 | | | | | 190 | |

| His | Asn | Met | Pro | Pro | Pro | Leu | Pro | Pro | Gln | Gln | His | Gln | Ile | Gln | His |
|---|---|---|---|---|---|---|---|---|---|---|---|---|---|---|---|
| | | | 195 | | | | | 200 | | | | | 205 | | |

| Pro | Tyr | Met | Leu | Ser | His | Gln | Pro | Ser | Pro | Phe | Leu | Asn | Met | Gly | Gly |
|---|---|---|---|---|---|---|---|---|---|---|---|---|---|---|---|
| | 210 | | | | | 215 | | | | | 220 | | | | |

| Leu | Tyr | Gln | Glu | Asp | Asp | Pro | Met | Ala | Met | Arg | Asn | Asp | Leu | Glu | Leu |
|---|---|---|---|---|---|---|---|---|---|---|---|---|---|---|---|
| 225 | | | | | 230 | | | | | 235 | | | | | 240 |

| Thr | Leu | Glu | Pro | Val | Tyr | Asn | Cys | Asn | Leu | Gly | Cys | Phe | Ala | Ala | Ser |
|---|---|---|---|---|---|---|---|---|---|---|---|---|---|---|---|
| | | | | 245 | | | | | 250 | | | | | 255 | |

| Ile | Ser | Ile | Tyr | Ile | Phe | Val | Ile | Val | Asn | Asn | Lys | Asn | Ser | Leu | Pro |
|---|---|---|---|---|---|---|---|---|---|---|---|---|---|---|---|
| | | | 260 | | | | | 265 | | | | | 270 | | |

| His | Thr | Tyr | Lys | Trp | Leu | Gly | Ser | Phe | His | Pro | Ile | Asn | Ile | Phe | Trp |
|---|---|---|---|---|---|---|---|---|---|---|---|---|---|---|---|
| | | 275 | | | | | 280 | | | | | 285 | | | |

| Gln | Met | Phe | Asp | Val | Leu | Ile | Ser | Ser | Tyr | Ile | Asn | | | | |
|---|---|---|---|---|---|---|---|---|---|---|---|---|---|---|---|
| | 290 | | | | | 295 | | | | | 300 | | | | |

(2) INFORMATION FOR SEQ ID NO:3:

(i) SEQUENCE CHARACTERISTICS:
(A) LENGTH: 794 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 36..794

( i x ) FEATURE:
 ( A ) NAME/KEY: misc_feature
 ( B ) LOCATION: 1..794
 ( D ) OTHER INFORMATION: /note= "product = Brassica oleracea AP1"

( x i ) SEQUENCE DESCRIPTION: SEQ ID NO:3:

```
TCTTAGAGGA AATAGTTCCT TTAAAAGGGA TAAAA ATG GGA AGG GGT AGG GTT              53
                                      Met Gly Arg Gly Arg Val
                                       1                   5

CAG TTG AAG AGG ATA GAA AAC AAG ATC AAT AGA CAA GTG ACA TTC TCG            101
Gln Leu Lys Arg Ile Glu Asn Lys Ile Asn Arg Gln Val Thr Phe Ser
             10                  15                  20

AAA AGA AGA GCT GGT CTT ATG AAG AAA GCT CAT GAG ATC TCT GTT CTG            149
Lys Arg Arg Ala Gly Leu Met Lys Lys Ala His Glu Ile Ser Val Leu
             25                  30                  35

TGT GAT GCT GAA GTT GCG CTT GTT GTC TTC TCC CAT AAG GGG AAA CTC            197
Cys Asp Ala Glu Val Ala Leu Val Val Phe Ser His Lys Gly Lys Leu
         40                  45                  50

TTT GAA TAC TCC ACT GAT TCT TGT ATG GAG AAG ATA CTT GAA CGC TAT            245
Phe Glu Tyr Ser Thr Asp Ser Cys Met Glu Lys Ile Leu Glu Arg Tyr
 55                  60                  65                  70

GAG AGA TAC TCT TAC GCC GAG AGA CAG CTT ATA GCA CCT GAG TCC GAC            293
Glu Arg Tyr Ser Tyr Ala Glu Arg Gln Leu Ile Ala Pro Glu Ser Asp
                 75                  80                  85

TCC AAT ACG AAC TGG TCG ATG GAG TAT AAT AGG CTT AAG GCT AAG ATT            341
Ser Asn Thr Asn Trp Ser Met Glu Tyr Asn Arg Leu Lys Ala Lys Ile
             90                  95                 100

GAG CTT TTG GAG AGA AAC CAG AGG CAC TAT CTT GGG GAA GAC TTG CAA            389
Glu Leu Leu Glu Arg Asn Gln Arg His Tyr Leu Gly Glu Asp Leu Gln
            105                 110                 115

GCA ATG AGC CCT AAG GAA CTC CAG AAT CTA GAG CAA CAG CTT GAT ACT            437
Ala Met Ser Pro Lys Glu Leu Gln Asn Leu Glu Gln Gln Leu Asp Thr
        120                 125                 130

GCT CTT AAG CAC ATC CGC TCT AGA AAA AAC CAA CTT ATG TAC GAC TCC            485
Ala Leu Lys His Ile Arg Ser Arg Lys Asn Gln Leu Met Tyr Asp Ser
135                 140                 145                 150

ATC AAT GAG CTC CAA AGA AAG GAG AAA GCC ATA CAG GAA CAA AAC AGC            533
Ile Asn Glu Leu Gln Arg Lys Glu Lys Ala Ile Gln Glu Gln Asn Ser
                155                 160                 165

ATG CTT TCC AAG CAG ATT AAG GAG AGG GAA AAC GTT CTT AGG GCG CAA            581
Met Leu Ser Lys Gln Ile Lys Glu Arg Glu Asn Val Leu Arg Ala Gln
            170                 175                 180

CAA GAG CAA TGG GAC GAG CAG AAC CAT GGC CAT AAT ATG CCT CCG CCT            629
Gln Glu Gln Trp Asp Glu Gln Asn His Gly His Asn Met Pro Pro Pro
        185                 190                 195

CCA CCC CCG CAG CAG CAT CAA ATC CAG CAT CCT TAC ATG CTC TCT CAT            677
Pro Pro Pro Gln Gln His Gln Ile Gln His Pro Tyr Met Leu Ser His
200                 205                 210

CAG CCA TCT CCT TTT CTC AAC ATG GGG GGG CTG TAT CAA GAA GAA GAT            725
Gln Pro Ser Pro Phe Leu Asn Met Gly Gly Leu Tyr Gln Glu Glu Asp
215                 220                 225                 230

CAA ATG GCA ATG AGG AGG AAC GAT CTC GAT CTG TCT CTT GAA CCC GGT            773
Gln Met Ala Met Arg Arg Asn Asp Leu Asp Leu Ser Leu Glu Pro Gly
                235                 240                 245

TAT AAC TGC AAT CTC GGC TGC                                                794
Tyr Asn Cys Asn Leu Gly Cys
            250
```

( 2 ) INFORMATION FOR SEQ ID NO:4:

( i ) SEQUENCE CHARACTERISTICS:
    ( A ) LENGTH: 253 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| Met | Gly | Arg | Gly | Arg | Val | Gln | Leu | Lys | Arg | Ile | Glu | Asn | Lys | Ile | Asn |
| 1 | | | | 5 | | | | | 10 | | | | | 15 | |

| Arg | Gln | Val | Thr | Phe | Ser | Lys | Arg | Arg | Ala | Gly | Leu | Met | Lys | Lys | Ala |
| | | | 20 | | | | | 25 | | | | | 30 | | |

| His | Glu | Ile | Ser | Val | Leu | Cys | Asp | Ala | Glu | Val | Ala | Leu | Val | Val | Phe |
| | | | 35 | | | | 40 | | | | | 45 | | | |

| Ser | His | Lys | Gly | Lys | Leu | Phe | Glu | Tyr | Ser | Thr | Asp | Ser | Cys | Met | Glu |
| | 50 | | | | | 55 | | | | | 60 | | | | |

| Lys | Ile | Leu | Glu | Arg | Tyr | Glu | Arg | Tyr | Ser | Tyr | Ala | Glu | Arg | Gln | Leu |
| 65 | | | | | 70 | | | | | 75 | | | | | 80 |

| Ile | Ala | Pro | Glu | Ser | Asp | Ser | Asn | Thr | Asn | Trp | Ser | Met | Glu | Tyr | Asn |
| | | | | 85 | | | | | 90 | | | | | 95 | |

| Arg | Leu | Lys | Ala | Lys | Ile | Glu | Leu | Leu | Glu | Arg | Asn | Gln | Arg | His | Tyr |
| | | | 100 | | | | | 105 | | | | | 110 | | |

| Leu | Gly | Glu | Asp | Leu | Gln | Ala | Met | Ser | Pro | Lys | Glu | Leu | Gln | Asn | Leu |
| | | | 115 | | | | 120 | | | | | 125 | | | |

| Glu | Gln | Gln | Leu | Asp | Thr | Ala | Leu | Lys | His | Ile | Arg | Ser | Arg | Lys | Asn |
| | 130 | | | | | 135 | | | | | 140 | | | | |

| Gln | Leu | Met | Tyr | Asp | Ser | Ile | Asn | Glu | Leu | Gln | Arg | Lys | Glu | Lys | Ala |
| 145 | | | | | 150 | | | | | 155 | | | | | 160 |

| Ile | Gln | Glu | Gln | Asn | Ser | Met | Leu | Ser | Lys | Gln | Ile | Lys | Glu | Arg | Glu |
| | | | | 165 | | | | | 170 | | | | | 175 | |

| Asn | Val | Leu | Arg | Ala | Gln | Gln | Glu | Gln | Trp | Asp | Glu | Gln | Asn | His | Gly |
| | | | | 180 | | | | | 185 | | | | | 190 | |

| His | Asn | Met | Pro | Pro | Pro | Pro | Pro | Gln | Gln | His | Gln | Ile | Gln | His |
| | | | 195 | | | | | 200 | | | | | 205 | | |

| Pro | Tyr | Met | Leu | Ser | His | Gln | Pro | Ser | Pro | Phe | Leu | Asn | Met | Gly | Gly |
| | 210 | | | | | 215 | | | | | 220 | | | | |

| Leu | Tyr | Gln | Glu | Glu | Asp | Gln | Met | Ala | Met | Arg | Arg | Asn | Asp | Leu | Asp |
| 225 | | | | | 230 | | | | | 235 | | | | | 240 |

| Leu | Ser | Leu | Glu | Pro | Gly | Tyr | Asn | Cys | Asn | Leu | Gly | Cys |
| | | | | 245 | | | | | 250 | | | |

( 2 ) INFORMATION FOR SEQ ID NO:5:

( i ) SEQUENCE CHARACTERISTICS:
       ( A ) LENGTH: 768 base pairs
       ( B ) TYPE: nucleic acid
       ( C ) STRANDEDNESS: double
       ( D ) TOPOLOGY: linear ( i i ) MOLECULE TYPE: cDNA ( i x ) FEATURE:
       ( A ) NAME/KEY: CDS
       ( B ) LOCATION: 1..766

( i x ) FEATURE:
       ( A ) NAME/KEY: misc_feature
       ( B ) LOCATION: 1..768
       ( D ) OTHER INFORMATION: /note= "product = Brassica oleracea
           var. botrytis AP1"

( x i ) SEQUENCE DESCRIPTION: SEQ ID NO:5:

-continued

| | | | | | | | | | | | | | | | | |
|---|---|---|---|---|---|---|---|---|---|---|---|---|---|---|---|---|
| ATG | GGA | AGG | GGT | AGG | GTT | CAG | TTG | AAG | AGG | ATA | GAA | AAC | AAG | ATC | AAT | 48 |
| Met | Gly | Arg | Gly | Arg | Val | Gln | Leu | Lys | Arg | Ile | Glu | Asn | Lys | Ile | Asn | |
| 1 | | | | 5 | | | | | 10 | | | | | 15 | | |
| AGA | CAA | GTG | ACA | TTC | TCG | AAA | AGA | AGA | GCT | GGT | CTT | ATG | AAG | AAA | GCT | 96 |
| Arg | Gln | Val | Thr | Phe | Ser | Lys | Arg | Arg | Ala | Gly | Leu | Met | Lys | Lys | Ala | |
| | | | 20 | | | | | 25 | | | | | 30 | | | |
| CAT | GAG | ATC | TCT | GTT | CTG | TGT | GAT | GCT | GAA | GTT | GCG | CTT | GTT | GTC | TTC | 144 |
| His | Glu | Ile | Ser | Val | Leu | Cys | Asp | Ala | Glu | Val | Ala | Leu | Val | Val | Phe | |
| | | | 35 | | | | | 40 | | | | | 45 | | | |
| TCC | CAT | AAG | GGG | AAA | CTC | TTT | GAA | TAC | CCC | ACT | GAT | TCT | TGT | ATG | GAG | 192 |
| Ser | His | Lys | Gly | Lys | Leu | Phe | Glu | Tyr | Pro | Thr | Asp | Ser | Cys | Met | Glu | |
| | 50 | | | | | 55 | | | | | 60 | | | | | |
| GAG | ATA | CTT | GAA | CGC | TAT | GAG | AGA | TAC | TCT | TAC | GCC | GAG | AGA | CAG | CTT | 240 |
| Glu | Ile | Leu | Glu | Arg | Tyr | Glu | Arg | Tyr | Ser | Tyr | Ala | Glu | Arg | Gln | Leu | |
| 65 | | | | | 70 | | | | | 75 | | | | | 80 | |
| ATA | GCA | CCT | GAG | TCC | GAC | TCC | AAT | ACG | AAC | TGG | TCG | ATG | GAG | TAT | AAT | 288 |
| Ile | Ala | Pro | Glu | Ser | Asp | Ser | Asn | Thr | Asn | Trp | Ser | Met | Glu | Tyr | Asn | |
| | | | | 85 | | | | | 90 | | | | | 95 | | |
| AGG | CTT | AAG | GCT | AAG | ATT | GAG | CTT | TTG | GAG | AGA | AAC | CAG | AGG | CAC | TAT | 336 |
| Arg | Leu | Lys | Ala | Lys | Ile | Glu | Leu | Leu | Glu | Arg | Asn | Gln | Arg | His | Tyr | |
| | | | | 100 | | | | | 105 | | | | | 110 | | |
| CTT | GGG | GAA | GAC | TTG | CAA | GCA | ATG | AGC | CCT | AAG | GAA | CTC | CAG | AAT | CTA | 384 |
| Leu | Gly | Glu | Asp | Leu | Gln | Ala | Met | Ser | Pro | Lys | Glu | Leu | Gln | Asn | Leu | |
| | | | 115 | | | | | 120 | | | | | 125 | | | |
| GAG | CAA | CAG | CTT | GAT | ACT | GCT | CTT | AAG | CAC | ATC | CGC | TCT | AGA | AAA | AAC | 432 |
| Glu | Gln | Gln | Leu | Asp | Thr | Ala | Leu | Lys | His | Ile | Arg | Ser | Arg | Lys | Asn | |
| | | 130 | | | | | 135 | | | | | 140 | | | | |
| CAA | CTT | ATG | TAC | GAC | TCC | ATC | AAT | GAG | CTC | CAA | AGA | AAG | GAG | AAA | GCC | 480 |
| Gln | Leu | Met | Tyr | Asp | Ser | Ile | Asn | Glu | Leu | Gln | Arg | Lys | Glu | Lys | Ala | |
| 145 | | | | | 150 | | | | | 155 | | | | | 160 | |
| ATA | CAG | GAA | CAA | AAC | AGC | ATG | CTT | TCC | AAG | CAG | ATT | AAG | GAG | AGG | GAA | 528 |
| Ile | Gln | Glu | Gln | Asn | Ser | Met | Leu | Ser | Lys | Gln | Ile | Lys | Glu | Arg | Glu | |
| | | | | 165 | | | | | 170 | | | | | 175 | | |
| AAC | GTT | CTT | AGG | GCG | CAA | CAA | GAG | CAA | TGG | GAC | GAG | CAG | AAC | CAT | GGC | 576 |
| Asn | Val | Leu | Arg | Ala | Gln | Gln | Glu | Gln | Trp | Asp | Glu | Gln | Asn | His | Gly | |
| | | | 180 | | | | | 185 | | | | | 190 | | | |
| CAT | AAT | ATG | CCT | CCG | CCT | CCA | CCC | CCG | CAG | CAG | CAT | CAA | ATC | CAG | CAT | 624 |
| His | Asn | Met | Pro | Pro | Pro | Pro | Pro | Pro | Gln | Gln | His | Gln | Ile | Gln | His | |
| | | 195 | | | | | 200 | | | | | 205 | | | | |
| CCT | TAC | ATG | CTC | TCT | CAT | CAG | CCA | TCT | CCT | TTT | CTC | AAC | ATG | GGA | GGG | 672 |
| Pro | Tyr | Met | Leu | Ser | His | Gln | Pro | Ser | Pro | Phe | Leu | Asn | Met | Gly | Gly | |
| | 210 | | | | | 215 | | | | | 220 | | | | | |
| CTG | TAT | CAA | GAA | GAA | GAT | CAA | ATG | GCA | ATG | AGG | AGG | AAC | GAT | CTC | GAT | 720 |
| Leu | Tyr | Gln | Glu | Glu | Asp | Gln | Met | Ala | Met | Arg | Arg | Asn | Asp | Leu | Asp | |
| 225 | | | | | 230 | | | | | 235 | | | | | 240 | |
| CTG | TCT | CTT | GAA | CCC | GTT | TAC | AAC | TGC | AAC | CTT | GGC | CGT | CGC | TGC | T | 766 |
| Leu | Ser | Leu | Glu | Pro | Val | Tyr | Asn | Cys | Asn | Leu | Gly | Arg | Arg | Cys | | |
| | | | | 245 | | | | | 250 | | | | | 255 | | |
| GA | | | | | | | | | | | | | | | | 768 |

( 2 ) INFORMATION FOR SEQ ID NO:6:

( i ) SEQUENCE CHARACTERISTICS:
        ( A ) LENGTH: 255 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Gly | Arg | Gly | Arg | Val | Gln | Leu | Lys | Arg | Ile | Glu | Asn | Lys | Ile | Asn |
| 1 | | | | 5 | | | | | 10 | | | | | 15 | |

Arg Gln Val Thr Phe Ser Lys Arg Arg Ala Gly Leu Met Lys Lys Ala
            20                      25                      30

His Glu Ile Ser Val Leu Cys Asp Ala Glu Val Ala Leu Val Val Phe
            35                      40                      45

Ser His Lys Gly Lys Leu Phe Glu Tyr Pro Thr Asp Ser Cys Met Glu
    50                      55                      60

Glu Ile Leu Glu Arg Tyr Glu Arg Tyr Ser Tyr Ala Glu Arg Gln Leu
65                      70                      75                  80

Ile Ala Pro Glu Ser Asp Ser Asn Thr Asn Trp Ser Met Glu Tyr Asn
                85                      90                      95

Arg Leu Lys Ala Lys Ile Glu Leu Leu Glu Arg Asn Gln Arg His Tyr
                100                     105                     110

Leu Gly Glu Asp Leu Gln Ala Met Ser Pro Lys Glu Leu Gln Asn Leu
            115                     120                     125

Glu Gln Gln Leu Asp Thr Ala Leu Lys His Ile Arg Ser Arg Lys Asn
        130                     135                     140

Gln Leu Met Tyr Asp Ser Ile Asn Glu Leu Gln Arg Lys Glu Lys Ala
145                     150                     155                 160

Ile Gln Glu Gln Asn Ser Met Leu Ser Lys Gln Ile Lys Glu Arg Glu
                165                     170                     175

Asn Val Leu Arg Ala Gln Gln Glu Gln Trp Asp Glu Gln Asn His Gly
            180                     185                     190

His Asn Met Pro Pro Pro Pro Pro Gln Gln His Gln Ile Gln His
        195                     200                     205

Pro Tyr Met Leu Ser His Gln Pro Ser Pro Phe Leu Asn Met Gly Gly
    210                     215                     220

Leu Tyr Gln Glu Glu Asp Gln Met Ala Met Arg Arg Asn Asp Leu Asp
225                     230                     235                 240

Leu Ser Leu Glu Pro Val Tyr Asn Cys Asn Leu Gly Arg Arg Cys
                245                     250                     255

( 2 ) INFORMATION FOR SEQ ID NO:7:

( i ) SEQUENCE CHARACTERISTICS:
        ( A ) LENGTH: 1345 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 149..968

( i x ) FEATURE:
        ( A ) NAME/KEY: misc_feature
        ( B ) LOCATION: 1..1345
        ( D ) OTHER INFORMATION: /note= "product = Zea mays AP1"

( x i ) SEQUENCE DESCRIPTION: SEQ ID NO:7:

GCACGAGTCC TCCTCCTCCT CGCATCCCAC CCCACCCCAC CTTCTCCTTA AAGCTACCTG     60

CCTACCCGGC GGTTGCGCGC CGCAATCGAT CGACCGGAAG AGAAAGAGCA GCTAGCTAGC    120

TAGCAGATCG AGCACGGCA ACAAGGCG ATG GGG CGC GGC AAG GTA CAG CTG    172
                                       Met Gly Arg Gly Lys Val Gln Leu
                                        1                    5

AAG CGG ATA GAG AAC AAG ATA AAC CGG CAG GTG ACC TTC TCC AAG CGC    220
Lys Arg Ile Glu Asn Lys Ile Asn Arg Gln Val Thr Phe Ser Lys Arg
  10                  15                    20

```
CGG  AAC  GGC  CTG  CTC  AAG  AAG  GCG  CAC  GAG  ATC  TCC  GTC  CTC  TGC  GAT    268
Arg  Asn  Gly  Leu  Leu  Lys  Lys  Ala  His  Glu  Ile  Ser  Val  Leu  Cys  Asp
25             30                  35                      40

GCC  GAG  GTC  GCC  GTC  ATC  GTC  TTC  TCC  CCC  AAG  GGC  AAG  CTC  TAC  GAG    316
Ala  Glu  Val  Ala  Val  Ile  Val  Phe  Ser  Pro  Lys  Gly  Lys  Leu  Tyr  Glu
                45                  50                      55

TAC  GCC  ACC  GAC  TCC  CGC  ATG  GAC  AAA  ATT  CTT  GAA  CGC  TAT  GAG  CGA    364
Tyr  Ala  Thr  Asp  Ser  Arg  Met  Asp  Lys  Ile  Leu  Glu  Arg  Tyr  Glu  Arg
           60                  65                      70

TAT  TCC  TAT  GCT  GAA  AAG  GCT  CTT  ATT  TCA  GCT  GAA  TCT  GAA  AGT  GAG    412
Tyr  Ser  Tyr  Ala  Glu  Lys  Ala  Leu  Ile  Ser  Ala  Glu  Ser  Glu  Ser  Glu
      75                  80                  85

GGA  AAT  TGG  TGC  CAC  GAA  TAC  AGG  AAA  CTG  AAG  GCC  AAA  ATT  GAG  ACC    460
Gly  Asn  Trp  Cys  His  Glu  Tyr  Arg  Lys  Leu  Lys  Ala  Lys  Ile  Glu  Thr
      90                  95                  100

ATA  CAA  AAA  TGC  CAC  AAG  CAC  CTG  ATG  GGA  GAG  GAT  CTA  GAG  TCT  TTG    508
Ile  Gln  Lys  Cys  His  Lys  His  Leu  Met  Gly  Glu  Asp  Leu  Glu  Ser  Leu
105            110                 115                     120

AAT  CCC  AAA  GAG  CTC  CAG  CAA  CTA  GAG  CAG  CAG  CTG  GAT  AGC  TCA  CTG    556
Asn  Pro  Lys  Glu  Leu  Gln  Gln  Leu  Glu  Gln  Gln  Leu  Asp  Ser  Ser  Leu
                125                 130                     135

AAG  CAC  ATC  AGA  TCA  AGG  AAG  AGC  CAC  CTT  ATG  GCC  GAG  TCT  ATT  TCT    604
Lys  His  Ile  Arg  Ser  Arg  Lys  Ser  His  Leu  Met  Ala  Glu  Ser  Ile  Ser
           140                 145                     150

GAG  CTA  CAG  AAG  AAG  GAG  AGG  TCA  CTG  CAG  GAG  GAG  AAC  AAG  GCT  CTG    652
Glu  Leu  Gln  Lys  Lys  Glu  Arg  Ser  Leu  Gln  Glu  Glu  Asn  Lys  Ala  Leu
      155                 160                     165

CAG  AAG  GAA  CTT  GCG  GAG  AGG  CAG  AAG  GCC  GTC  GCG  AGC  CGG  CAG  CAG    700
Gln  Lys  Glu  Leu  Ala  Glu  Arg  Gln  Lys  Ala  Val  Ala  Ser  Arg  Gln  Gln
      170                 175                     180

CAG  CAA  CAG  CAG  CAG  GTG  CAG  TGG  GAC  CAG  CAG  ACA  CAT  GCC  CAG  GCC    748
Gln  Gln  Gln  Gln  Gln  Val  Gln  Trp  Asp  Gln  Gln  Thr  His  Ala  Gln  Ala
185                 190                 195                     200

CAG  ACA  AGC  TCA  TCA  TCG  TCC  TCC  TTC  ATG  ATG  AGG  CAG  GAT  CAG  CAG    796
Gln  Thr  Ser  Ser  Ser  Ser  Ser  Ser  Phe  Met  Met  Arg  Gln  Asp  Gln  Gln
                205                 210                     215

GGA  CTG  CCG  CCT  CCA  CAC  AAC  ATC  TGC  TTC  CCG  CCG  TTG  ACA  ATG  GGA    844
Gly  Leu  Pro  Pro  Pro  His  Asn  Ile  Cys  Phe  Pro  Pro  Leu  Thr  Met  Gly
                220                 225                     230

GAT  AGA  GGT  GAA  GAG  CTG  GCT  GCG  GCG  GCG  GCG  CAG  CAG  CAG  CAG         892
Asp  Arg  Gly  Glu  Glu  Leu  Ala  Ala  Ala  Ala  Ala  Gln  Gln  Gln  Gln
           235                 240                     245

CCA  CTG  CCG  GGG  CAG  GCG  CAA  CCG  CAG  CTC  CGC  ATC  GCA  GGT  CTG  CCA    940
Pro  Leu  Pro  Gly  Gln  Ala  Gln  Pro  Gln  Leu  Arg  Ile  Ala  Gly  Leu  Pro
      250                 255                     260

CCA  TGG  ATG  CTG  AGC  CAC  CTC  AAT  GCA  T  AAGGAGAGGG  TCGATGAACA           988
Pro  Trp  Met  Leu  Ser  His  Leu  Asn  Ala
265                 270

CATCGACCTC  CTCTCTCTCT  CTCTCTCGTC  ATGGATCATG  ACGTACGCGT  ACCATATGGT           1048

TGCTGTGCCT  GCCCCCATCG  ATCGCGAGCA  ATGGCACGCT  CATGCAAGTG  ATCATTGCTC           1108

CCCGTTGGTT  AAACCCTAGC  CTATGTTCAT  GGCGTCAGCA  ACTAAGCTAA  ACTATTGTTA           1168

TGTTTGCAAG  AAAGGGTAAA  CCCGCTAGCT  GTGTAATCTT  GTCCAGCTAT  CAGTATGCTT           1228

GTTACTGCCC  AGTTACCCTT  GAATCTAGCG  GCGCTTTTGG  TGAGAGGGTG  CAGTTTACTT           1288

TAAACATGGT  TCGTGACTTG  CTGTAAATAG  TAGTATTAAT  CGATTTGGGC  ATCTAAA              1345
```

( 2 ) INFORMATION FOR SEQ ID NO:8:

( i ) SEQUENCE CHARACTERISTICS:

(A) LENGTH: 273 amino acids
(B) TYPE: amino acid
(D) TOPOLOGY: linear (ii) MOLECULE TYPE: protein (xi) SEQUENCE DESCRIPTION: SEQ ID NO:8:

| Met | Gly | Arg | Gly | Lys | Val | Gln | Leu | Lys | Arg | Ile | Glu | Asn | Lys | Ile | Asn |
|---|---|---|---|---|---|---|---|---|---|---|---|---|---|---|---|
| 1 | | | | 5 | | | | | 10 | | | | | 15 | |

| Arg | Gln | Val | Thr | Phe | Ser | Lys | Arg | Arg | Asn | Gly | Leu | Leu | Lys | Lys | Ala |
|---|---|---|---|---|---|---|---|---|---|---|---|---|---|---|---|
| | | | 20 | | | | | 25 | | | | | 30 | | |

| His | Glu | Ile | Ser | Val | Leu | Cys | Asp | Ala | Glu | Val | Ala | Val | Ile | Val | Phe |
|---|---|---|---|---|---|---|---|---|---|---|---|---|---|---|---|
| | | | 35 | | | | | 40 | | | | | 45 | | |

| Ser | Pro | Lys | Gly | Lys | Leu | Tyr | Glu | Tyr | Ala | Thr | Asp | Ser | Arg | Met | Asp |
|---|---|---|---|---|---|---|---|---|---|---|---|---|---|---|---|
| | 50 | | | | | 55 | | | | | 60 | | | | |

| Lys | Ile | Leu | Glu | Arg | Tyr | Glu | Arg | Tyr | Ser | Tyr | Ala | Glu | Lys | Ala | Leu |
|---|---|---|---|---|---|---|---|---|---|---|---|---|---|---|---|
| 65 | | | | | 70 | | | | | 75 | | | | | 80 |

| Ile | Ser | Ala | Glu | Ser | Glu | Ser | Glu | Gly | Asn | Trp | Cys | His | Glu | Tyr | Arg |
|---|---|---|---|---|---|---|---|---|---|---|---|---|---|---|---|
| | | | | 85 | | | | | 90 | | | | | 95 | |

| Lys | Leu | Lys | Ala | Lys | Ile | Glu | Thr | Ile | Gln | Lys | Cys | His | Lys | His | Leu |
|---|---|---|---|---|---|---|---|---|---|---|---|---|---|---|---|
| | | | 100 | | | | | 105 | | | | | 110 | | |

| Met | Gly | Glu | Asp | Leu | Glu | Ser | Leu | Asn | Pro | Lys | Glu | Leu | Gln | Gln | Leu |
|---|---|---|---|---|---|---|---|---|---|---|---|---|---|---|---|
| | | | 115 | | | | | 120 | | | | | 125 | | |

| Glu | Gln | Gln | Leu | Asp | Ser | Ser | Leu | Lys | His | Ile | Arg | Ser | Arg | Lys | Ser |
|---|---|---|---|---|---|---|---|---|---|---|---|---|---|---|---|
| | 130 | | | | | 135 | | | | | 140 | | | | |

| His | Leu | Met | Ala | Glu | Ser | Ile | Ser | Glu | Leu | Gln | Lys | Lys | Glu | Arg | Ser |
|---|---|---|---|---|---|---|---|---|---|---|---|---|---|---|---|
| 145 | | | | | 150 | | | | | 155 | | | | | 160 |

| Leu | Gln | Glu | Glu | Asn | Lys | Ala | Leu | Gln | Lys | Glu | Leu | Ala | Glu | Arg | Gln |
|---|---|---|---|---|---|---|---|---|---|---|---|---|---|---|---|
| | | | | 165 | | | | | 170 | | | | | 175 | |

| Lys | Ala | Val | Ala | Ser | Arg | Gln | Gln | Gln | Gln | Gln | Gln | Gln | Val | Gln | Trp |
|---|---|---|---|---|---|---|---|---|---|---|---|---|---|---|---|
| | | | 180 | | | | | 185 | | | | | 190 | | |

| Asp | Gln | Gln | Thr | His | Ala | Gln | Ala | Gln | Thr | Ser | Ser | Ser | Ser | Ser | Ser |
|---|---|---|---|---|---|---|---|---|---|---|---|---|---|---|---|
| | | 195 | | | | | 200 | | | | | 205 | | | |

| Phe | Met | Met | Arg | Gln | Asp | Gln | Gln | Gly | Leu | Pro | Pro | Pro | His | Asn | Ile |
|---|---|---|---|---|---|---|---|---|---|---|---|---|---|---|---|
| | 210 | | | | | 215 | | | | | 220 | | | | |

| Cys | Phe | Pro | Pro | Leu | Thr | Met | Gly | Asp | Arg | Gly | Glu | Glu | Leu | Ala | Ala |
|---|---|---|---|---|---|---|---|---|---|---|---|---|---|---|---|
| 225 | | | | | 230 | | | | | 235 | | | | | 240 |

| Ala | Ala | Ala | Ala | Gln | Gln | Gln | Pro | Leu | Pro | Gly | Gln | Ala | Gln | Pro |
|---|---|---|---|---|---|---|---|---|---|---|---|---|---|---|
| | | | | 245 | | | | | 250 | | | | | 255 |

| Gln | Leu | Arg | Ile | Ala | Gly | Leu | Pro | Pro | Trp | Met | Leu | Ser | His | Leu | Asn |
|---|---|---|---|---|---|---|---|---|---|---|---|---|---|---|---|
| | | | 260 | | | | | 265 | | | | | 270 | | |

Ala (2) INFORMATION FOR SEQ ID NO:9:

(i) SEQUENCE CHARACTERISTICS:
(A) LENGTH: 779 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 10..775

(ix) FEATURE:
(A) NAME/KEY: unsure
(B) LOCATION: 778..779
(D) OTHER INFORMATION: /note= "N = one or more -continued nucleotides."

( i x ) FEATURE:
    ( A ) NAME/KEY: misc_feature
    ( B ) LOCATION: 1
    ( D ) OTHER INFORMATION: /note= "product = Arabidopsis thaliana CAL"

( x i ) SEQUENCE DESCRIPTION: SEQ ID NO:9:

```
TTAAGAGAA ATG GGA AGG GGT AGG GTT GAA TTG AAG AGG ATA GAG AAC          48
          Met Gly Arg Gly Arg Val Glu Leu Lys Arg Ile Glu Asn
           1               5                  10

AAG ATC AAT AGA CAA GTG ACA TTC TCG AAA AGA AGA ACT GGT CTT TTG         96
Lys Ile Asn Arg Gln Val Thr Phe Ser Lys Arg Arg Thr Gly Leu Leu
         15                  20                  25

AAG AAA GCT CAG GAG ATC TCT GTT CTT TGT GAT GCC GAG GTT TCC CTT        144
Lys Lys Ala Gln Glu Ile Ser Val Leu Cys Asp Ala Glu Val Ser Leu
 30              35                  40                      45

ATT GTC TTC TCC CAT AAG GGC AAA TTG TTC GAG TAC TCC TCT GAA TCT        192
Ile Val Phe Ser His Lys Gly Lys Leu Phe Glu Tyr Ser Ser Glu Ser
                 50                  55                  60

TGC ATG GAG AAG GTA CTA GAA CGC TAC GAG AGG TAT TCT TAC GCC GAG        240
Cys Met Glu Lys Val Leu Glu Arg Tyr Glu Arg Tyr Ser Tyr Ala Glu
             65                  70                  75

AGA CAG CTG ATT GCA CCT GAC TCT CAC GTT AAT GCA CAG ACG AAC TGG        288
Arg Gln Leu Ile Ala Pro Asp Ser His Val Asn Ala Gln Thr Asn Trp
         80                  85                  90

TCA ATG GAG TAT AGC AGG CTT AAG GCC AAG ATT GAG CTT TTG GAG AGA        336
Ser Met Glu Tyr Ser Arg Leu Lys Ala Lys Ile Glu Leu Leu Glu Arg
     95                 100                 105

AAC CAA AGG CAT TAT CTG GGA GAA GAG TTG GAA CCA ATG AGC CTC AAG        384
Asn Gln Arg His Tyr Leu Gly Glu Glu Leu Glu Pro Met Ser Leu Lys
110                 115                 120                 125

GAT CTC CAA AAT CTG GAG CAG CAG CTT GAG ACT GCT CTT AAG CAC ATT        432
Asp Leu Gln Asn Leu Glu Gln Gln Leu Glu Thr Ala Leu Lys His Ile
                130                 135                 140

CGC TCC AGA AAA AAT CAA CTC ATG AAT GAG TCC CTC AAC CAC CTC CAA        480
Arg Ser Arg Lys Asn Gln Leu Met Asn Glu Ser Leu Asn His Leu Gln
            145                 150                 155

AGA AAG GAG AAG GAG ATA CAG GAG GAA AAC AGC ATG CTT ACC AAA CAG        528
Arg Lys Glu Lys Glu Ile Gln Glu Glu Asn Ser Met Leu Thr Lys Gln
        160                 165                 170

ATA AAG GAG AGG GAA AAC ATC CTA AAG ACA AAA CAA ACC CAA TGT GAG        576
Ile Lys Glu Arg Glu Asn Ile Leu Lys Thr Lys Gln Thr Gln Cys Glu
    175                 180                 185

CAG CTG AAC CGC AGC GTC GAC GAT GTA CCA CAG CCA CAA CCA TTT CAA        624
Gln Leu Asn Arg Ser Val Asp Asp Val Pro Gln Pro Gln Pro Phe Gln
190                 195                 200                 205

CAC CCC CAT CTT TAC ATG ATC GCT CAT CAG ACT TCT CCT TTC CTA AAT        672
His Pro His Leu Tyr Met Ile Ala His Gln Thr Ser Pro Phe Leu Asn
                210                 215                 220

ATG GGT GGT TTG TAC CAA GGA GAA GAC CAA ACG GCG ATG AGG AGG AAC        720
Met Gly Gly Leu Tyr Gln Gly Glu Asp Gln Thr Ala Met Arg Arg Asn
            225                 230                 235

AAT CTG GAT CTG ACT CTT GAA CCC ATT TAC AAT TAC CTT GGC TGT TAC        768
Asn Leu Asp Leu Thr Leu Glu Pro Ile Tyr Asn Tyr Leu Gly Cys Tyr
        240                 245                 250

GCC GCT T GANN                                                         779
Ala Ala
255
```

( 2 ) INFORMATION FOR SEQ ID NO:10:

(i) SEQUENCE CHARACTERISTICS:
  (A) LENGTH: 255 amino acids
  (B) TYPE: amino acid
  (D) TOPOLOGY: linear (ii) MOLECULE TYPE: protein (xi) SEQUENCE DESCRIPTION: SEQ ID NO:10:

```
Met Gly Arg Gly Arg Val Glu Leu Lys Arg Ile Glu Asn Lys Ile Asn
 1               5                  10                  15
Arg Gln Val Thr Phe Ser Lys Arg Thr Gly Leu Leu Lys Lys Ala
             20                  25                  30
Gln Glu Ile Ser Val Leu Cys Asp Ala Glu Val Ser Leu Ile Val Phe
             35                  40                  45
Ser His Lys Gly Lys Leu Phe Glu Tyr Ser Ser Glu Ser Cys Met Glu
         50                  55                  60
Lys Val Leu Glu Arg Tyr Glu Arg Tyr Ser Tyr Ala Glu Arg Gln Leu
 65                  70                  75                  80
Ile Ala Pro Asp Ser His Val Asn Ala Gln Thr Asn Trp Ser Met Glu
                 85                  90                  95
Tyr Ser Arg Leu Lys Ala Lys Ile Glu Leu Leu Glu Arg Asn Gln Arg
                100                 105                 110
His Tyr Leu Gly Glu Glu Leu Glu Pro Met Ser Leu Lys Asp Leu Gln
             115                 120                 125
Asn Leu Glu Gln Gln Leu Glu Thr Ala Leu Lys His Ile Arg Ser Arg
130                 135                 140
Lys Asn Gln Leu Met Asn Glu Ser Leu Asn His Leu Gln Arg Lys Glu
145                 150                 155                 160
Lys Glu Ile Gln Glu Glu Asn Ser Met Leu Thr Lys Gln Ile Lys Glu
                 165                 170                 175
Arg Glu Asn Ile Leu Lys Thr Lys Gln Thr Gln Cys Glu Gln Leu Asn
             180                 185                 190
Arg Ser Val Asp Asp Val Pro Gln Pro Gln Pro Phe Gln His Pro His
             195                 200                 205
Leu Tyr Met Ile Ala His Gln Thr Ser Pro Phe Leu Asn Met Gly Gly
    210                 215                 220
Leu Tyr Gln Gly Glu Asp Gln Thr Ala Met Arg Arg Asn Asn Leu Asp
225                 230                 235                 240
Leu Thr Leu Glu Pro Ile Tyr Asn Tyr Leu Gly Cys Tyr Ala Ala
                245                 250                 255
```

(2) INFORMATION FOR SEQ ID NO:11:

(i) SEQUENCE CHARACTERISTICS:
  (A) LENGTH: 756 base pairs
  (B) TYPE: nucleic acid
  (C) STRANDEDNESS: double
  (D) TOPOLOGY: linear (ii) MOLECULE TYPE: cDNA (ix) FEATURE:
  (A) NAME/KEY: CDS
  (B) LOCATION: 1..754

(ix) FEATURE:
  (A) NAME/KEY: misc_feature
  (B) LOCATION: 1..756
  (D) OTHER INFORMATION: /note= "product = Brassica oleracea CAL"

(xi) SEQUENCE DESCRIPTION: SEQ ID NO:11:

```
ATG GGA AGG GGT AGG GTT GAA ATG AAG AGG ATA GAG AAC AAG ATC AAC      48
Met Gly Arg Gly Arg Val Glu Met Lys Arg Ile Glu Asn Lys Ile Asn
 1               5                  10                 15

CGA CAA GTG ACG TTT TCG AAA AGA AGA GCT GGT CTT TTG AAG AAA GCC      96
Arg Gln Val Thr Phe Ser Lys Arg Arg Ala Gly Leu Leu Lys Lys Ala
            20                  25                  30

CAT GAG ATC TCG ATC CTT TGT GAT GCT GAG GTT TCC CTT ATT GTC TTC     144
His Glu Ile Ser Ile Leu Cys Asp Ala Glu Val Ser Leu Ile Val Phe
        35                  40                  45

TCC CAT AAG GGG AAA CTG TTC GAG TAC TCG TCT GAA TCT TGC ATG GAG     192
Ser His Lys Gly Lys Leu Phe Glu Tyr Ser Ser Glu Ser Cys Met Glu
    50                  55                  60

AAG GTA CTA GAA CAC TAC GAG AGG TAC TCT TAC GCC GAG AAA CAG CTA     240
Lys Val Leu Glu His Tyr Glu Arg Tyr Ser Tyr Ala Glu Lys Gln Leu
65                  70                  75                  80

AAA GTT CCA GAC TCT CAC GTC AAT GCA CAA ACG AAC TGG TCA GTG GAA     288
Lys Val Pro Asp Ser His Val Asn Ala Gln Thr Asn Trp Ser Val Glu
                85                  90                  95

TAT AGC AGG CTT AAG GCT AAG ATT GAG CTT TTG GAG AGA AAC CAA AGG     336
Tyr Ser Arg Leu Lys Ala Lys Ile Glu Leu Leu Glu Arg Asn Gln Arg
            100                 105                 110

CAT TAT CTG GGC GAA GAT TTA GAA TCA ATC AGC ATA AAG GAG CTA CAG     384
His Tyr Leu Gly Glu Asp Leu Glu Ser Ile Ser Ile Lys Glu Leu Gln
        115                 120                 125

AAT CTG GAG CAG CAG CTT GAC ACT TCT CTT AAA CAT ATT CGC TCG AGA     432
Asn Leu Glu Gln Gln Leu Asp Thr Ser Leu Lys His Ile Arg Ser Arg
    130                 135                 140

AAA AAT CAA CTA ATG CAC GAG TCC CTC AAC CAC CTC CAA AGA AAG GAG     480
Lys Asn Gln Leu Met His Glu Ser Leu Asn His Leu Gln Arg Lys Glu
145                 150                 155                 160

AAA GAA ATA CTG GAG GAA AAC AGC ATG CTT GCC AAA CAG ATA AGG GAG     528
Lys Glu Ile Leu Glu Glu Asn Ser Met Leu Ala Lys Gln Ile Arg Glu
                165                 170                 175

AGG GAG AGT ATC CTA AGG ACA CAT CAA AAC CAA TCA GAG CAG CAA AAC     576
Arg Glu Ser Ile Leu Arg Thr His Gln Asn Gln Ser Glu Gln Gln Asn
            180                 185                 190

CGC AGC CAC CAT GTA GCT CCT CAG CCG CAA CCG CAG TTA AAT CCT TAC     624
Arg Ser His His Val Ala Pro Gln Pro Gln Pro Gln Leu Asn Pro Tyr
        195                 200                 205

ATG GCA TCA TCT CCT TTC CTA AAT ATG GGT GGC ATG TAC CAA GGA GAA     672
Met Ala Ser Ser Pro Phe Leu Asn Met Gly Gly Met Tyr Gln Gly Glu
    210                 215                 220

TAT CCA ACG GCG GTG AGG AGG AAC CGT CTC GAT CTG ACT CTT GAA CCC     720
Tyr Pro Thr Ala Val Arg Arg Asn Arg Leu Asp Leu Thr Leu Glu Pro
225                 230                 235                 240

ATT TAC AAC TGC AAC CTT GGT TAC TTT GCC GCA T GA                    756
Ile Tyr Asn Cys Asn Leu Gly Tyr Phe Ala Ala
                245                 250
```

( 2 ) INFORMATION FOR SEQ ID NO:12:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Gly Arg Gly Arg Val Glu Met Lys Arg Ile Glu Asn Lys Ile Asn
 1               5                  10                 15
```

-continued

| Arg | Gln | Val | Thr<br>20 | Phe | Ser | Lys | Arg | Arg<br>25 | Ala | Gly | Leu | Leu | Lys<br>30 | Lys | Ala |

| His | Glu | Ile | Ser<br>35 | Ile | Leu | Cys | Asp<br>40 | Ala | Glu | Val | Ser | Leu<br>45 | Ile | Val | Phe |

| Ser | His<br>50 | Lys | Gly | Lys | Leu | Phe<br>55 | Glu | Tyr | Ser | Ser | Ser<br>60 | Cys | Met | Glu |

| Lys<br>65 | Val | Leu | Glu | His | Tyr<br>70 | Glu | Arg | Tyr | Ser | Tyr<br>75 | Ala | Glu | Lys | Gln | Leu<br>80 |

| Lys | Val | Pro | Asp | Ser<br>85 | His | Val | Asn | Ala | Gln<br>90 | Thr | Asn | Trp | Ser | Val<br>95 | Glu |

| Tyr | Ser | Arg | Leu<br>100 | Lys | Ala | Lys | Ile | Glu<br>105 | Leu | Leu | Glu | Arg | Asn<br>110 | Gln | Arg |

| His | Tyr | Leu<br>115 | Gly | Glu | Asp | Leu | Glu<br>120 | Ser | Ile | Ser | Ile | Lys<br>125 | Glu | Leu | Gln |

| Asn | Leu<br>130 | Glu | Gln | Gln | Leu | Asp<br>135 | Thr | Ser | Leu | Lys | His<br>140 | Ile | Arg | Ser | Arg |

| Lys<br>145 | Asn | Gln | Leu | Met | His<br>150 | Glu | Ser | Leu | Asn | His<br>155 | Leu | Gln | Arg | Lys | Glu<br>160 |

| Lys | Glu | Ile | Leu | Glu<br>165 | Glu | Asn | Ser | Met | Leu<br>170 | Ala | Lys | Gln | Ile | Arg<br>175 | Glu |

| Arg | Glu | Ser | Ile<br>180 | Leu | Arg | Thr | His | Gln<br>185 | Asn | Gln | Ser | Glu | Gln<br>190 | Gln | Asn |

| Arg | Ser | His<br>195 | His | Val | Ala | Pro | Gln<br>200 | Pro | Gln | Pro | Gln | Leu<br>205 | Asn | Pro | Tyr |

| Met | Ala<br>210 | Ser | Ser | Pro | Phe | Leu<br>215 | Asn | Met | Gly | Gly | Met<br>220 | Tyr | Gln | Gly | Glu |

| Tyr<br>225 | Pro | Thr | Ala | Val | Arg<br>230 | Arg | Asn | Arg | Leu | Asp<br>235 | Leu | Thr | Leu | Glu | Pro<br>240 |

| Ile | Tyr | Asn | Cys | Asn<br>245 | Leu | Gly | Tyr | Phe | Ala<br>250 | Ala |

( 2 ) INFORMATION FOR SEQ ID NO:13:

( i ) SEQUENCE CHARACTERISTICS:
        ( A ) LENGTH: 756 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..451

( i x ) FEATURE:
        ( A ) NAME/KEY: misc_feature
        ( B ) LOCATION: 1..756
        ( D ) OTHER INFORMATION: /note= "product = Brassica oleracea
            var. botrytis CAL"

( x i ) SEQUENCE DESCRIPTION: SEQ ID NO:13:

| ATG | GGA | AGG | GGT | AGG | GTT | GAA | ATG | AAG | AGG | ATA | GAG | AAC | AAG | ATC | AAC | 48 |
| Met | Gly | Arg | Gly | Arg | Val | Glu | Met | Lys | Arg | Ile | Glu | Asn | Lys | Ile | Asn | |
| 1 | | | | 5 | | | | | 10 | | | | | 15 | | |

| AGA | CAA | GTG | ACG | TTT | TCG | AAA | AGA | AGA | GCT | GGT | CTT | TTG | AAG | AAA | GCC | 96 |
| Arg | Gln | Val | Thr | Phe | Ser | Lys | Arg | Arg | Ala | Gly | Leu | Leu | Lys | Lys | Ala | |
| | | | 20 | | | | | 25 | | | | | 30 | | | |

| CAT | GAG | ATC | TCG | ATT | CTT | TGT | GAT | GCT | GAG | GTT | TCC | CTT | ATT | GTC | TTC | 144 |
| His | Glu | Ile | Ser | Ile | Leu | Cys | Asp | Ala | Glu | Val | Ser | Leu | Ile | Val | Phe | |
| | | | 35 | | | | | 40 | | | | | 45 | | | |

```
TCC  CAT  AAG  GGG  AAA  CTG  TTC  GAG  TAC  TCG  TCT  GAA  TCT  TGC  ATG  GAG      192
Ser  His  Lys  Gly  Lys  Leu  Phe  Glu  Tyr  Ser  Ser  Glu  Ser  Cys  Met  Glu
     50                      55                      60

AAG  GTA  CTA  GAA  CGC  TAC  GAG  AGG  TAC  TCT  TAC  GCC  GAG  AAA  CAG  CTA      240
Lys  Val  Leu  Glu  Arg  Tyr  Glu  Arg  Tyr  Ser  Tyr  Ala  Glu  Lys  Gln  Leu
65                           70                      75                        80

AAA  GCT  CCA  GAC  TCT  CAC  GTC  AAT  GCA  CAA  ACG  AAC  TGG  TCA  ATG  GAA      288
Lys  Ala  Pro  Asp  Ser  His  Val  Asn  Ala  Gln  Thr  Asn  Trp  Ser  Met  Glu
                    85                      90                           95

TAT  AGC  AGG  CTT  AAG  GCT  AAG  ATT  GAG  CTT  TGG  GAG  AGG  AAC  CAA  AGG      336
Tyr  Ser  Arg  Leu  Lys  Ala  Lys  Ile  Glu  Leu  Trp  Glu  Arg  Asn  Gln  Arg
               100                      105                     110

CAT  TAT  CTG  GGA  GAA  GAT  TTA  GAA  TCA  ATC  AGC  ATA  AAG  GAG  CTA  CAG      384
His  Tyr  Leu  Gly  Glu  Asp  Leu  Glu  Ser  Ile  Ser  Ile  Lys  Glu  Leu  Gln
          115                      120                     125

AAT  CTG  GAG  CAG  CAG  CTT  GAC  ACT  TCT  CTT  AAA  CAT  ATT  CGC  TCC  AGA      432
Asn  Leu  Glu  Gln  Gln  Leu  Asp  Thr  Ser  Leu  Lys  His  Ile  Arg  Ser  Arg
     130                      135                     140

AAA  AAT  CAA  CTA  ATG  CAC  T AGTCCCTCAA  CCACCTCCAA  AGAAAGGAGA                  481
Lys  Asn  Gln  Leu  Met  His
145                      150

AAGAAATACT  GGAGGAAAAC  AGCATGCTTG  CCAAACAGAT  AAAGGAGAGG  GAGAGTATCC              541

TAAGGACACA  TCAAAACCAA  TCAGAGCAGC  AAAACCGCAG  CCACCATGTA  GCTCCTCAGC              601

CGCAACCGCA  GTTAAATCCT  TACATGGCAT  CATCTCCTTT  CCTAAATATG  GGTGGCATGT              661

ACCAAGGAGA  ATATCCAACG  GCGGTGAGGA  GGAACCGTCT  CGATCTGACT  CTTGAACCCA              721

TTTACAACTG  CAACCTTGGT  TACTTTGCCG  CATGA                                           756
```

( 2 ) INFORMATION FOR SEQ ID NO:14:

( i ) SEQUENCE CHARACTERISTICS:
        ( A ) LENGTH: 150 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met  Gly  Arg  Gly  Arg  Val  Glu  Met  Lys  Arg  Ile  Glu  Asn  Lys  Ile  Asn
 1                    5                     10                      15

Arg  Gln  Val  Thr  Phe  Ser  Lys  Arg  Arg  Ala  Gly  Leu  Leu  Lys  Lys  Ala
               20                      25                      30

His  Glu  Ile  Ser  Ile  Leu  Cys  Asp  Ala  Glu  Val  Ser  Leu  Ile  Val  Phe
          35                      40                      45

Ser  His  Lys  Gly  Lys  Leu  Phe  Glu  Tyr  Ser  Ser  Glu  Ser  Cys  Met  Glu
     50                      55                      60

Lys  Val  Leu  Glu  Arg  Tyr  Glu  Arg  Tyr  Ser  Tyr  Ala  Glu  Lys  Gln  Leu
65                           70                      75                        80

Lys  Ala  Pro  Asp  Ser  His  Val  Asn  Ala  Gln  Thr  Asn  Trp  Ser  Met  Glu
                    85                      90                           95

Tyr  Ser  Arg  Leu  Lys  Ala  Lys  Ile  Glu  Leu  Trp  Glu  Arg  Asn  Gln  Arg
               100                     105                     110

His  Tyr  Leu  Gly  Glu  Asp  Leu  Glu  Ser  Ile  Ser  Ile  Lys  Glu  Leu  Gln
          115                     120                     125

Asn  Leu  Glu  Gln  Gln  Leu  Asp  Thr  Ser  Leu  Lys  His  Ile  Arg  Ser  Arg
     130                     135                     140

Lys  Asn  Gln  Leu  Met  His
145                     150
```

( 2 ) INFORMATION FOR SEQ ID NO:15:

( i ) SEQUENCE CHARACTERISTICS:
        ( A ) LENGTH: 1500 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 72..1343

( i x ) FEATURE:
        ( A ) NAME/KEY: misc_feature
        ( B ) LOCATION: 1..1500
        ( D ) OTHER INFORMATION: /note= "product = Arabidopsis
                thaliana LEAFY"

( x i ) SEQUENCE DESCRIPTION: SEQ ID NO:15:

```
AAAGCAATCT GCTCAAAAGA GTAAAGAAAG AGAGAAAAAG AGAGTGATAG AGAGAGAGAG                    60

AAAAATAGAT T ATG GAT CCT GAA GGT TTC ACG AGT GGC TTA TTC CGG TGG                   110
            Met Asp Pro Glu Gly Phe Thr Ser Gly Leu Phe Arg Trp
             1               5                  10

AAC CCA ACG AGA GCA TTG GTT CAA GCA CCA CCT CCG GTT CCA CCT CCG                    158
Asn Pro Thr Arg Ala Leu Val Gln Ala Pro Pro Pro Val Pro Pro Pro
         15                  20                  25

CTG CAG CAA CAG CCG GTG ACA CCG CAG ACG GCT GCT TTT GGG ATG CGA                    206
Leu Gln Gln Gln Pro Val Thr Pro Gln Thr Ala Ala Phe Gly Met Arg
 30                  35                  40                  45

CTT GGT GGT TTA GAG GGA CTA TTC GGT CCA TAC GGT ATA CGT TTC TAC                    254
Leu Gly Gly Leu Glu Gly Leu Phe Gly Pro Tyr Gly Ile Arg Phe Tyr
                 50                  55                  60

ACG GCG GCG AAG ATA GCG GAG TTA GGT TTT ACG GCG AGC ACG CTT GTG                    302
Thr Ala Ala Lys Ile Ala Glu Leu Gly Phe Thr Ala Ser Thr Leu Val
             65                  70                  75

GGT ATG AAG GAC GAG GAG CTT GAA GAG ATG ATG AAT AGT CTC TCT CAT                    350
Gly Met Lys Asp Glu Glu Leu Glu Glu Met Met Asn Ser Leu Ser His
         80                  85                  90

ATC TTT CGT TGG GAG CTT CTT GTT GGT GAA CGG TAC GGT ATC AAA GCT                    398
Ile Phe Arg Trp Glu Leu Leu Val Gly Glu Arg Tyr Gly Ile Lys Ala
     95                 100                 105

GCC GTT AGA GCT GAA CGG AGA CGA TTG CAA GAA GAG GAG GAA GAG GAA                    446
Ala Val Arg Ala Glu Arg Arg Arg Leu Gln Glu Glu Glu Glu Glu Glu
110                 115                 120                 125

TCT TCT AGA CGC CGT CAT TTG CTA CTC TCC GCC GCT GGT GAT TCC GGT                    494
Ser Ser Arg Arg Arg His Leu Leu Leu Ser Ala Ala Gly Asp Ser Gly
                130                 135                 140

ACT CAT CAC GCT CTT GAT GCT CTC TCC CAA GAA GAT GAT TGG ACA GGG                    542
Thr His His Ala Leu Asp Ala Leu Ser Gln Glu Asp Asp Trp Thr Gly
            145                 150                 155

TTA TCT GAG GAA CCG GTG CAG CAA CAA GAC CAG ACT GAT GCG GCG GGG                    590
Leu Ser Glu Glu Pro Val Gln Gln Gln Asp Gln Thr Asp Ala Ala Gly
        160                 165                 170

AAT AAC GGC GGA GGA GGA AGT GGT TAC TGG GAC GCA GGT CAA GGA AAG                    638
Asn Asn Gly Gly Gly Gly Ser Gly Tyr Trp Asp Ala Gly Gln Gly Lys
    175                 180                 185

ATG AAG AAG CAA CAG CAG CAG AGA CGG AGA AAG AAA CCA ATG CTG ACG                    686
Met Lys Lys Gln Gln Gln Gln Arg Arg Arg Lys Lys Pro Met Leu Thr
190                 195                 200                 205

TCA GTG GAA ACC GAC GAA GAC GTC AAC GAA GGT GAG GAT GAC GAC GGG                    734
Ser Val Glu Thr Asp Glu Asp Val Asn Glu Gly Glu Asp Asp Asp Gly
                210                 215                 220
```

```
ATG GAT AAC GGC AAC GGA GGT AGT GGT TTG GGG ACA GAG AGA CAG AGG       782
Met Asp Asn Gly Asn Gly Gly Ser Gly Leu Gly Thr Glu Arg Gln Arg
            225                 230                 235

GAG CAT CCG TTT ATC GTA ACG GAG CCT GGG GAA GTG GCA CGT GGC AAA       830
Glu His Pro Phe Ile Val Thr Glu Pro Gly Glu Val Ala Arg Gly Lys
        240                 245                 250

AAG AAC GGC TTA GAT TAT CTG TTC CAC TTG TAC GAA CAA TGC CGT GAG       878
Lys Asn Gly Leu Asp Tyr Leu Phe His Leu Tyr Glu Gln Cys Arg Glu
    255                 260                 265

TTC CTT CTT CAG GTC CAG ACA ATT GCT AAA GAC CGT GGC GAA AAA TGC       926
Phe Leu Leu Gln Val Gln Thr Ile Ala Lys Asp Arg Gly Glu Lys Cys
270                 275                 280                 285

CCC ACC AAG GTG ACG AAC CAA GTA TTC AGG TAC GCG AAG AAA TCA GGA       974
Pro Thr Lys Val Thr Asn Gln Val Phe Arg Tyr Ala Lys Lys Ser Gly
                290                 295                 300

GCG AGT TAC ATA AAC AAG CCT AAA ATG CGA CAC TAC GTT CAC TGT TAC      1022
Ala Ser Tyr Ile Asn Lys Pro Lys Met Arg His Tyr Val His Cys Tyr
            305                 310                 315

GCT CTC CAC TGC CTA GAC GAA GAA GCT TCA AAT GCT CTC AGA AGA GCG      1070
Ala Leu His Cys Leu Asp Glu Glu Ala Ser Asn Ala Leu Arg Arg Ala
        320                 325                 330

TTT AAA GAA CGC GGT GAG AAC GTT GGC TCA TGG CGT CAG GCT TGT TAC      1118
Phe Lys Glu Arg Gly Glu Asn Val Gly Ser Trp Arg Gln Ala Cys Tyr
    335                 340                 345

AAG CCA CTT GTG AAC ATC GCT TGT CGT CAT GGC TGG GAT ATA GAC GCC      1166
Lys Pro Leu Val Asn Ile Ala Cys Arg His Gly Trp Asp Ile Asp Ala
350                 355                 360                 365

GTC TTT AAC GCT CAT CCT CGT CTC TCT ATT TGG TAT GTT CCA ACA AAG      1214
Val Phe Asn Ala His Pro Arg Leu Ser Ile Trp Tyr Val Pro Thr Lys
                370                 375                 380

CTG CGT CAG CTT TGC CAT TTG GAG CGG AAC AAT GCG GTT GCT GCG GCT      1262
Leu Arg Gln Leu Cys His Leu Glu Arg Asn Asn Ala Val Ala Ala Ala
            385                 390                 395

GCG GCT TTA GTT GGC GGT ATT AGC TGT ACC GGA TCG TCG ACG TCT GGA      1310
Ala Ala Leu Val Gly Gly Ile Ser Cys Thr Gly Ser Ser Thr Ser Gly
        400                 405                 410

CGT GGT GGA TGC GGC GGC GAC GAC TTG CGT TTC TAGTTTGGTT TGGGTAGTTG    1363
Arg Gly Gly Cys Gly Gly Asp Asp Leu Arg Phe
    415                 420

TGGTTTGTTT AGTCGTTATC CTAATTAACT ATTAGTCTTT AATTTAGTCT TCTTGGCTAA    1423

TTTATTTTTC TTTTTTGTC AAAACCTTTA ATTTGTTATG GCTAATTTGT TATACACGCA     1483

GTTTTCTTAA TGCGTTA                                                   1500
```

( 2 ) INFORMATION FOR SEQ ID NO:16:

( i ) SEQUENCE CHARACTERISTICS:
        ( A ) LENGTH: 424 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Asp Pro Glu Gly Phe Thr Ser Gly Leu Phe Arg Trp Asn Pro Thr
 1               5                  10                  15

Arg Ala Leu Val Gln Ala Pro Pro Val Pro Pro Leu Gln Gln
            20                  25                  30

Gln Pro Val Thr Pro Gln Thr Ala Ala Phe Gly Met Arg Leu Gly Gly
            35                  40                  45
```

| | | | | | | | | | | | | | | |
|---|---|---|---|---|---|---|---|---|---|---|---|---|---|---|
| Leu | Glu | Gly | Leu | Phe | Gly | Pro | Tyr | Gly | Ile | Arg | Phe | Tyr | Thr | Ala | Ala |
| | | 50 | | | | 55 | | | | 60 | | | | |
| Lys | Ile | Ala | Glu | Leu | Gly | Phe | Thr | Ala | Ser | Thr | Leu | Val | Gly | Met | Lys |
| 65 | | | | | 70 | | | | 75 | | | | | 80 |
| Asp | Glu | Glu | Leu | Glu | Met | Met | Asn | Ser | Leu | Ser | His | Ile | Phe | Arg |
| | | | | 85 | | | | | 90 | | | | | 95 |
| Trp | Glu | Leu | Leu | Val | Gly | Glu | Arg | Tyr | Gly | Ile | Lys | Ala | Ala | Val | Arg |
| | | | 100 | | | | | 105 | | | | 110 | | |
| Ala | Glu | Arg | Arg | Arg | Leu | Gln | Glu | Glu | Glu | Glu | Ser | Ser | Arg |
| | | 115 | | | | | 120 | | | | | 125 | |
| Arg | Arg | His | Leu | Leu | Leu | Ser | Ala | Ala | Gly | Asp | Ser | Gly | Thr | His | His |
| | 130 | | | | | 135 | | | | 140 | | | | |
| Ala | Leu | Asp | Ala | Leu | Ser | Gln | Glu | Asp | Asp | Trp | Thr | Gly | Leu | Ser | Glu |
| 145 | | | | | 150 | | | | | 155 | | | | | 160 |
| Glu | Pro | Val | Gln | Gln | Gln | Asp | Gln | Thr | Asp | Ala | Ala | Gly | Asn | Asn | Gly |
| | | | | 165 | | | | | 170 | | | | | 175 | |
| Gly | Gly | Gly | Ser | Gly | Tyr | Trp | Asp | Ala | Gly | Gln | Gly | Lys | Met | Lys | Lys |
| | | | 180 | | | | | 185 | | | | | 190 | | |
| Gln | Gln | Gln | Gln | Arg | Arg | Arg | Lys | Pro | Met | Leu | Thr | Ser | Val | Glu |
| | | 195 | | | | | 200 | | | | | 205 | | |
| Thr | Asp | Glu | Asp | Val | Asn | Glu | Gly | Glu | Asp | Asp | Asp | Gly | Met | Asp | Asn |
| | | 210 | | | | | 215 | | | | | 220 | | | |
| Gly | Asn | Gly | Gly | Ser | Gly | Leu | Gly | Thr | Glu | Arg | Gln | Arg | Glu | His | Pro |
| 225 | | | | | 230 | | | | | 235 | | | | | 240 |
| Phe | Ile | Val | Thr | Glu | Pro | Gly | Glu | Val | Ala | Arg | Gly | Lys | Lys | Asn | Gly |
| | | | | 245 | | | | | 250 | | | | | 255 | |
| Leu | Asp | Tyr | Leu | Phe | His | Leu | Tyr | Glu | Gln | Cys | Arg | Glu | Phe | Leu | Leu |
| | | | 260 | | | | | 265 | | | | | 270 | | |
| Gln | Val | Gln | Thr | Ile | Ala | Lys | Asp | Arg | Gly | Glu | Lys | Cys | Pro | Thr | Lys |
| | | | 275 | | | | | 280 | | | | | 285 | | |
| Val | Thr | Asn | Gln | Val | Phe | Arg | Tyr | Ala | Lys | Lys | Ser | Gly | Ala | Ser | Tyr |
| | | 290 | | | | | 295 | | | | | 300 | | | |
| Ile | Asn | Lys | Pro | Lys | Met | Arg | His | Tyr | Val | His | Cys | Tyr | Ala | Leu | His |
| 305 | | | | | 310 | | | | | 315 | | | | | 320 |
| Cys | Leu | Asp | Glu | Glu | Ala | Ser | Asn | Ala | Leu | Arg | Arg | Ala | Phe | Lys | Glu |
| | | | | 325 | | | | | 330 | | | | | 335 | |
| Arg | Gly | Glu | Asn | Val | Gly | Ser | Trp | Arg | Gln | Ala | Cys | Tyr | Lys | Pro | Leu |
| | | | 340 | | | | | 345 | | | | | 350 | | |
| Val | Asn | Ile | Ala | Cys | Arg | His | Gly | Trp | Asp | Ile | Asp | Ala | Val | Phe | Asn |
| | | 355 | | | | | 360 | | | | | 365 | | | |
| Ala | His | Pro | Arg | Leu | Ser | Ile | Trp | Tyr | Val | Pro | Thr | Lys | Leu | Arg | Gln |
| | 370 | | | | | 375 | | | | | 380 | | | | |
| Leu | Cys | His | Leu | Glu | Arg | Asn | Asn | Ala | Val | Ala | Ala | Ala | Ala | Ala | Leu |
| 385 | | | | | 390 | | | | | 395 | | | | | 400 |
| Val | Gly | Gly | Ile | Ser | Cys | Thr | Gly | Ser | Ser | Thr | Ser | Gly | Arg | Gly | Gly |
| | | | | 405 | | | | | 410 | | | | | 415 | |
| Cys | Gly | Gly | Asp | Asp | Leu | Arg | Phe |
| | | | 420 | | | | |

( 2 ) INFORMATION FOR SEQ ID NO:17:

( i ) SEQUENCE CHARACTERISTICS:
        ( A ) LENGTH: 4379 base pairs
        ( B ) TYPE: nucleic acid
        ( C ) STRANDEDNESS: double
        ( D ) TOPOLOGY: linear ( i x ) FEATURE:
    ( A ) NAME/KEY: unsure
    ( B ) LOCATION: 2095..2098
    ( D ) OTHER INFORMATION: /note= "N = one or more
          nucleotides."

( i x ) FEATURE:
    ( A ) NAME/KEY: misc_feature
    ( B ) LOCATION: 1..4379
    ( D ) OTHER INFORMATION: /note= "sequence = Arabidopsis
          thaliana AP1 gene"

( x i ) SEQUENCE DESCRIPTION: SEQ ID NO:17:

```
GAATTCCCCG  GATCTCCATA  TACATATCAT  ACATATATAT  AGTATACTAT  CTTTAGACTG      60
ATTTCTCTAT  ACACTATCTT  TTAACTTATG  TATCGTTTCA  AAACTCAGGA  CGTACATGTT     120
TTAAATTTGG  TTATATAACC  ACGACCATTT  CAAGTATATA  TGTCATACCA  TACCAGATTT     180
AATATAACTT  CTATGAAGAA  AATACATAAA  GTTGGATTAA  AATGCAAGTG  ACATCTTTTT     240
AGCATAGGTT  CATTTGGCAT  AGAAGAAATA  TATAACTAAA  AATGAACTTT  AACTTAAATA     300
GATTTTACTA  TATTACAATT  TTTCTTTTA   CATGGTCTAA  TTTATTTTC   TAAAATTAGT     360
ATGATTGTTG  TTTTGATGAA  ACAATAATAC  CGTAAGCAAT  AGTTGCTAAA  AGATGTCCAA     420
ATATTTATAA  ATTACAAAGT  AAATCAAATA  AGGAAGAAGA  CACGTGGAAA  ACACCAAATA     480
AGAGAAGAAA  TGGAAAAAAC  AGAAAGAAAT  TTTTAACAA   GAAAAATCAA  TTAGTCCTCA     540
AACCTGAGAT  ATTTAAAGTA  ATCAACTAAA  ACAGGAACAC  TTGACTAACA  AAGAAATTTG     600
AAATGTGGTC  CAACTTTCAC  TTAATTATAT  TATTTCTCT   AAGGCTTATG  CAATATATGC     660
CTTAAGCAAA  TGCCGAATCT  GTTTTTTTTT  TTTGTTATTG  GATATTGACT  GAAAATAAGG     720
GGTTTTTTCA  CACTTGAAGA  TCTCAAAAGA  GAAAACTATT  ACAACGGAAA  TTCATTGTAA     780
AAGAAGTGAT  TAAGCAAATT  GAGCAAAGGT  TTTTATGTGG  TTTATTTCAT  TATATGATTG     840
ACATCAAATT  GTATATATAT  GGTTGTTTTA  TTAACAATA   TATATGGATA  TAACGTACAA     900
ACTAAATATG  TTTGATTGAC  GAAAAAAAAT  ATATGTATGT  TTGATTAACA  ACATAGCACA     960
TATCAACTGA  TTTTTGTCCT  GATCATCTAC  AACTTAATAA  GAACACACAA  CATTGAAAAA    1020
ATCTTTGACA  AAATACTATT  TTTGGGTTTG  AAATTTTGAA  TACTTACAAT  TATCTTCTCG    1080
ATCTTCCTCT  CTTTCCTTAA  ATCCTGCGTA  CAAATCCGTC  GACGCAATAC  ATTACACAGT    1140
TGTCAATTGG  TTCTCAGCTC  TACCAAAAAC  ATCTATTGCC  AAAAGAAAGG  TCTATTTGTA    1200
CTTCACTGTT  ACAGCTGAGA  ACATTAAATA  TAATAAGCAA  ATTTGATAAA  ACAAAGGGTT    1260
CTCACCTTAT  TCCAAAAGAA  TAGTGTAAAA  TAGGGTAATA  GAGAAATGTT  AATAAAAGGA    1320
AATTAAAAAT  AGATATTTTG  GTTGGGTTCA  GATTTGTTT   CGTAGATCTA  CAGGGAAATC    1380
TCCGCCGTCA  ATGCAAAGCG  AAGGTGACAC  TTGGGGAAGG  ACCAGTGGTC  GTACAATGTT    1440
ACTTACCCAT  TTCTCTTCAC  GAGACGTCGA  TAATCAAATT  GTTTATTTC   ATATTTTAA     1500
GTCCGCAGTT  TTATTAAAAA  ATCATGGACC  CGACATTAGT  ACGAGATATA  CCAATGAGAA    1560
GTCGACACGC  AAATCCTAAA  GAAACCACTG  TGGTTTTTGC  AAACAAGAGA  AACCAGCTTT    1620
AGCTTTTCCC  TAAAACCACT  CTTACCCAAA  TCTCTCCATA  AATAAAGATC  CCGAGACTCA    1680
AACACAAGTC  TTTTTATAAA  GGAAAGAAAG  AAAAACTTTC  CTAATTGGTT  CATACCAAAG    1740
TCTGAGCTCT  TCTTTATATC  TCTCTTGTAG  TTTCTTATTG  GGGTCTTTG   TTTTGTTTGG    1800
TTCTTTTAGA  GTAAGAAGTT  TCTTAAAAAA  GGATCAAAAA  TGGGAAGGGG  TAGGGTTCAA    1860
TTGAAGAGGA  TAGAGAACAA  GATCAATAGA  CAAGTGACAT  TCTCGAAAAG  AAGAGCTGGT    1920
CTTTTGAAGA  AAGCTCATGA  GATCTCTGTT  CTCTGTGATG  CTGAAGTTGC  TCTTGTTGTC    1980
```

```
TTCTCCCATA  AGGGGAAACT  CTTCGAATAC  TCCACTGATT  CTTGGTAACT  TCAACTAATT  2040
CTTTACTTTT  AAAAAAATCT  TTTAATCTGC  TACTTTATAT  AGTTTTTTTC  CCCCNNNNGG  2100
TCTATGATTC  ATACTGTTTT  GTTATTATAA  AGGTATCATA  GAGATCGGTA  CTTGATTTGT  2160
TATAGGAAAT  CTTGGTTTAA  TTGCATAAAA  CCATCATTAG  ATTTATCCTA  AAATGTGATG  2220
ATATTTTGGT  CACATCTCCA  TATTATTTAT  ATAATAAAAT  GATAATTGGT  TGATGATAAA  2280
GCTAACCCTA  ATTCTGTGAA  ATGATCAGTA  TGGAGAAGAT  ACTTGAACGC  TATGAGAGGT  2340
ACTCTTACGC  CGAAAGACAG  CTTATTGCAC  CTGAGTCCGA  CGTCAATGTA  TTTCAATAAA  2400
TATTTCTCCT  TTTAATCCAC  ATATATATTA  TATCAATCTA  TTTGTAGTAT  TGATGAATTT  2460
TATTTGTATA  AAACTTCTGG  TACACAGACA  AACTGGTCGA  TGGCGTATAA  CAGGCTTAAG  2520
GCTAAGATTG  AGCTTTTGGA  GAGAAACCAG  AGGTACACAT  TTACACTCAT  CACATTTCTA  2580
TCTAGAAAAT  CGATCGGGTT  CCATTTTAAA  GTAAGTTAAA  ATTCATTGAT  GCTATTGAAA  2640
TTCAGGCATT  ATCTTGGGGA  AGACTTGCAA  GCAATGAGCC  CTAAAGAGCT  TCAGAATCTG  2700
GAGCAGCAGC  TTGACACTGC  TCTTAAGCAC  ATCCGCACTA  GAAAAGTATT  GCCTTCTGCT  2760
ATTTCGTTGA  ACATATCTAT  ATAACTTAAA  CGTTTACAAG  TGTTATTATA  ATGTGAACAT  2820
TGAAATACAT  ATGTGTATGT  ATCAATATAT  ATATCAGTAA  TCAATATCAA  TTTGATATGT  2880
CTATAGGTTG  GTTCGAATGT  ATGAGTTATG  TTGTGTATTT  TAAGACTCCA  TATTACTTAA  2940
AGTAATGGGT  TGTTAATGTT  GATGTGTGTG  TATGCAGAAC  CAACTTATGT  ACGAGTCCAT  3000
CAATGAGCTC  CAAAAAAAGG  TATGTAAAAC  CCCTATCAAA  TGTATGTCTT  ATAGAGAAAC  3060
GTATAGGAAA  GCTAATTAAC  AATCGTGCCG  TTTCGGAATG  ACAGGAGAAG  GCCATACAGG  3120
AGCAAAACAG  CATGCTTTCT  AAACAGGAAC  ACATGTCATC  ATTTCTCTTT  CATCAACATG  3180
TTGTCCATTG  CATTACTGTT  ACCTTCCACT  GTTCTGCTCC  ACACTTCCAG  CCAAGCTATA  3240
CCTACGATAT  CTTCATATCT  CCACTTAACT  TCGGCACCAT  TAAATAAAAA  TAGAAAATCT  3300
TTGCAAATTT  GTTTGAAATA  GCATAGATGT  TGTCTATTGA  TTGATATAAT  CACCAGCCTG  3360
TACGTAGATA  TGGTTTGTCC  GTTTAGTTTT  AAGGTGTCTC  TCGGATTGAA  AATATTTTGA  3420
AATCTTTTGA  AATGTTTGTC  CCATCATTCT  TACTTAGCTC  ATATCTATGT  ATATGAATAT  3480
AGACACTACT  CCTAATTATA  AAATGTTATA  ATAGTTCATT  GCATGAGTGC  AACTGTGAAA  3540
ATAACTATTT  GTAACCATTG  CATATATATA  GTTCTTCAC   TTTGAAAATT  GATGATGATA  3600
ATATGGTTTG  AAATAAATTT  GCTGGCAGAT  CAAGGAGAGG  GAAAAAATTC  TTAGGGCTCA  3660
ACAGGAGCAG  TGGGATCAGC  AGAACCAAGG  CCACAATATG  CCTCCCCCTC  TGCCACCGCA  3720
GCAGCACCAA  ATCCAGCATC  CTTACATGCT  CTCTCATCAG  CCATCTCCTT  TTCTCAACAT  3780
GGGGTAACAA  AAAATTACTA  ATCAGTCTTA  ATTTAAAGCA  CATATGTTAT  GCAAGCTAGT  3840
TACGTTAGGT  GTTGTAATTT  CATTGAAGTT  ATAGCTGTTA  GTGATGGTTA  CATGATGCTA  3900
GATTTTGAAA  CTAGAAAACT  TTATTTTAAA  ACATTATTTT  ATTAACGTAG  GTTAATGCAA  3960
TGGTCGCCAA  ACGAACAAAC  TTATTAGTGT  GGAAAAATGT  ACATGGAATG  GTTGCGAAAA  4020
GCCTAAGTCG  ACTTTTGTTG  TTGTTGGTCT  ATGTGTTTAA  GTACAATTTT  AGTTTGTTAG  4080
ATAAATGAAA  TTAATATATC  TTTGACATTT  CACAATGGAC  TGATATTTGA  TTTTCCTTTG  4140
TTGTACGGTG  AAACATATGA  TTACATATGC  ACTTTCATAT  ATATCCTATG  TATGATTGTG  4200
AATGCAGTGG  TCTGTATCAA  GAAGATGATC  CAATGGCAAT  GAGGAGGAAT  GATCTCGAAC  4260
TGACTCTTGA  ACCCGTTTAC  AACTGCAACC  TTGGCCGTTC  GCCGCATGAA  GCATTTCCAT  4320
ATATATATAT  TTGTAATCGT  CAACAATAAA  AACTAGTTTG  CCATCATACA  TATAAATAG   4379
```

( 2 ) INFORMATION FOR SEQ ID NO:18:

( i ) SEQUENCE CHARACTERISTICS:
        ( A ) LENGTH: 1865 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: unsure
        ( B ) LOCATION: 1077..1081
        ( D ) OTHER INFORMATION: /note= "N = one or more
            nucleotides."

( i x ) FEATURE:
        ( A ) NAME/KEY: misc_feature
        ( B ) LOCATION: 1..1865
        ( D ) OTHER INFORMATION: /note= "sequence = Brassica
            oleracea AP1 gene"

( x i ) SEQUENCE DESCRIPTION: SEQ ID NO:18:

```
GCACCTGAGT  CCGACTCCAA  TGTAAACCAA  TTTCTCTCCA  TTAACTTATA  TAAATTAAAT      60

ATTATTTCAG  TATTAGTGAT  ATATACTTAT  CTGTATTAAA  CTTGTGAGAT  ATAGACGAAC     120

TGGTCGATGG  AGTATAATAG  GCTTAAGGCT  AAGATTGAGC  TTTTGGAGAG  AAACCAGAGG     180

TACATTTTCA  TTCATCATTT  ATATTAATAG  ATGAAATATC  AAACAGGATT  AATGTTAGTT     240

AAAAATGCAT  GATTACTTAT  AAGAAAATGA  TGCATTTAAA  TAACAAAAAA  ATGCATCGAT     300

GCTCTATTGA  AATTTAGGCA  CTATCTTGGG  GAAGACTTGC  AAGCAATGAG  CCCTAAGGAA     360

CTCCAGAATC  TAGAGCAACA  GCTTGATACT  GCTCTTAAGC  ACATCCGCTC  TAGAAAAGTA     420

TGAATCCTCC  TATTTCTTTA  ATTAACATGT  ATACAACTTA  AACACATATT  ATTTTATTAT     480

TCAATACATA  TATATGAATA  GTACATATGT  GATTTTATTG  GTTGGATATA  AAAGATCAAT     540

CACGTCGATT  AGATGTATGA  CTTTTTAAAG  AATTAGTATA  TAGAGTATGA  TTAGTCAATG     600

TAATGGTACG  TACGTTTATG  CAGAACCAAC  TTATGTACGA  CTCCATCAAT  GAGCTCCAAA     660

GAAAGGTATG  TATAAACCCT  ATCAAATTGA  CGTTTACATA  GAATAACTGC  GTGTAAGAAT     720

CCTATAGGGG  AGCTAACAAT  CGTGCCGTTT  TGGAAATGAC  AGGAGAAAGC  CATACAGGAA     780

CAAAACAGCA  TGCTTTCCAA  GCAGGTGCCA  TTTGTCATTA  TTTTTATATC  GTCAAAATGT     840

TTTCTATTGT  AGTACTGTTA  GCTTCCACTG  TTCTACTCCA  CACTTCAAGC  CAAGCTATAC     900

CTACCTACGA  CTACGAGATT  CTCCACATAT  TTCTCCACTT  AGCTTCGGCA  CCACTATAAC     960

TAAAATATAG  ATAAAATATC  ATTTTATAG   TCTATGATTG  ATATACTCGT  CAGCCAGTAC    1020

GTAGTTGGGT  ATTTGCCCGT  TTAGTTTTAA  GGTTCTTTTC  CGGATTGAAA  ATATTTNNNN    1080

NACCCTACCT  TTGATGCTAT  TATATGTATA  TCTATTTAGA  AGTCGTGGCT  TTGAAAATTG    1140

ATGATGATAT  GTATGGTATA  AGTTGGTAAC  AAACTGGTGT  GTGAAATTGA  AACTTGTCAG    1200

ATTAAGGAGA  GGGAAAACGT  TCTTAGGGCG  CAACAAGAGC  AATGGGACGA  GCAGAACCAT    1260

GGCCATATAT  GCCTCCGCCT  CCACCCCGC   AGCAGCATCA  AATCCAGCAT  CCTTACATGC    1320

TCTCTCATCA  GCCATCTCCT  TTTCTCAACA  TGGGGTAGTT  AAAAATTCGT  TCCTCTTACT    1380

TTCAAGTCAT  ATGTGTATAT  ATACAAGATA  GTTAGGTGTT  ATAAGTCCAG  TGAGTTAGGT    1440

TGTGTTAGTG  ATGGTTAGAT  GTCTAGATTG  TGAATTACAA  GTACTAAGAT  TTTTCAGTTA    1500

TATAATTAAC  GTATTGATCA  TCAATCAAAT  GGTCGTAAAA  AAACAGACTT  ATATTTTGG    1560

GAAAGTAGAT  GGAATGGCTG  CTAAAAGTCT  AAGAAACCTT  TGGGAGCAGG  TCGTATTTAT    1620
```

```
TGTTGTTCAA   ATTAAACTTG   AGGTAGTTAG   ATAAATAAAC   TATCTTTGAT   ATGGCCTTTA      1680

CCAATTTCAC   TACAAAACAT   GTGATATTTT   CAGCACCTAT   GTAGATAATT   TGTAAGCTAT      1740

ATCATGTGCA   TATGAATGTA   AATGCAGGGG   GCTGTATCAA   GAAGAAGATC   AAATGGCAAT      1800

GAGGAGGAAC   GATCTCGATC   TGTCTCTTGA   ACCCGGTTAC   AACTGCAACC   TTGGCCGTCG      1860

CCGCT                                                                          1865
```

( 2 ) INFORMATION FOR SEQ ID NO:19:

( i ) SEQUENCE CHARACTERISTICS:
        ( A ) LENGTH: 2185 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: unsure
        ( B ) LOCATION: 295..297
        ( D ) OTHER INFORMATION: /note= "N = one or more
            nucleotides."

( i x ) FEATURE:
        ( A ) NAME/KEY: unsure
        ( B ) LOCATION: 1389..1391
        ( D ) OTHER INFORMATION: /note= "N = one or more
            nucleotides."

( i x ) FEATURE:
        ( A ) NAME/KEY: misc_feature
        ( B ) LOCATION: 1..2185
        ( D ) OTHER INFORMATION: /note= "sequence = Brassica
            oleracea var. botrytis AP1 gene"

( x i ) SEQUENCE DESCRIPTION: SEQ ID NO:19:

```
GAGCTCTTCT   TTATATCTCT   TCTTGTAGTT   TCTTGTTTCG   TTTGGTTCTC   TTAGAGGAAA        60

TAGTTCCTTT   AAAAGGGATA   AAAATGGGAA   GGGGTAGGGT   TCAGTTGAAG   AGGATAGAAA       120

ACAAGATCAA   TAGACAAGTG   ACATTCTCGA   AAAGAAGAGC   TGGTCTTATG   AAGAAAGCTC       180

ATGAGATCTC   TGTTCTGTGT   GATGCTGAAG   TTGCGCTTGT   TGTCTTCTCC   CATAAGGGGA       240

AACTCTTTGA   ATACCCCACT   GATTCTTGGT   AACTTTCTCA   TTTAAGAAAC   AAAANNNTAC       300

CCTAAGATTG   TATTTTACAT   GATCATTTAC   TTGTTTTACA   CAGTATATAC   TCTATGTATA       360

TAATATGATC   ATAAATTGTT   GATGATAAGA   AGCTAGCCCT   AATTCTGTGA   ATTGAACAGT       420

ATGGAGGAGA   TACTTGAACG   CTATGAGAGA   TACTCTTACG   CCGAGAGACA   GCTTATAGCA       480

CCTGAGTCCG   ACTCCAATGT   AAACCAATTT   CTCTCCATTA   ACTTATATAA   ATTAAATATT       540

ATTTCAGTAT   TAGTGATATA   TACTTATCTG   TATTAAACTT   GTGAGATATA   GACGAACTGG       600

TCGATGGAGT   ATAATAGGCT   TAAGGCTAAG   ATTGAGCTTT   TGGAGAGAAA   CCAGAGGTAC       660

ATTTTCATTC   ATCATTTATA   TATATGATGA   AATATCAAAC   AGGATTAATG   TTAGTTAAAA       720

ATGCATGATT   ACTTATAAAA   AAATGATGCA   TTTAAATAAC   AAAAAAATGC   ATCGATGCTC       780

TATTGAAATT   TAGGCACTAT   CTTGGGGAAG   ACTTGCAAGC   AATGAGCCCT   AAGGAACTCC       840

AGAATCTAGA   GCAACAGCTT   GATACTGCTC   TTAAGCACAT   CCGCTCTAGA   AAAGTATGAA       900

TCCTCCTATT   TCTTTAATTA   ACATGTATAC   AACTTAAACA   CATATTATTT   TATTATTCAA       960

ATACATATAT   ATAAATAGTA   CATATGTGAT   TTTATTGGTT   GGATTTGAAA   AGATCAATCA      1020

CGTCGATTAG   AATGTATGAC   TTTTTAAAGA   ATTAGTATAT   AGAGTATGAT   TAGTCAATGT      1080

AATGGATCGT   TTATGCAGAA   CCAACTTATG   TACGACTCCA   TCAATGAGCT   CCAAAGAAAG      1140

GTATGTATAA   ACCCTATCAA   ATTGACGTTT   ACATAGAATA   ACTGCGTGTA   AGAATCCTAT      1200
```

| | | | | | | |
|---|---|---|---|---|---|---|
| AGGGGAGCTA | AAAATCGTGC | CGTTTTGGAA | ATGACAGGAG | AAAGCCATAC | AGGAACAAAA | 1260 |
| CAGCATGCTT | TCCAAGCAGG | TGCCATTTGT | CATTATTTTT | ATTTCGTCAA | AATGTTTTCT | 1320 |
| ATTGTAGATC | TGTTAGCTTC | CACTGTTCTC | ACCACACTTC | AAGCCAAGCT | ATACCTACCT | 1380 |
| ACGACTACNN | NCCTACATTT | GATGCTATTT | ATATGTATAT | CTATTTAGAA | GTCGTGGCTT | 1440 |
| TGAAAATTGA | TGATGATATG | GTATGGTATA | AGTTGGTAAC | AAACTGGTGT | GTGAAATTGA | 1500 |
| AACTTGTCAG | ATTAAGGAGA | GGGAAAACGT | TCTTAGGGCG | CAACAAGAGC | AATGGGACGA | 1560 |
| GCAGAACCAT | GGCCATAATA | TGCCTCCGCC | TCCACCCCCG | CAGCAGCATC | AAATCCAGCA | 1620 |
| TCCTTACATG | CTCTCTCATC | AGCCATCTCC | TTTTCTCAAC | ATGGGGTAGT | TAAAAATTCG | 1680 |
| TTCCTCTTAC | TTTCAAGTAC | ATATGTGTTA | TATATACAAG | ATAGTTAGGT | GTTATAAGTC | 1740 |
| CAGTGAGTTA | AGTTGTGTTA | GTGATGGTTA | GATGTCTAAA | TTGTGAAATA | CAAGTACTAA | 1800 |
| GATTTTTCAT | GTATATATTT | AAACGTATTA | ATCATCAATC | AAATGGTCGT | AAAAGAAACA | 1860 |
| GACTTATATT | TTTGGGAAAA | GTAGATGGAA | TGGCTGCTAA | AAGTCTAAGA | AACCTTTGGG | 1920 |
| AGCAGGTCGT | TTTTATTGTT | GTTCAAATTA | AACTTGAGGT | AGTTAGATAA | ATAAACTATC | 1980 |
| TTTGATATGG | GCCTTTACCA | ATTTCACTAC | AAAACATGTG | ATATTTCAG | CACCTATGTA | 2040 |
| GATAATTTTG | TAAGCTATAT | CATGTGCATA | TGAATGTAAA | TGTAGAGGGC | TGTATCAAGA | 2100 |
| AGAAGATCAA | ATGGCAATGA | GGAGGAACGA | TCTCGATCTG | TCTCTTGAAC | CCGTTTACAA | 2160 |
| CTGCAACCTT | GGCCGTCGCT | GCTGA | | | | 2185 |

(2) INFORMATION FOR SEQ ID NO:20:

(i) SEQUENCE CHARACTERISTICS:
        (A) LENGTH: 5855 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..5855
        (D) OTHER INFORMATION: /note= "sequence = Arabidopsis
            thaliana CAL gene"

(xi) SEQUENCE DESCRIPTION: SEQ ID NO:20:

| | | | | | | |
|---|---|---|---|---|---|---|
| GGATCCCTCC | GGAAGCCTTA | GATCAATGGT | AGTTGTGGTT | ATTTAAGAT | CAGATTCTTT | 60 |
| TGGAAATCCA | GTAACATAGT | CTGGGAATAT | GATTTGCTTG | TTGGTCACCG | TTACTGCTTC | 120 |
| TGCGTTCGTC | ATTTCCGATT | TTACGTACTT | TTGATCACTA | TGATAATTTC | TTCTTTCTTA | 180 |
| CGTCGAGATG | TGTCTGCTTT | TTGTAGATTG | AATTTCTCAA | TGTTGCTTTG | ATCATAAGAC | 240 |
| CATTTGATTT | CTTTCCTTCA | TTGATCGATC | CAATTTCTTC | GGGAGATAAA | TAAGGTAAAA | 300 |
| ATGGACTATT | ATTTTGGAA | AATACAGGAG | AAAAAAATTC | TTAAGAATAA | AAGAGTATTT | 360 |
| ATAGTGACCA | TGAATTTTGT | TGTTTTTTTA | AAAAGAAAAA | AAAACTCGAT | TGGATTGGAT | 420 |
| GACACATTGA | AATTAACATT | CAAATAGCAT | CTTAGTTAAC | AGATATTGCA | TGCACCATAT | 480 |
| AATAAAATAT | CATAATTATG | TGTGATGCGA | GGTTTGTTTT | GGTCAAAATG | TTATTTTAAT | 540 |
| CACAATTTAA | TAACAGATCA | TTTACCAATT | TGTTTTTTGA | TAATTTATGC | CAACTTAGTA | 600 |
| AATTCATCCA | AAAAGTTGAA | AAATATAGAT | GTGTAATATG | TTGACGGATA | TACAACACTC | 660 |
| AAAACAATAT | ACTCAAAAAA | AAAAAAAATT | GAAAGCGGCA | ACGATTCAAA | CATATATGCT | 720 |
| AAATTTTAAT | AATGGACAAA | GGAGGAAGTA | CTGCATATGT | ACGAAAAGTG | TTGATAATGG | 780 |

-continued

| | | | | | | |
|---|---|---|---|---|---|---|
| AGAGCAGCGG | ATAGTGTCGC | CAAGGGCACG | AGCTTTAGAT | TCTTTTAGTT | TGCTCTAAAT | 840 |
| GTTCTTCTTT | GGTACTTTTA | ATTGCTTTAG | TTGCTTGCTT | CTTATCTCCA | CATAAATAAA | 900 |
| TGGGGTAACC | ATTTTCTCTC | GTATCTTATT | CCGATCTTTG | GATCTATGTA | CGTACTACAT | 960 |
| GAATAAATCG | TGTTCAATAA | GTTATTATCA | TTTGGTCTGC | TTAAAGTGAT | CATGGTGTAT | 1020 |
| TAATCTATAA | TACGTAGTTC | TCTTAATTTA | TTCCCTAGAA | TTCCATCAAA | GACAAATTTT | 1080 |
| AGCAAAAAGA | AAAGTTGAGT | ATATAATTTG | CTTAGTAGTA | CAAAAAAAA | CTTTATGGTA | 1140 |
| ATTTGTATTT | TGGATATTTC | CTTNATTAAC | CCAAACTTCA | AAATTAATTT | TCTTCTGCTG | 1200 |
| TATCTTTATA | TCCAACGTGA | AATCTATTGA | CTCAACAAAA | TACACAGTTG | TCAATTGAAG | 1260 |
| TTCAACTCTA | CCAAGAAACA | TCTATATGTA | CTTCACTGTT | CTTACCGCCG | AGCAATTAAA | 1320 |
| ACCTCTATAA | CTACTTGGTT | ACATTATTAC | ATTTTTATTT | ACAAAAATA | TATATCAACA | 1380 |
| ACCAATAATA | TAGTTAGAAA | ATGAAAGAAA | ATTATTTAAG | AAATATCCGC | CGTCAATGCA | 1440 |
| AATCGAATGC | GACACTTGGG | GAAGCTCTGA | AGTCTGTGGT | CTGTGCATAT | TTCACTTGTC | 1500 |
| TAGCTAACCC | ATTTTCACGT | CACTAGACGT | CGATAATCAA | TTATTGTTAT | TTTTTTATC | 1560 |
| AATGTTCCAC | TTATTGAAAA | TTATATACGA | GAAAACATAG | ACTCGACATT | AGGCAATGGA | 1620 |
| AGTCTAATCA | GACCAATGAG | AAGTCGACAA | CACATCCTAG | AAACCAACTC | TGGTTTATTT | 1680 |
| CCTTCCCTAA | TACCAAGTTA | TAGNNTTCTT | TCAAACCGCT | ATTTCCAAAA | TATCTCTTCT | 1740 |
| TTAAATAAAG | AGTGAAAGAA | GCACTCTTTC | ACATTACCAT | CATTAGAAAA | CTTTCCTAAT | 1800 |
| TAGATCAAGA | TCGTCGTTAT | CTCTCTTGTT | TTTTCTTCAT | ATAATTTAGT | TATTTTAAGA | 1860 |
| GAAATGGGAA | GGGGTAGGGT | TGAATTGAAG | AGGATAGAGA | ACAAGATCAA | TAGACAAGTG | 1920 |
| ACATTCTCGA | AAAGAAGAAC | TGGTCTTTTG | AAGAAAGCTC | AGGAGATCTC | TGTTCTTTGT | 1980 |
| GATGCCGAGG | TTTCCCTTAT | TGTCTTCTCC | CATAAGGGCA | AATTGTTCGA | GTACTCCTCT | 2040 |
| GAATCTTGGT | AATTGCTTAA | TTCCTTCTTT | TTTTAATGTT | ATTTTAGTG | TGCCTTCGTT | 2100 |
| TGCCCTAACT | AGTAGTCTTT | GTTCTACTTA | AGGCATATTT | TCTGTGTCTT | CTATGCTATT | 2160 |
| ATCTGTCTTT | GCTGAAAATT | TGCCACTGAT | TTGGTATCTA | TTTACTTGGG | ATCTACGAAC | 2220 |
| TGATTGTGTT | GGTCATATCA | TTAGTTTATT | TTTATCAATA | ATTTATTATA | TATCAAAGAA | 2280 |
| AATGAAATTT | TTTAGGACTT | TTAGTGAACC | CTACAATACG | ATCTACTTAA | TTATAGTGGC | 2340 |
| ATGGATTTGT | AAGAAATCTT | CAGCATCTTC | TTTAATCTGG | AAATGTACAT | TTTGCTTCAA | 2400 |
| GTCAAGTTTA | GTATATTAGG | TACAGAAAGA | ACGGATGTTT | ATGGTCTAGA | CTAGGGTTTT | 2460 |
| TGCTTTTAGG | AAAGCTATAC | TTTTGCTTAA | ATATCTTTAA | GTTGCATTTT | ATGAACACAC | 2520 |
| ACACACATAT | ATATATATAT | ATATTAGTAT | ACCAATAATC | TTAATTAAGT | TTAGAAAGAA | 2580 |
| ACTCTTCATT | TTTTCCCATT | TAATAATGGT | TTATAGCTAG | GTATAGAGAA | ACTGGAAATA | 2640 |
| AGTATGTGAC | ATCTAAGTAT | GGGGAGTCTT | TGACCTCTGG | GGATTAATGT | AAAACAGATC | 2700 |
| GTTCTTTTTT | TTCTAAACAG | TTCCTCCGTA | CTGATGGTCA | AACTTAACTT | CAACAGTTCC | 2760 |
| TTTTAAACTT | TTATAGGGTG | CTTGAATACG | TCTTGGGGTG | TGGGGTTAGT | GGCTCAACTG | 2820 |
| GTTTATTTAT | TTTTAAAAAT | GGTAGAAATC | AGTACTGTTT | CTAGCTAGGG | TTTAGGCACA | 2880 |
| AAACTAGAGA | TCATCTTTAT | TCCATAATAG | AAAGGAAGAA | ACTAATGTTT | AATGACATAG | 2940 |
| ATTAATTAGA | TAACCCTACA | TAATCAGATG | CTATATGTTA | TCACATATTT | TGGGTGAATC | 3000 |
| GTTAATTACG | TTTGAAACAA | GTGGCCTCTT | GTGCTAGCTG | ATAAGATAGT | TGNGTATGCA | 3060 |
| ATTATATTGG | TGGTTGAATC | CAAACTAATT | CTAACTCGTA | AGCTTAATAT | TTGTAGCATG | 3120 |
| GAGAAGGTAC | TAGAACGCTA | CGAGAGGTAT | TCTTACGCCG | AGAGACAGCT | GATTGCACCT | 3180 |

```
GACTCTCACG  TTAATGTATG  TTTAATGGTC  TCCATCATAT  ATTTGTGTAT  ATTTTGAATC   3240
TTGCATGTGT  TTTAACATAG  CATATAACTG  ATTATTGGCT  TTCATGTTGG  AAATTAATTG   3300
TGAAGGCACA  GACGAACTGG  TCAATGGAGT  ATAGCAGGCT  TAAGGCCAAG  ATTGAGCTTT   3360
TGGAGAGAAA  CCAAAGGTAC  ATAGTACATT  TAAATTTATT  GTAGTAGTTA  AATATTGAGG   3420
AATAACAGAA  GAGAGAATGT  TCTTAATTAA  CTAAATCATC  ATAGGCATTA  TCTGGGAGAA   3480
GAGTTGGAAC  CAATGAGCCT  CAAGGATCTC  CAAAATCTGG  AGCAGCAGCT  TGAGACTGCT   3540
CTTAAGCACA  TTCGCTCCAG  AAAAGTGTGT  AAATATATCC  CACACTCTAT  CTCTATGCAT   3600
AACTAACTTT  GACTTTGTGT  GGATGTATTA  CATATAGTCA  AATATTGTAT  AGAGATTGTC   3660
TCATATAAAT  AAATAATTTT  TGGCCTTTTT  GTATGCAGAA  TCAACTCATG  AATGAGTCCC   3720
TCAACCACCT  CCAAAGAAAG  GTAGCTAAGT  TAAAACCATT  TTATCTCTCA  AGTCCTGTGT   3780
GTATAGAGTC  ATGACTTATA  TGTTAGAGAT  ATAAATCTTT  TAATAAATAA  ATAACATATA   3840
GGTTATATAT  AATTCAGGTT  AATATATTAT  TAATTACTAG  ATGTATATAT  ACTTATATAG   3900
ATCATATAAA  AAGAGAAATT  GACAATGGTG  TCATTTTTGT  GGAAATGACA  GGAGAAGGAG   3960
ATACAGGAGG  AAAACAGCAT  GCTTACCAAA  CAGGTGATCA  TTGTTTTTG   CATTTCTAAC   4020
TGTTTCACTA  TTTACAATTC  CACTGTTGAA  CTCCACTTCA  ATCTCTACCT  TAACGTACCA   4080
TCTCTCCACT  TTCGGCCCCA  ACTCTTTTGA  GTAAAAGAA   TTGATATGTA  GTTTCTTTTG   4140
ATTGGTATAA  TCATGAGCCT  AGCTGCACGT  ATAGGTAAGC  TTTGTCCGTT  TAGTATTAAG   4200
GTTGTCTCCC  AGATTTGAAC  TTGAACTTGA  ACTGTCTTCT  CATAATCATA  GTCTATGTGT   4260
AAATTACACA  TACATTAGCT  AGATAGCTAG  GAGCTATATT  TTAAGTTTTA  TTGAAGTA    4320
AGAAAACGTA  CGATGAAACT  ACTTGATTAA  GAACATATAT  TAAATGAAAA  AATATCACAA   4380
TAGTAAGACC  TTGACGACGC  TAAAATTCGC  TTAACATTTT  GCAGATTTAA  TTATTACTTT   4440
GCATTTTGTT  TGAAAATATC  ATATTACAAA  AAAAGTATA   AGAATAAAA   ATTGAAGTTC   4500
CTTGAATAAA  TGCAAATAGC  TGATTAGTTG  CAAATGGGAA  TCTATATAAC  GATGATGCTT   4560
ATATCATTTT  CTTGGCGTGT  GTAATCGGTA  TAGATAAAGG  AGAGGGAAAA  CATCCTAAAG   4620
ACAAAACAAA  CCCAATGTGA  GCAGCTGAAC  CGCAGCGTCG  ACGATGTACC  ACAGCCACAA   4680
CCATTTCAAC  ACCCCCATCT  TTACATGATC  GCTCATCAGA  CTTCTCCTTT  CCTAAATATG   4740
GGGTAACGGC  AGTATTTCTT  ATTTTTTTAA  GTTCTTTTTT  CTTACCATAA  TGTCAAATTC   4800
TCATATATAG  TGAAGTGTTG  TCAGTCAGTC  ATATAGGCAA  TGATAGTGAA  TGCACTTCAT   4860
ATATAGGGTT  TGTGTTAGGT  ATGGCGTTAG  AGGTTGATGG  TATGCATGCA  TATTATTGTA   4920
TTATGATTTT  TAATTTGCTA  TATATGATTG  TAATTTCAGT  GGTTTGTACC  AAGGAGAAGA   4980
CCAAACGGCG  ATGAGGAGGA  ACAATCTGGA  TCTGACTCTT  GAACCCATTT  ACAATTACCT   5040
TGGCTGTTAC  GCCGCTTGAA  TAGACTACAT  CGATCTATAT  CAATCTCTTT  AAAATAATAT   5100
AAGATCGATC  CTCTATTCAT  GATCTATATT  AAACACCGGT  TAATTAATAT  ATTTTGGTA    5160
TGTCCTTATA  TCATATCAAC  ATCATCAAGC  CTTTTTCCAA  TTCAATATAT  CTTGTATTTC   5220
GGGGAGCAAT  GAATAAATGT  AATATTTGTG  GACTGAGAGA  GCTAGAAAGA  ATTGTTGTTC   5280
AAACCTTTTC  TATATTGATC  TCATCGTTAC  ATTGTAATTT  GATTTCTTTC  ACACCCCAAA   5340
ATATTTGTAA  TACGAATTTA  GTCTTTGATG  ATTTGAACTT  TACTTGGTCA  AAGTAAATCA   5400
CAGCCTTAGA  AGGTAAATTT  TGAATTGAAA  ATAGAAATAA  AAATGTTGGG  AACGTGACAT   5460
TCGGTTTCTT  CTCCATTTGC  TTCATGTAGG  TGCGTGATAC  GATCGGAAAT  GAGAATTATT   5520
GGGCCCTTGT  GGGCTTCATA  ATTATTAGTT  CATTGTTTAA  GCCCATAATA  CTTGGCATTT   5580
```

-continued

| | | | | | |
|---|---|---|---|---|---|
| TTGCCAAAGA | AGAAACTGTA | TAAAAGAAAT | CGGAGAAGAA | AAGAAAAATA | GTAGTCGCGG | 5640
| CAATGGAGGA | TCTATGGAAG | AGGGCAAAAT | CGTTCGCAGA | AGAAGCGGGT | AAGAAGTCTC | 5700
| AGACGATAAC | ACAATCATCC | TCCGCGACCT | TCGTCAATCT | CGTCACCGAG | ACTGCTAAGA | 5760
| AATCCAAGGA | ACTCGCTCTC | GAAGCTTCGA | AGAAAGCTGA | TCAATTCAAT | GCCGCCGATT | 5820
| TCGTTGCTGA | AACGGCTAAG | AAATCCAAAG | AATTC | | | 5855

( 2 ) INFORMATION FOR SEQ ID NO:21:

( i ) SEQUENCE CHARACTERISTICS:
  ( A ) LENGTH: 1120 base pairs
  ( B ) TYPE: nucleic acid
  ( C ) STRANDEDNESS: double
  ( D ) TOPOLOGY: linear ( i i ) MOLECULE TYPE: DNA (genomic)

( i x ) FEATURE:
  ( A ) NAME/KEY: unsure
  ( B ) LOCATION: 389..393
  ( D ) OTHER INFORMATION: /note= "N = one or more
   nucleotides."

( i x ) FEATURE:
  ( A ) NAME/KEY: unsure
  ( B ) LOCATION: 810..814
  ( D ) OTHER INFORMATION: /note= "N = one or more
   nucleotides."

( i x ) FEATURE:
  ( A ) NAME/KEY: unsure
  ( B ) LOCATION: 1118..1120
  ( D ) OTHER INFORMATION: /note= "N = one or more
   nucleotides."

( i x ) FEATURE:
  ( A ) NAME/KEY: misc_feature
  ( B ) LOCATION: 1..1120
  ( D ) OTHER INFORMATION: /note= "sequence = Brassica
   oleracea CAL gene"

( x i ) SEQUENCE DESCRIPTION: SEQ ID NO:21:

| | | | | | |
|---|---|---|---|---|---|
| TCTAGATAAT | CTTCTCAAGA | AGGATTTAGA | ATGGCATAAT | CCAAAGGCTC | AAATCTCGGC | 60
| ATCTGAAACC | ATATTATCAA | TTTATTCATG | ATTTAGGATG | CAACCAATTA | AAAATAATCA | 120
| GTGCATATGA | TTTCATAAGT | CTCTCGACCA | AAACACTTTA | CTACTCGATC | ATGGTGCGAA | 180
| ACAAGTCGAG | AATGCTAGGT | CTATATGTGA | TGCTTAGGCC | ACACGGCATG | TAATGTGATA | 240
| CAACGATCCT | AGAGATCGGT | TCTGAGATAT | GCAAGCAAGG | TCACACGACC | ATTCATATAT | 300
| GGTGTCTCTC | TAGGCCACAC | GGCAAGCTAT | GATGCATTAA | GCCACACGGC | TTTCAATCAC | 360
| ATGATGCAAC | AATGTGATCT | ATCAAGGGNN | NNNCTCGAGC | TGCACACAGA | CGGACGCGAG | 420
| CTGGCTGTCG | TCGGATGCGA | GCTGAACGGG | ACGGACTCG | TCTGCTTCCT | ATCGGGTTCG | 480
| CGAGCTGCTT | CCTATCGGGT | TTTCAAGCGG | CTGATCGGGA | TTACAAGCTG | GTTGATCAGG | 540
| AACACGAGCT | GGCTGTGATG | CGAACGGAAG | CTGAGGTTGT | CTAGGATCAG | GAACACCTTA | 600
| GGGATGGAGC | TGATCGGTTG | CTGACGAGCT | GGAACGCGAG | CTAGGACGAA | TTAGGGTTCG | 660
| TCGGGATTAG | GTTAAAGTCG | CCGGCTAGGT | TAGGTTTAAG | GGATTGGCGA | TTTTAGCTTA | 720
| GATTGCAGAG | AACAATCGTG | CTGATAACAT | GTTGTAATTA | GAAGATTGAA | GATTGAATAG | 780
| TTCTGTGTTT | TATTAACATA | ACATGAATTN | NNNAAAGAT | TCCACGAGTT | TCGTACATGT | 840
| TCTATTGCTA | GTTAGGTTAA | GGGAGTTAAG | CAAAGTAGAG | TGATTGGCAT | TAACTCTTCA | 900
| GTAGTGCCCA | CGAAGACTCT | AGTTAGAAGT | CAGTTCAATC | TGACAAGCTG | TTAGAGGTTC | 960
| ACTAACACTT | GAGTTTGGAT | CTTGAAGGTC | CATATAATAG | TATAACGTAG | ACCCAATATA | 1020

| ATACAAAACT | ATAGTATTGA | CTATAAATTT | GAGTGTCTAC | ACCAACTCGT | TTAAGCAAGA | 1080 |
| CAGGTCCCGA | GACCGGAGTG | GTTTCTTTGT | TGAGCTCNNN | | | 1120 |

( 2 ) INFORMATION FOR SEQ ID NO:22:

( i ) SEQUENCE CHARACTERISTICS:
        ( A ) LENGTH: 4816 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: unsure
        ( B ) LOCATION: 700..709
        ( D ) OTHER INFORMATION: /note= "N = one or more
            nucleotides."

( i x ) FEATURE:
        ( A ) NAME/KEY: unsure
        ( B ) LOCATION: 3846..3853
        ( D ) OTHER INFORMATION: /note= "N = one or more
            nucleotides."

( i x ) FEATURE:
        ( A ) NAME/KEY: unsure
        ( B ) LOCATION: 4545..4548
        ( D ) OTHER INFORMATION: /note= "N = one or more
            nucleotides."

( i x ) FEATURE:
        ( A ) NAME/KEY: misc_feature
        ( B ) LOCATION: 1..4816
        ( D ) OTHER INFORMATION: /note= "sequence = Brassica
            oleracea var. botrytis CAL gene"

( x i ) SEQUENCE DESCRIPTION: SEQ ID NO:22:

| AAGCTTTAGG | GTTTTAGGGT | TTTTGATTCC | AAGATTTAGG | GTTTTCATAA | TTCAGATCAG | 60 |
| AACAATCAAT | CAACATGTTC | TAATGGAATC | GATTTCAATC | TAGTGATTAT | AAGATGATCA | 120 |
| GTTTTAGGTT | ATACCAATTT | TTAGGATTTA | TCAAGATCAT | TGGATTTCCA | TAATAATGGA | 180 |
| TTAGGGTTTT | AGGGTTTGAT | CATTATGTTT | TTAGATTAAT | CGGTATACTT | TTGTTTGTAG | 240 |
| GGTTGAAACC | GGACCACCAA | AGAGAACGGA | TGAACCTCGA | GCTGCACACC | GACAGATGCG | 300 |
| AGCTGGCTGT | CGTCGGATGC | GAGCTGAACG | GGACGGGACG | CGTCTGCTTC | CTATCGGGTT | 360 |
| CGCGAGCTGC | TTCCTATCGG | GTTTGCAAGC | GGCTGATCGG | GATTGCGAGC | TGGTTGATCG | 420 |
| GGAACACGAG | CTGGCTGTGA | TGCGAACGGA | AGCTGAGGTC | GTCTAGGATC | AGGAACACCT | 480 |
| TAGGGATGGA | GCTGATCGGT | TGCTGACGAG | CTGGAACGCG | AGCTAGGACA | AATTAGGGTT | 540 |
| CGTCGGGATT | AGGTTAAAGT | CGCCGGCTAG | GTTAGGTTTA | AGGGATTGGC | GATTTTAGCT | 600 |
| TAGATTGCAG | AGAACAATCG | TGCTGATAAC | GTGTTGTAAA | ACAAACGGTT | TTAGAAACTG | 660 |
| AATGTTTATG | TGTATTATTA | ATCATAATAT | GGGTTTTTTN | NNNNNNNNT | ACAGTGCGAG | 720 |
| AATGATAGAC | TCGCATAGCC | AATGAAGTCC | AGTCAGACCA | ATGAGAAGTC | GACAGCAAAA | 780 |
| CCTAGTAAAC | TACTCTTGTT | TTATCCTTGT | CCAAAACCAG | CTTTAGGTTT | CCCTGAAACC | 840 |
| GCTTATTCCA | AAACATCTTC | TCCTTAAATA | AGAAAGACT | CTTTCACATT | GTTATTATCA | 900 |
| TCAGAAGGGA | AAGAAGAAAA | ACTTTCCTAA | TTAGATCGAG | CTTGTCGTTA | TCTCTCTATT | 960 |
| ATAGTTTATA | TTTCTTACTG | GGGCTTGTTT | GGTTGCTTCT | CTTTTTGGAC | TTCTTTTATA | 1020 |
| TAATTTATAT | ATTCTACGAG | AAATGGGAAG | GGGTAGGGTT | GAAATGAAGA | GGATAGAGAA | 1080 |
| CAAGATCAAC | AGACAAGTGA | CGTTTTCGAA | AAGAAGAGCT | GGTCTTTTGA | AGAAAGCCCA | 1140 |

```
TGAGATCTCG  ATTCTTTGTG  ATGCTGAGGT  TTCCCTTATT  GTCTTCTCCC  ATAAGGGGAA   1200
ACTGTTCGAG  TACTCGTCTG  AATCTTGGTA  ACTGCATAAT  TCCCTTTTTA  ATTGTTTTAG   1260
TGTGCCTTTG  TTCGCCCTAA  TAAATAGTTT  TTGTTCTCCT  TTAGGCCATT  TCTTGGTATC   1320
TTCTTATGTT  TTTATGAAAA  TTCTCACAAA  TTTTGTAGTT  AATTACTTGG  ATCTACGAAT   1380
TGATTTCACC  AAAGTGAAAT  TAAACCATTA  TAGCATATTT  GCTTATATCA  GAAGAAAATA   1440
AAAAAAATAG  GGCATAATAA  GGTGTTATGT  GAAGTGAAAG  TTTACTTCAG  GTAACACGTT   1500
ATTAAGATAT  GCTTAACCCT  AGATCAAGAT  CTACTTCTAC  TGGTCGCGAC  ATGGATTTAC   1560
AAGAAATCGT  CACTGTATAT  GAACTTTAAT  TTAAACATGT  ATAGACCTTT  TTGTTTCAAA   1620
TAGAGAGTTA  AGTAATTTAA  TCATAGAAAG  AACCAACGTT  ATGTTCATCT  AGGCTAGAGT   1680
GATTTTTGCC  TAACAATTTT  GAAAAGCTGT  CCTTATGCTT  AAATATCTTT  CAGCAGCATA   1740
GTAGTATGAA  AGAAAATATT  TCAATATCGT  TGTATAAGG   TTCTATAATT  TTCGTTTTTT   1800
TTTTTTTCGC  AAATGGTTTA  TATAGAGAAA  CTAGAACTAG  GGATGTGACA  TCTAGGTATA   1860
GGGGTCTTTG  ACCTCTGGGA  TCAATGTAAA  AGAGACCATT  CTATTTTCTA  TCAACTTCTC   1920
AGTTTCCGAT  GGTCAAAACT  TAACTTCAAC  AACTGTTTTT  CTTTTCAGAA  GAGGACAAAC   1980
TATTATATGT  ATATTATGTT  ATGTCGTTTC  ATACATAAAT  ATCTAATAAC  AAATTTATTT   2040
TTAAAAACAT  ATAACAAAAC  TTTATTGAAG  AATTGGAAAC  TCAAAACGGG  GACATATAGG   2100
ACGCTGCACG  TCTAGAGGTG  TGGGGTTAGT  GATTCAACGG  GTTTTTAATG  TAGAGAAACT   2160
GTAGATGTAA  GATTGTTTCT  AGGGTTAAGG  CACTAAACCA  GGGATTATCT  CTTTTCCATG   2220
ATAAAGTTA   ATGTCTTAAA  TGCATCGCTA  ATTAATTAGG  CAAACTAGAT  GATAGTACGT   2280
AGTGTGTGTG  TGTGTGTGTA  TTGGATATTT  TGGGTTAATA  GTTACATCTT  AGACAAATGT   2340
GTGGTCTTCT  GATAAGCTGA  GAAAATATTT  GGGTGCAGAC  TCTTAGTGGT  AATTAATTAT   2400
ATCTAGAAAN  NCCCANATAC  NAATTTAATA  CGGCTACTTT  TTGGGTGAAT  GAATCTACAC   2460
TAACCCTAAG  CCTAATGATA  GCATGGAGAA  GGTACTAGAA  CGCTACGAGA  GGTACTCTTA   2520
CGCCGAGAAA  CAGCTAAAAG  CTCCAGACTC  TCACGTCAAT  GTATGTTTAA  TGATCTCCAA   2580
GACTCTGTCA  AACATATATG  TACTATATCT  TGAATGTGTT  TTCTTAATTA  ACATAATTGA   2640
TGCACTGTTT  ACATAATGAA  AATTAATTGT  GTAGGCACAA  ACGAACTGGT  CAATGGAATA   2700
TAGCAGGCTT  AAGGCTAAGA  TTGAGCTTTG  GGAGAGGAAC  CAAAGGTACT  TATAGAATTT   2760
AGGAATTAGC  ATGTGTAAAT  AATAGTTTAT  TGTATTAGTT  TTTTTTGGTA  AAATTATTGT   2820
ATTAGTTAAA  CACTGGGAAT  TAACAAAAAA  GATGGTGGTA  TGGATTAATC  ATAGGCATTA   2880
TCTGGGAGAA  GATTAGAAT   CAATCAGCAT  AAAGGAGCTA  CAGAATCTGG  AGCAGCAGCT   2940
TGACACTTCT  CTTAAACATA  TTCGCTCCAG  AAAAGTGTGT  AAATAAGCAC  ATACAAACGC   3000
AAACATCTCT  ATCTTATCTT  TGAGTTTGTG  AAGATATATA  TGCCTAATTT  TATATAGAGT   3060
TTGTCTCATA  TGAATGAATA  CAATTTGAAC  TCAATTGTAT  GCAGAATCAA  CTAATGCACT   3120
AGTCCCTCAA  CCACCTCCAA  AGAAAGGTAC  GTTAAAACCA  TTTCATCTCT  CAAGTCGTAC   3180
GTGTGTATGT  GTGACTTATG  TTACCGTTTA  AATCTTTCAG  TTAAATACAA  AACATATGGT   3240
TTTACACATG  TTAGACTATT  TTGGTGAAGG  AAACATTGTA  AATGTAAACA  AAGGGGTTTT   3300
TTGGATTGAA  TAAAATTTAA  CATTCATTCA  AAAAAAACAT  ATGGTTCATA  TATATATTCG   3360
GTTTATATGA  TTATATATAT  ATATTTATAT  AGGTTAATAT  ATTAGTGTTT  AATTATATGT   3420
GTATACATAT  AGATGTAGAA  AGAACCTCTA  GAGCGATCCC  TGAGAATTGT  TTCATTTTGT   3480
AAAATTGACA  GGAGAAAGAA  ATACTGGAGG  AAAACAGCAT  GCTTGCCAAA  CAGGTAATCA   3540
```

-continued

```
TTGTATGTTG CATTTTTTAC TGTTTCACAA CTGTTTTACT ATTTAAACTC CACTGTTCTA      3600

CTCCACTTCA ACCTTAAACT ACCATTGCTC AACTTTCGGC ACCAACTCTT TTTTAAAAAG      3660

GAAGAATTAG TTGTTTCATG TGATTGGTAT AATCATGAGC ATATGTGCAC ACATGTAGGT      3720

GGGCTTTGTC CGTTTAGTAT TAAGGTTGTC TCCTAGAATT GAACTTGAAC TGTCTTCTCG      3780

TAATCATAGT CTATATATAA CACGCTGCAC ATACAGTAGC CAGTAGGTTT ATTTGAGCAA      3840

GATACNNNNN NNNTGCTCTT ACTGTAATAC CGTGCCAACA TTGATTGTGA TTCGATACAT      3900

AAATTTAGTT GATCATAACG TTTATCGGTA TTTGAAATTG GTAGATAAAG GAGAGGGAGA      3960

GTATCCTAAG GACACATCAA AACCAATCAG AGCAGCAAAA CCGCAGCCAC CATGTAGCTC      4020

CTCAGCCGCA ACCGCAGTTA AATCCTTACA TGGCATCATC TCCTTTCCTA AATATGGGGT      4080

AACGGTAGTG TTTCATTTTT ATCTTGGTAT ACATATATAC ATATAGATCC GACACTCTTG      4140

GTGTTAGTAA TTCAGTGTAT GCGATGATGT TGTATGTATG TATGTTCATA TTTAGGGTTT      4200

GTGTTAAGTG TGGCGTTAGA GGTTGATGGC TTTGTAACTA CATGTCTAGA ACTATACAAT      4260

AATTAATAAG ATGGAATGAT ATATATATAT ACATATATTT TAATTTGCCA TATGATTGTG      4320

ATTTCAGTGG CATGTACCAA GGAGAATATC CAACGGCGGT GAGGAGGAAC CGTCTCGATC      4380

TGACTCTTGA ACCCATTTAC AACTGCAACC TTGGTTACTT TGCCGCATGA ATGGACTCGC      4440

CATATATCGA CATAAAATAA TTTATATAAG ATCGATTTTT ACGTATAATA ATAGGCAGCA      4500

ATGGTTAGCC ACCATATCTA TATACACTGG AAATTCTATT TATCNNNNTT ACATTGATTT      4560

ATACTACATA AACCCTCCAG ACCAAACTCG TCTCCATGCC AACTGATAGA TTTCCTAGAC      4620

ATGCTACACA CTCCATGACT CCGACTAATT TTTGGTTTGG CGTTTCTAT GTTTTATTA       4680

ATTGTTTTGA ATTTACTCT TTCACGATAT TTAAAATTTT TCAAACTTAT TTTTGTTGCT      4740

CACAGTGAAC AAATCTTCTG TGAAGAAGTG GTATATATTC TGTGGAGCCA CTTCCCCAAT      4800

GTTCTTTGGT GGATCC                                                     4816
```

( 2 ) INFORMATION FOR SEQ ID NO:23:

( i ) SEQUENCE CHARACTERISTICS:
        ( A ) LENGTH: 855 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..853

( i x ) FEATURE:
        ( A ) NAME/KEY: misc_feature
        ( B ) LOCATION: 1..855
        ( D ) OTHER INFORMATION: /note= "product = Rat
            glucocorticoid receptor ligand binding domain"

( x i ) SEQUENCE DESCRIPTION: SEQ ID NO:23:

```
ACA AAG AAA AAA ATC AAA GGG ATT CAG CAA GCC ACT GCA GGA GTC TCA       48
Thr Lys Lys Lys Ile Lys Gly Ile Gln Gln Ala Thr Ala Gly Val Ser
 1               5                  10                  15

CAA GAC ACT TCG GAA AAT CCT AAC AAA ACA ATA GTT CCT GCA GCA TTA       96
Gln Asp Thr Ser Glu Asn Pro Asn Lys Thr Ile Val Pro Ala Ala Leu
            20                  25                  30

CCA CAG CTC ACC CCT ACC TTG GTG TCA CTG CTG GAG GTG ATT GAA CCC      144
Pro Gln Leu Thr Pro Thr Leu Val Ser Leu Leu Glu Val Ile Glu Pro
        35                  40                  45

GAG GTG TTG TAT GCA GGA TAT GAT AGC TCT GTT CCA GAT TCA GCA TGG      192
Glu Val Leu Tyr Ala Gly Tyr Asp Ser Ser Val Pro Asp Ser Ala Trp
    50                  55                  60
```

| | | | | | | | | | | | | | | | | |
|---|---|---|---|---|---|---|---|---|---|---|---|---|---|---|---|---|
| AGA | ATT | ATG | ACC | ACA | CTC | AAC | ATG | TTA | GGT | GGG | CGT | CAA | GTG | ATT | GCA | 240 |
| Arg | Ile | Met | Thr | Thr | Leu | Asn | Met | Leu | Gly | Gly | Arg | Gln | Val | Ile | Ala | |
| 65 | | | | | 70 | | | | | 75 | | | | | 80 | |
| GCA | GTG | AAA | TGG | GCA | AAG | GCG | ATA | CTA | GGC | TTG | AGA | AAC | TTA | CAC | CTC | 288 |
| Ala | Val | Lys | Trp | Ala | Lys | Ala | Ile | Leu | Gly | Leu | Arg | Asn | Leu | His | Leu | |
| | | | | 85 | | | | | 90 | | | | | 95 | | |
| GAT | GAC | CAA | ATG | ACC | CTG | CTA | CAG | TAC | TCA | TGG | ATG | TTT | CTC | ATG | GCA | 336 |
| Asp | Asp | Gln | Met | Thr | Leu | Leu | Gln | Tyr | Ser | Trp | Met | Phe | Leu | Met | Ala | |
| | | | 100 | | | | | 105 | | | | | 110 | | | |
| TTT | GCC | TTG | GGT | TGG | AGA | TCA | TAC | AGA | CAA | TCA | AGC | GGA | AAC | CTG | CTC | 384 |
| Phe | Ala | Leu | Gly | Trp | Arg | Ser | Tyr | Arg | Gln | Ser | Ser | Gly | Asn | Leu | Leu | |
| | | | 115 | | | | 120 | | | | | 125 | | | | |
| TGC | TTT | GCT | CCT | GAT | CTG | ATT | ATT | AAT | GAG | CAG | AGA | ATG | TCT | CTA | CCC | 432 |
| Cys | Phe | Ala | Pro | Asp | Leu | Ile | Ile | Asn | Glu | Gln | Arg | Met | Ser | Leu | Pro | |
| | | 130 | | | | 135 | | | | | 140 | | | | | |
| TGC | ATG | TAT | GAC | CAA | TGT | AAA | CAC | ATG | CTG | TTT | GTC | TCC | TCT | GAA | TTA | 480 |
| Cys | Met | Tyr | Asp | Gln | Cys | Lys | His | Met | Leu | Phe | Val | Ser | Ser | Glu | Leu | |
| 145 | | | | | 150 | | | | | 155 | | | | | 160 | |
| CAA | AGA | TTG | CAG | GTA | TCC | TAT | GAA | GAG | TAT | CTC | TGT | ATG | AAA | ACC | TTA | 528 |
| Gln | Arg | Leu | Gln | Val | Ser | Tyr | Glu | Glu | Tyr | Leu | Cys | Met | Lys | Thr | Leu | |
| | | | | 165 | | | | | 170 | | | | | 175 | | |
| CTG | CTT | CTC | TCC | TCA | GTT | CCT | AAG | GAA | GGT | CTG | AAG | AGC | CAA | GAG | TTA | 576 |
| Leu | Leu | Leu | Ser | Ser | Val | Pro | Lys | Glu | Gly | Leu | Lys | Ser | Gln | Glu | Leu | |
| | | | 180 | | | | | 185 | | | | | 190 | | | |
| TTT | GAT | GAG | ATT | CGA | ATG | ACT | TAT | ATC | AAA | GAG | CTA | GGA | AAA | GCC | ATC | 624 |
| Phe | Asp | Glu | Ile | Arg | Met | Thr | Tyr | Ile | Lys | Glu | Leu | Gly | Lys | Ala | Ile | |
| | | | 195 | | | | 200 | | | | | 205 | | | | |
| GTC | AAA | AGG | GAA | GGG | AAC | TCC | AGT | CAG | AAC | TGG | CAA | CGG | TTT | TAC | CAA | 672 |
| Val | Lys | Arg | Glu | Gly | Asn | Ser | Ser | Gln | Asn | Trp | Gln | Arg | Phe | Tyr | Gln | |
| | 210 | | | | | 215 | | | | | 220 | | | | | |
| CTG | ACA | AAG | CTT | CTG | GAC | TCC | ATG | CAT | GAG | GTG | GTT | GAG | AAT | CTC | CTT | 720 |
| Leu | Thr | Lys | Leu | Leu | Asp | Ser | Met | His | Glu | Val | Val | Glu | Asn | Leu | Leu | |
| 225 | | | | | 230 | | | | | 235 | | | | | 240 | |
| ACC | TAC | TGC | TTC | CAG | ACA | TTT | TTG | GAT | AAG | ACC | ATG | AGT | ATT | GAA | TTC | 768 |
| Thr | Tyr | Cys | Phe | Gln | Thr | Phe | Leu | Asp | Lys | Thr | Met | Ser | Ile | Glu | Phe | |
| | | | | 245 | | | | | 250 | | | | | 255 | | |
| CCA | GAG | ATG | TTA | GCT | GAA | ATC | ATC | ACT | AAT | CAG | ATA | CCA | AAA | TAT | TCA | 816 |
| Pro | Glu | Met | Leu | Ala | Glu | Ile | Ile | Thr | Asn | Gln | Ile | Pro | Lys | Tyr | Ser | |
| | | | 260 | | | | | 265 | | | | | 270 | | | |
| AAT | GGA | AAT | ATC | AAA | AAG | CTT | CTG | TTT | CAT | CAA | AAA | T GA | | | | 855 |
| Asn | Gly | Asn | Ile | Lys | Lys | Leu | Leu | Phe | His | Gln | Lys | | | | | |
| | | 275 | | | | | 280 | | | | | | | | | |

( 2 ) INFORMATION FOR SEQ ID NO:24:

( i ) SEQUENCE CHARACTERISTICS:
        ( A ) LENGTH: 284 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| | | | | | | | | | | | | | | |
|---|---|---|---|---|---|---|---|---|---|---|---|---|---|---|
| Thr | Lys | Lys | Lys | Ile | Lys | Gly | Ile | Gln | Gln | Ala | Thr | Ala | Gly | Val | Ser |
| 1 | | | | 5 | | | | | 10 | | | | | 15 | |
| Gln | Asp | Thr | Ser | Glu | Asn | Pro | Asn | Lys | Thr | Ile | Val | Pro | Ala | Ala | Leu |
| | | | 20 | | | | | 25 | | | | | 30 | | |
| Pro | Gln | Leu | Thr | Pro | Thr | Leu | Val | Ser | Leu | Leu | Glu | Val | Ile | Glu | Pro |
| | | | 35 | | | | | 40 | | | | | 45 | | |
| Glu | Val | Leu | Tyr | Ala | Gly | Tyr | Asp | Ser | Ser | Val | Pro | Asp | Ser | Ala | Trp |
| | | 50 | | | | | 55 | | | | | 60 | | | |

| | | | | | | | | | | | | | | |
|---|---|---|---|---|---|---|---|---|---|---|---|---|---|---|
|Arg|Ile|Met|Thr|Thr|Leu|Asn|Met|Leu|Gly|Gly|Arg|Gln|Val|Ile|Ala|
|65| | | | |70| | | | |75| | | | |80|

Arg Ile Met Thr Thr Leu Asn Met Leu Gly Gly Arg Gln Val Ile Ala
65                    70                    75                    80

Ala Val Lys Trp Ala Lys Ala Ile Leu Gly Leu Arg Asn Leu His Leu
              85                    90                        95

Asp Asp Gln Met Thr Leu Leu Gln Tyr Ser Trp Met Phe Leu Met Ala
            100                105                    110

Phe Ala Leu Gly Trp Arg Ser Tyr Arg Gln Ser Ser Gly Asn Leu Leu
        115                120                    125

Cys Phe Ala Pro Asp Leu Ile Ile Asn Glu Gln Arg Met Ser Leu Pro
    130                135                140

Cys Met Tyr Asp Gln Cys Lys His Met Leu Phe Val Ser Ser Glu Leu
145                150                155                    160

Gln Arg Leu Gln Val Ser Tyr Glu Glu Tyr Leu Cys Met Lys Thr Leu
                165                170                    175

Leu Leu Leu Ser Ser Val Pro Lys Glu Gly Leu Lys Ser Gln Glu Leu
            180                185                    190

Phe Asp Glu Ile Arg Met Thr Tyr Ile Lys Glu Leu Gly Lys Ala Ile
        195                200                    205

Val Lys Arg Glu Gly Asn Ser Ser Gln Asn Trp Gln Arg Phe Tyr Gln
    210                215                    220

Leu Thr Lys Leu Leu Asp Ser Met His Glu Val Val Glu Asn Leu Leu
225                230                235                        240

Thr Tyr Cys Phe Gln Thr Phe Leu Asp Lys Thr Met Ser Ile Glu Phe
            245                250                    255

Pro Glu Met Leu Ala Glu Ile Ile Thr Asn Gln Ile Pro Lys Tyr Ser
        260                265                    270

Asn Gly Asn Ile Lys Lys Leu Leu Phe His Gln Lys
            275                280

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..20
        ( D ) OTHER INFORMATION: /note= "sequence name = AGL10-1"

( x i ) SEQUENCE DESCRIPTION: SEQ ID NO:25:

GATCGTCGTT ATCTCTCTTG    20

( 2 ) INFORMATION FOR SEQ ID NO:26:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..19
        ( D ) OTHER INFORMATION: /note= "sequence name = ALG10-12"

( x i ) SEQUENCE DESCRIPTION: SEQ ID NO:26:

GTAGTCTATT CAAGCGGCG    19

( 2 ) INFORMATION FOR SEQ ID NO:27:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..19
        ( D ) OTHER INFORMATION: /note= "sequence name = ALG10-2"

( x i ) SEQUENCE DESCRIPTION: SEQ ID NO:27:

GATGGAGACC ATTAAACAT                                                   19

( 2 ) INFORMATION FOR SEQ ID NO:28:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..18
        ( D ) OTHER INFORMATION: /note= "sequence name = AGL10-3"

( x i ) SEQUENCE DESCRIPTION: SEQ ID NO:28:

GGAGAAGGTA CTAGAACG                                                     18

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..18
        ( D ) OTHER INFORMATION: /note= "sequence name = ALG10-4"

( x i ) SEQUENCE DESCRIPTION: SEQ ID NO:29:

GCCCTCTTCC ATAGATCC                                                     18

( 2 ) INFORMATION FOR SEQ ID NO:30:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..19
        ( D ) OTHER INFORMATION: /note= "sequence name = BOB1"

( x i ) SEQUENCE DESCRIPTION: SEQ ID NO:30:

TCTACGAGAA ATGGGAAGG                                                   19

( 2 ) INFORMATION FOR SEQ ID NO:31:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
    ( A ) NAME/KEY: misc_feature
    ( B ) LOCATION: 1..19
    ( D ) OTHER INFORMATION: /note= "sequence name = BOB2"

( x i ) SEQUENCE DESCRIPTION: SEQ ID NO:31:

GTCGATATAT GGCGAGTCC                                                                   19

( 2 ) INFORMATION FOR SEQ ID NO:32:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..19
        ( D ) OTHER INFORMATION: /note= "sequence name = BOB4B"

( x i ) SEQUENCE DESCRIPTION: SEQ ID NO:32:

CCATTGACCA GTTCGTTTG                                                                   19

( 2 ) INFORMATION FOR SEQ ID NO:33:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..18
        ( D ) OTHER INFORMATION: /note= "sequence name = BOB33"

( x i ) SEQUENCE DESCRIPTION: SEQ ID NO:33:

GCTCCAGACT CTCACGTC                                                                    18

We claim:

1. An isolated nucleic acid molecule encoding a CAULIFLOWER (CAL) gene product having at least about 89 percent amino acid identity with amino acids 1 to 160 of the Arabidopsis CAL sequence shown in FIG. 5 (SEO ID NO:10).

2. The isolated nucleic acid molecule of claim 1, wherein said CAL gene product is selected from the group consisting of Arabidopsis thaliana CAL having the amino acid sequence shown in FIG. 5 (SEQ ID NO: 10) and Brassica oleracea CAL having the amino acid sequence shown in FIG. 6 (SEQ ID NO: 12).

3. An isolated nucleic acid molecule selected from the group consisting of a nucleic acid molecule having the nucleic acid sequence shown in FIG. 5 (SEQ ID NO: 9) and a nucleic acid molecule having the nucleic acid sequence shown in FIG. 6 (SEQ ID NO: 11).

4. An isolated nucleic acid molecule encoding a truncated CAL gene product having at least about 70 percent amino acid identity with amino acids 1 to 150 of the sequence shown in FIG. 7 (SEQ ID NO:14) wherein, upon ectopic expression in an angiosperm, said truncated CAL gene product does not result in conversion of shoot meristem to floral meristem.

5. The isolated nucleic acid molecule of claim 4, wherein said truncated CAL gene product is Brassica oleracea var. botrytis CAL having the amino acid sequence shown in FIG. 7 (SEQ ID NO: 14).

6. An isolated nucleic acid molecule having the nucleic acid sequence shown in FIG. 7 (SEQ ID NO: 13).

7. An isolated CAL gene, comprising a CAL gene selected from the group consisting of an Arabidopsis thaliana CAL gene having the nucleotide sequence shown in FIG. 13 (SEQ ID NO: 20), a Brassica oleracea CAL gene having the nucleotide sequence shown in FIG. 14 (SEQ ID NO: 21) and a Brassica oleracea var. botrytis CAL gene having the nucleotide sequence shown in FIG. 15 (SEQ ID NO: 22).

8. A vector, comprising the nucleic acid molecule of claim 1.

9. A vector, comprising the gene of claim 7.

10. A vector, comprising a nucleic acid molecule selected from the group consisting of the nucleic acid molecule of claim 2 and the nucleic acid molecule of claim 3.

11. A host cell, comprising the vector of claim 8.

12. The vector of claim 8, wherein said vector is an expression vector.

13. An expression vector, comprising a nucleic acid molecule selected from the group consisting of the nucleic acid molecule of claim 2 and the nucleic acid molecule of claim 3.

14. The expression vector of claim 12, further comprising a cauliflower mosaic virus 35S promoter.

15. The expression vector of claim 12, further comprising an inducible regulatory element.

16. A kit for converting shoot meristem to floral meristem in an angiosperm, comprising the expression vector of claim 12.

17. A kit for promoting early flowering in an angiosperm, comprising the expression vector of claim 12.

18. An isolated nucleotide sequence, comprising at least 50 consecutive nucleotides of a nucleic acid molecule selected from the group consisting of:

a nucleic acid molecule having the nucleic acid sequence shown in FIG. 5 (SEQ ID NO:9) or a nucleic acid molecule complementary thereto;

a nucleic acid molecule having the nucleic acid sequence shown in FIG. 6 (SEQ ID NO:11) or a nucleic acid molecule complementary thereto; and a nucleic acid molecule having the nucleic acid sequence shown in FIG. 7 (SEQ ID NO:13) or a nucleic acid molecule complementary thereto.

provided that said isolated nucleotide sequence does not contain a MADS box sequence.

19. An isolated nucleotide sequence, comprising at least 50 consecutive nucleotides of a CAL gene selected from the group of CAL genes consisting of:

an *Arabidopsis thaliana* CAL gene having the nucleotide sequence shown in FIG. 13 (SEQ ID NO:20) or a sequence complementary thereto;

a *Brassica oleracea* CAL gene having the nucleotide sequence shown in FIG. 14 (SEQ ID NO:21) or a sequence complementary thereto; and a *Brassica oleracea* var. *botrytis* CAL gene having the nucleotide sequence shown in FIG. 15 (SEQ ID NO:22) or a sequence complementary thereto, provided that said isolated nucleotide sequence does not contain a MADS box sequence.

* * * * *